US008795184B2

(12) United States Patent
Niwa et al.

(10) Patent No.: US 8,795,184 B2
(45) Date of Patent: Aug. 5, 2014

(54) WIRELESS PLETHYSMOGRAM SENSOR UNIT, A PROCESSING UNIT FOR PLETHYSMOGRAM AND A PLETHYSMOGRAM SYSTEM

(75) Inventors: Daisuke Niwa, Kyoto (JP); Koji Terumoto, Kyoto (JP); Kazuhiro Oguchi, Kyoto (JP); Masahide Tanaka, Toyonaka (JP); Ken Nakahara, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 197 days.

(21) Appl. No.: 13/179,814

(22) Filed: Jul. 11, 2011

(65) Prior Publication Data

US 2012/0022382 A1    Jan. 26, 2012

(30) Foreign Application Priority Data

Jul. 12, 2010  (JP) ................. 2010-157479
Jul. 13, 2010  (JP) ................. 2010-158911
Sep. 10, 2010  (JP) ................. 2010-203782
Sep. 21, 2010  (JP) ................. 2010-210739
Oct. 12, 2010  (JP) ................. 2010-229782
Nov. 1, 2010  (JP) ................. 2010-245049
Nov. 2, 2010  (JP) ................. 2010-245894

(51) Int. Cl.
  *A61B 5/02*   (2006.01)
  *A61B 5/024*  (2006.01)
  *A61B 5/1455* (2006.01)
  *A61B 5/16*   (2006.01)
  *A61B 5/00*   (2006.01)

(52) U.S. Cl.
  CPC ........... *A61B 5/02416* (2013.01); *A61B 5/0022* (2013.01); *A61B 5/6802* (2013.01); *A61B 5/4815* (2013.01); *A61B 2503/12* (2013.01); *A61B 2505/07* (2013.01); *A61B 5/6826* (2013.01); *A61B 5/14551* (2013.01); *A61B 5/165* (2013.01); *A61B 2503/40* (2013.01); *A61B 5/002* (2013.01); *A61B 2503/10* (2013.01); *A61B 5/164* (2013.01)
  USPC .......................................... 600/481; 600/476

(58) Field of Classification Search
  USPC .......................... 600/301, 481, 483, 500–504
  See application file for complete search history.

(56) References Cited

U.S. PATENT DOCUMENTS 6,155,983 A    12/2000  Kosuda et al.
6,241,684 B1   6/2001   Amano et al.
  (Continued)

FOREIGN PATENT DOCUMENTS

JP   10-258038   9/1998
JP   2001-046345 2/2001
  (Continued)

*Primary Examiner* — Navin Natnithithadha
(74) *Attorney, Agent, or Firm* — Fish & Richardson P.C.

(57) ABSTRACT

A wireless plethysmogram sensor unit is capable of obtaining a plethysmogram from a living tissue of a measuring object and of transmitting the plethysmogram to a processing unit outside the wireless plethysmogram sensor unit. The sensor unit includes a light source to emit measuring light into the living tissue and a light receiving element to receive light emerging from the tissue, which is accompanied by pulsation caused by absorption by arteries in the tissue. A memory stores a plethysmogram obtained in accordance with the light received by the light receiving element. A short range wireless communicator transmits the plethysmogram to the processing unit. A power source provides power to other elements in the sensor unit, and a controller controls the elements of the sensor unit.

12 Claims, 42 Drawing Sheets

(56) References Cited

U.S. PATENT DOCUMENTS

| | | | |
|---|---|---|---|
| 6,608,562 B1 * | 8/2003 | Kimura et al. | 340/573.1 |
| 2001/0049471 A1 | 12/2001 | Suzuki et al. | |
| 2003/0158486 A1 | 8/2003 | Nakashima et al. | |
| 2003/0166994 A1 | 9/2003 | Ooshima et al. | |
| 2003/0181817 A1 | 9/2003 | Mori | |
| 2003/0194205 A1 | 10/2003 | Suzuki et al. | |
| 2003/0195398 A1 | 10/2003 | Suzuki et al. | |
| 2003/0204132 A1 | 10/2003 | Suzuki et al. | |
| 2004/0171918 A1 | 9/2004 | Suzuki et al. | |
| 2004/0236233 A1 | 11/2004 | Kosuda et al. | |
| 2005/0038327 A1 | 2/2005 | Tanaka et al. | |
| 2005/0075553 A1 | 4/2005 | Sakai et al. | |
| 2008/0208016 A1 | 8/2008 | Hughes et al. | |
| 2009/0240125 A1 * | 9/2009 | Such et al. | 600/323 |
| 2009/0247885 A1 | 10/2009 | Suzuki et al. | |
| 2009/0281400 A1 * | 11/2009 | McCraty et al. | 600/301 |
| 2012/0022382 A1 | 1/2012 | Daisuke et al. | |

FOREIGN PATENT DOCUMENTS

| | | |
|---|---|---|
| JP | 2001-344352 | 12/2001 |
| JP | 2002-172094 | 6/2002 |
| JP | 2002-251686 | 9/2002 |
| JP | 2003-024622 | 1/2003 |
| JP | 2003-220052 | 8/2003 |
| JP | 2003-240716 | 8/2003 |
| JP | 2003-275183 | 9/2003 |
| JP | 2004-113821 | 4/2004 |
| JP | 2004-223045 | 8/2004 |
| JP | 2004-275272 | 10/2004 |
| JP | 2004-283228 | 10/2004 |
| JP | 2004-351184 | 12/2004 |
| JP | 2005-110920 | 4/2005 |
| JP | 2006-141902 | 6/2006 |
| JP | 2006-170751 | 6/2006 |
| JP | 2006-296700 | 11/2006 |
| JP | 2009-226167 | 10/2009 |
| JP | 2010-518914 | 6/2010 |
| JP | 2010-148729 | 7/2010 |
| JP | 2012-019811 | 2/2012 |
| JP | 2012-019882 | 2/2012 |
| WO | 02/62222 | 8/2002 |
| WO | 03/096892 | 11/2003 |
| WO | 2009/001449 | 12/2008 |

\* cited by examiner

FIG.37

| BLOOD VESSEL AGE RANKING CHART ||| 
|---|---|---|
| RANK | PLAYER NAME | BLOOD VESSEL AGE |
| 1 | aaa | 15 |
| 1 | bbb | 15 |
| 1 | ccc | 15 |
| 4 | ddd | 16 |
| 4 | eee | 16 |
| 6 | fff | 17 |
| ⋮ | ⋮ | ⋮ |

FIG.39

|  | CHARACTER-X | CHARACTER-Y | CHARACTER-Z |
|---|---|---|---|
| AGITATED PLAYER (PULSE RATE: HIGH) | GENERATED (REGISTERED) | 1ST ATTRIBUTE (PERSONALITY) | 1ST FORM |
| CALM PLAYER (PULSE RATE: LOW) | NOT GENERATED (NOT REGISTERED) | 2ND ATTRIBUTE (PERSONALITY) | 2ND FORM |

WIRELESS PLETHYSMOGRAM SENSOR UNIT, A PROCESSING UNIT FOR PLETHYSMOGRAM AND A PLETHYSMOGRAM SYSTEM

CROSS-REFERENCE TO RELATED APPLICATIONS

The present application is based upon the following Japanese Patent Applications, the entire contents of which are incorporated herein by reference.
(1) Japanese Patent Application No. 2010-157479 (Filing Date: Jul. 12, 2010)
(2) Japanese Patent Application No. 2010-158911 (Filing Date: Jul. 13, 2010)
(3) Japanese Patent Application No. 2010-203782 (Filing Date: Sep. 10, 2010)
(4) Japanese Patent Application No. 2010-210739 (Filing Date: Sep. 21, 2010)
(5) Japanese Patent Application No. 2010-229782 (Filing Date: Oct. 12, 2010)
(6) Japanese Patent Application No. 2010-245049 (Filing Date: Nov. 1, 2010)
(7) Japanese Patent Application No. 2010-245894 (Filing Date: Nov. 2, 2010)

BACKGROUND OF THE INVENTION

1. Field of the Invention

The present invention relates to a plethysmogram sensor unit, a processing unit for a plethysmogram, and a plethysmogram system.

2. Description of the Related Art

Various biometric information measurement devices have been proposed in the past, one of which being a plethysmogram measurement device.

There have also been various proposals related to the practical use of biometric information obtained through measurements. Examples of proposals include measuring the pulse during an activity and feeding the result back to the person engaged in the activity to determine physical stamina. A variety of monitoring systems have also been studied in recent years for elderly persons living alone, given the advent of an aging society, and proposals have been made to monitor these persons by detecting pulse abnormalities (e.g., International Laid-open Patent Publication No. WO2003/096892). In relation to such systems there has also been proposed a daily activity monitoring system provided with transmitting means for transmitting, via email, signals outputted by daily activity information detecting means (Japanese Laid-open Patent Publication No. 2002-251686).

There has also been proposed a biometric information measuring system which includes a measurement device terminal, a mobile telephone, and a processing center (e.g., International Laid-open Patent Publication No. WO2002/062222). According to this proposal, the measurement device terminal has a measurement unit for measuring biometric information, an adapter for obtaining a telephone number from a mobile telephone to identify a mobile telephone, and transceiving means for linking and outputting biometric information and telephone numbers with each other. The mobile telephone also stores a telephone number to identify the users themselves. The processing center has storing means for storing a database linking the names, and other data of users using mobile telephones to telephone numbers, and storing, for each user, biometric information from the measurement device terminal; and processing means for identifying the user of a mobile telephone based on the telephone number and the database.

However, there remain unexamined a variety problems related to the measurement of biometric information, the processing of biometric information, and biometric information systems.

SUMMARY OF THE INVENTION

According to an embodiment of the present invention, a useful plethysmogram sensor is proposed for various objects. According to an embodiment of the present invention, a useful processing unit for a plethysmogram is proposed for various objects. According to an embodiment of the present invention, a useful plethysmogram system is provided for various objects.

According to an embodiment of the present invention, there is provided a wireless plethysmogram sensor unit capable of obtaining a plethysmogram from a living tissue of a measuring object and transmitting the obtained plethysmogram to a processing unit outside the wireless plethysmogram sensor unit. The wireless plethysmogram sensor unit comprises: a light source provided inside the wireless plethysmogram sensor unit and arranged to emit measuring light into living tissue; a light receiving element provided inside the wireless plethysmogram sensor unit and arranged to receive light emerging from the living tissue which is the measuring light in origin and accompanied with pulsation caused by absorption by arteries in the living tissue; a memory provided inside the wireless plethysmogram sensor unit and arranged to store a plethysmogram obtained in accordance with the light received by the light receiving element; a short range wireless communicator provided inside the wireless plethysmogram sensor unit and arranged to transmit a plethysmogram stored in the memory to the processing unit; a power source provided inside the wireless plethysmogram sensor unit to power the elements provided inside the wireless plethysmogram sensor unit; and a controller provided inside the wireless plethysmogram sensor unit and arranged to control the elements provided inside the wireless plethysmogram sensor unit.

In the wireless plethysmogram sensor according to an embodiment of the present invention, for example, the plethysmogram is of a human being and utilized to monitor a training approach in a gym, to confirm the safety of a solitary life, and/or to condition the progress of an amusement device, to which the human being relates.

According to an embodiment of the present invention, a processing unit capable of receiving a plethysmogram from a plurality of outside plethysmogram sensor units is provided, the plethysmogram being a measurement of living tissue in a measuring object. The processing unit comprises: a communicator arranged to receive the plethysmogram from one of the plethysmogram sensor units; and a processor arranged to process the received plethysmogram.

According to an embodiment of the present invention, a plethysmogram system is provided, the plethysmogram system comprising: a plethysmogram sensor unit capable of obtaining a plethysmogram of living tissue in a human being; and a controller arranged to utilize the obtained plethysmogram for conditioning the progress of an amusement device, to which the human being relates.

Further technical aspects, elements, steps, advantages, and characteristics of the present invention will become apparent from the detailed description of preferred embodiments and the appended drawings related thereto given below.

BRIEF DESCRIPTION OF THE DRAWINGS

FIG. 37 is a diagram used to describe the fifth application for pulse wave information in Example 11;

FIG. 39 is a diagram used to describe the seventh application for pulse wave information in Example 11;

DETAILED DESCRIPTION OF PREFERRED EMBODIMENTS

Example 1

Figure 1:
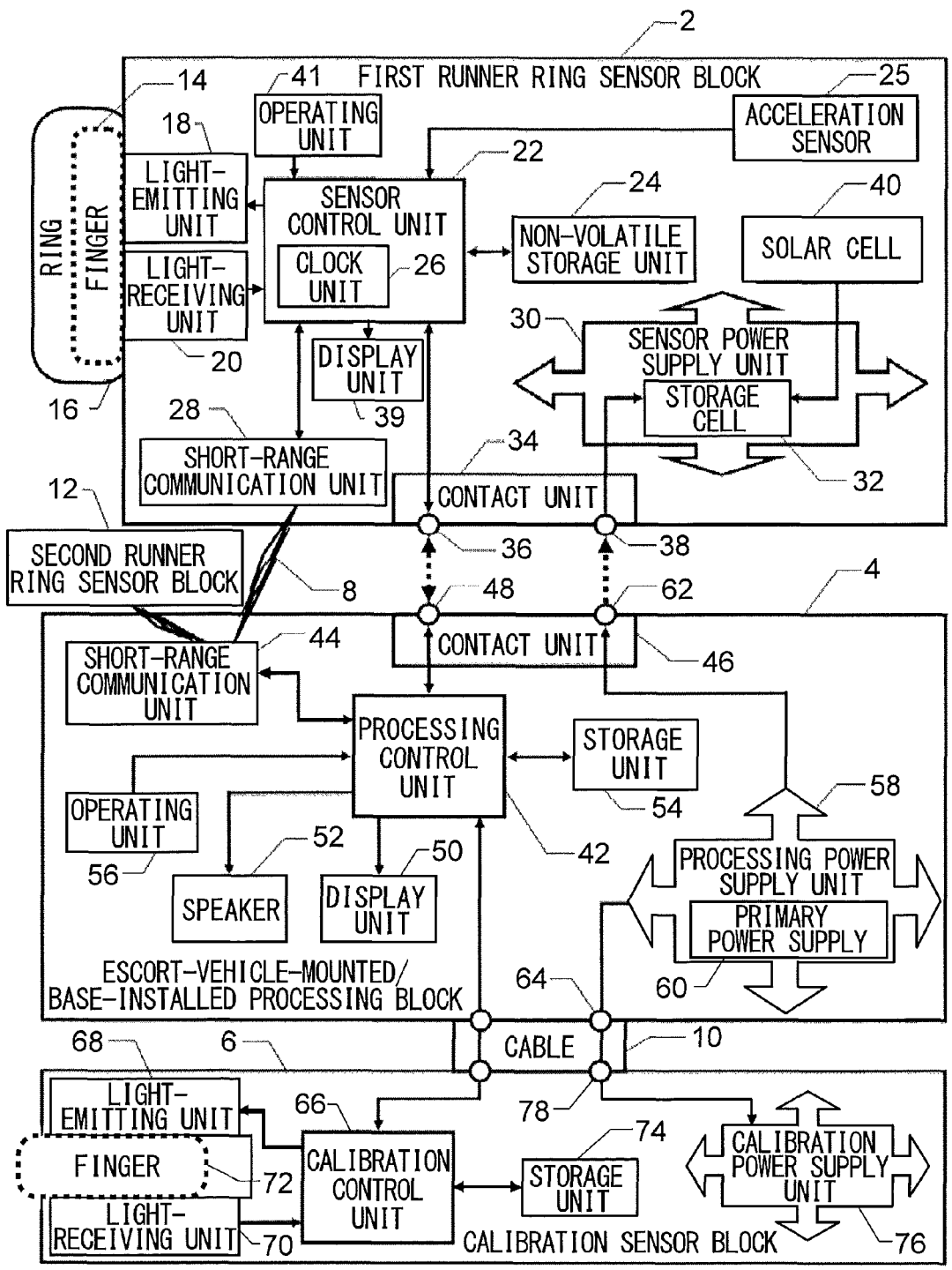
FIG. 1 is a block diagram showing Example 1 of the present invention configured as a biometric information measurement device.

FIG. 1 is a block diagram showing Example 1 of the present invention configured as a biometric information measurement device according to an embodiment of the present invention. Example 1 has general features applicable to monitoring systems in addition to biometric information measurements for healthcare. In these respects, the present example is similar to the examples below. Example 1 is configured as a biometric information measuring system which can use pulse waves and the pulse of a runner during running to measure oxygen saturation. The minimum units include a first runner ring sensor block 2 that can be placed over a finger of a first runner, a biometric information processing block 4 (referred to below as "escort-vehicle-mounted/base-installed processing block 4") installed in a vehicle escorting the first runner while running, or in a base station such as a water supply point or corner of a track passed by the first runner, and a calibration sensor block 6 for calibrating the output from the first runner ring sensor block 2. The first runner ring sensor block 2 and the escort-vehicle-mounted/base-installed processing block 4 are able to communicate wirelessly at short range via radio waves 8, and the calibration sensor block 6 can be connected to the escort-vehicle-mounted/base-installed processing block 4 via a cable 10.

The escort-vehicle-mounted/base-installed processing block 4 is able to process biometric information from a plurality of runners. For example, it conducts short-range wireless communication with a second runner ring sensor block 2. Because the configuration of the second runner ring sensor block 12 is similar to the first runner ring sensor block 2, illustration of the internal configuration has been omitted in FIG. 1. Also, for the sake of simplicity, only the first runner ring sensor block 2 and the second runner ring sensor block 12 are shown in FIG. 1. However, the escort-vehicle-mounted/base-installed processing block 4 can communicate with similarly configured runner ring sensor blocks placed over the fingers of a plurality of runners, and can obtain biometric information from these runners.

The calibration of the runner ring sensor blocks is performed for each runner. For example, the first runner ring sensor block 2 is attached to the finger of the first runner to be subject to measurement, and the calibration sensor block 6 is attached to the same finger of the first runner and a measurement is simultaneously performed. The calibration of the second runner ring sensor block 12 and the other runner ring sensor blocks is performed in the same manner on the second runner and the other runners to be subject to measurement.

The following is a description of the configuration of the runner ring sensor block, using the first runner ring sensor block 2 as the example. The overall size and weight of the first runner ring sensor block 2 is similar to a ring. When the first runner ring sensor block 2 is attached to a finger 14 by the ring 16 attached around the finger 14, a light-emitting unit 18 and a light-receiving unit 20 make contact on the surface of the finger 14 on the same side as the back of the hand. The light-emitting unit 18 includes a plurality of light-emitting diodes provided concentrically on the outer periphery of the light-receiving unit 20, and the light-receiving unit 20 commonly receives the light emitted from the plurality of light-emitting diodes and reflected by the finger tissue while being absorbed by the blood inside the finger 14. This configuration is suited to arranging the relative positions of the light-emitting unit 18 and the light-receiving unit 20 for high precision and to be simple and compact. In this configuration, light of such a wavelength that it is incident on one side of the finger 14 and cannot exit from the opposite side can be used in the measurement.

When the light-emitting unit 18 and the light-receiving unit 20 are configured as a pulse oximeter able to measure pulse waves and oxygen saturation, the light-emitting unit 18 includes at least two pairs of light-emitting diodes centered on the finger 14 and installed on the opposite side with respect to the light-receiving unit 20. One pair has an output peak at a wavelength with an absorbance near oxygenated hemoglobin and reduced hemoglobin, and the other pair has an output peak at a wavelength different from the absorbance of oxygenated hemoglobin and reduced hemoglobin. When light-emitting diodes of different wavelengths are used in this manner, the light emission timing is time-divided so that light at the respective wavelengths is separated and received by a common light-receiving unit 20 using, for example, a photodiode having light-receiving sensitivity at all light emission wavelengths. The light-emitting diodes having the same wavelength can emit light simultaneously. However, because measurement conditions vary depending on the position, the emission can also be time-divided to locate the light-emitting diode with the optimum conditions. Measurements are thereby conducted based on the output from the light-emitting diode with the optimum conditions.

When pulse waves and the pulse are measured without measuring the oxygen saturation, a blue light-emitting diode can be used as the light-emitting unit 18. However, in order to take advantage of the available wavelengths, the emission of a plurality of light-emitting diodes with different output wavelengths can be time-divided, to locate the light-emitting diode with the optimum wavelength based on personal differences, and output from this diode can be used in the measurements. There are no particular restrictions on the configuration of the light-emitting unit 18 and the light-receiving unit 20. A variety of configurations can be devised to measure a target making sudden movements such as a runner.

The sensor control unit 22 controlling the entire first runner ring sensor block 2 controls the light emission timing for the light-emitting unit 18, receives output from the light-receiving unit 20, processes the output, and stores the processed output in a non-volatile storage unit 24 as biometric information such as pulse waves, pulse, oxygen saturation, and the like. Because an acceleration sensor 25 detects the acceleration of the first runner ring sensor block 2, it has two primary functions. The first function is to detect the state of the first runner. In other words, it identifies whether the first runner is in a resting state or a running state. When the runner is in a running state, it identifies whether the runner is running slowly or sprinting. This identification information is added to the biometric information.

The second function is to eliminate the adverse effects of vibrations from running on the measurement. The sensor control unit 22 corrects the measurement information from the light-receiving unit 20 based on the acceleration information detected by the acceleration sensor 25, and discards from the measurement information the output from the light-receiving unit 20 when excessive acceleration reduces the reliability of the measurement information. The biometric information stored in the non-volatile storage unit 24 is processed while taking into account information from the acceleration sensor 25. The sensor control unit 22 also has a clock unit 26, which adds a clock stamp to the biometric information stored in the non-volatile storage unit 24 when biometric information is obtained. The non-volatile storage unit 24 stores this biometric information, the operating program for the sensor control unit 22, and temporary data required for operation.

When it is able to conduct short-range communication with the escort-vehicle-mounted/base-installed processing block 4, the short-range communication unit 28 in the first runner ring sensor block 2 retrieves biometric information from the non-volatile storage unit 24 and transmits the information. A sensor power supply unit 30 has a storage cell 32 and supplies power having the predetermined voltage to the various components in the first runner ring sensor block 2. A contact unit 34 such as a universal serial bus (USB) is used to connect the first runner ring sensor block 2 removed from the finger 14 of the first runner to the escort-vehicle-mounted/base-installed processing block 4 before the start of measurements as well as afterward.

Establishing a connection via the contact unit 34 enables the first runner ring sensor block 2 to communicate in a wired manner with the escort-vehicle-mounted/base-installed processing block 4 via a contact 36, and various types of information can be exchanged for linking purposes. When there is biometric information that cannot be transmitted by the short-range communication unit 28, it is retrieved from the non-volatile storage unit 24 and transmitted all at once. Establishing a connection via the contact unit 34 enables the storage cell 32 in the sensor power supply unit 30 to be charged from the escort-vehicle-mounted/base-installed processing block 4 via a contact 38 in the contact unit 34. Establishing a connection to the escort-vehicle-mounted/base-installed processing block 4 in order to charge the first runner ring sensor block 2 makes it possible for the biometric information remaining in the non-volatile storage unit 24 to be collected by the escort-vehicle-mounted/base-installed processing block 4 without any data loss. The solar cell 40 can be used to perform supplemental charging of the storage cell 32 when the first runner ring sensor block 2 has been separated from the escort-vehicle-mounted/base-installed processing block 4 and attached to the finger 14 of the first runner, such as while running.

The functions of the first runner ring sensor block 2 are started by turning on the power switch in the operating unit 41. The functions are stopped by turning off this power switch. The sensor control unit 22 automatically stops the functions of the first runner ring sensor block 2 when it has been detected that the output from the light-receiving unit 20 has not changed over a predetermined period of time. This prevents wasteful consumption of the storage cell 32. The automatic stopping function can be reset by turning on the power switch in the operating unit 41. The display unit 39 displays a minimal amount of information such as the operating status of the first runner ring sensor block 2 and whether the device is properly attached to the finger 14.

The processing control unit 42 in the escort-vehicle-mounted/base-installed processing block 4 processes radio waves 8 received by the short-range communication unit 44 or biometric information received from the first runner ring sensor block 2 inputted over a cable via a contact 48 in a contact unit 46. It also performs processing to judge and display the state of the first runner based on the biometric information. The state of the runner can be judged automatically, for example, by comparing the biometric information to a typical pulse pattern determined in advance. The processing results are displayed by a display unit 50 or announced over a speaker 52. The processing results are also stored in a storage unit 54 as a history of biometric information. The biometric information history is stored in chronological order for each person based on the time stamps when the biometric information was received and based on the runner ID. The biometric information stored in the storage unit 54 is statistically processed and averaged for each individual and for all runners, and the results are displayed or announced by the display unit 50 or the speaker 52. The storage unit 54 stores this biometric information, the operating program for the processing control unit 42, and temporary data required for operation.

The operating unit 56 is used to input a variety of settings or input instructions for the variety of types of processing and for the displaying and announcing. A processing power supply unit 58 has a primary power supply 60 from a large storage battery or a power line. Power of a predetermined voltage is thereby supplied to the various components in the escort-vehicle-mounted/base-installed processing block 4. The processing power supply unit 58 supplies charging power to the first runner ring sensor block 2 connected to the contact unit 46 via a contact 62, and supplies power to the calibration sensor block 6 connected to a cable 10 via a contact 64.

The calibration sensor block 6 is controlled by a calibration control unit 66. During calibration, as has already been described, the first runner ring sensor block 2 is attached to a finger 14 of the first runner subject to measurement, another finger 72 of the first runner is placed between a light-emitting unit 68 and a light-receiving unit 70 of the calibration sensor block 6, and linking between the sensor control unit 22 and the calibration control unit 66 via radio waves 8 and the cable 10 under the control of the processing control unit 42, whereby simultaneous measurements are performed. This calibration can be performed, for example, with the first runner seated beside the escort-vehicle-mounted/base-installed processing block 4. The measurement results from the first runner ring sensor block 2 are compared to the measurement results from the calibration sensor block 6 used for reference purposes, and the calibration data is stored in the storage unit 54 or the non-volatile storage unit 24. A storage unit 74 in the calibration sensor block 6 is used to store the operating program for the calibration control unit 66, and temporary data required for operation. A calibration power supply unit 76 receives power from the primary power supply 60 in the escort-vehicle-mounted/base-installed processing block 4 via a contact 78 connected to the cable 10, and supplies power having a predetermined voltage to the various components in the calibration sensor block 6.

In the description related to Example 1, the subject of measurement is a runner. However, the subject of the configuration in Example 1 does not have to be a runner. Biometric information can be advantageously obtained, analyzed, and processed statistically from persons in a location where people are engaged in a wide variety of physical activities such as a fitness center or sports gym. Here, the escort-vehicle-mounted/base-installed processing block 4 can be installed in a training room at the sports gym or athletic center.

Figure 2:
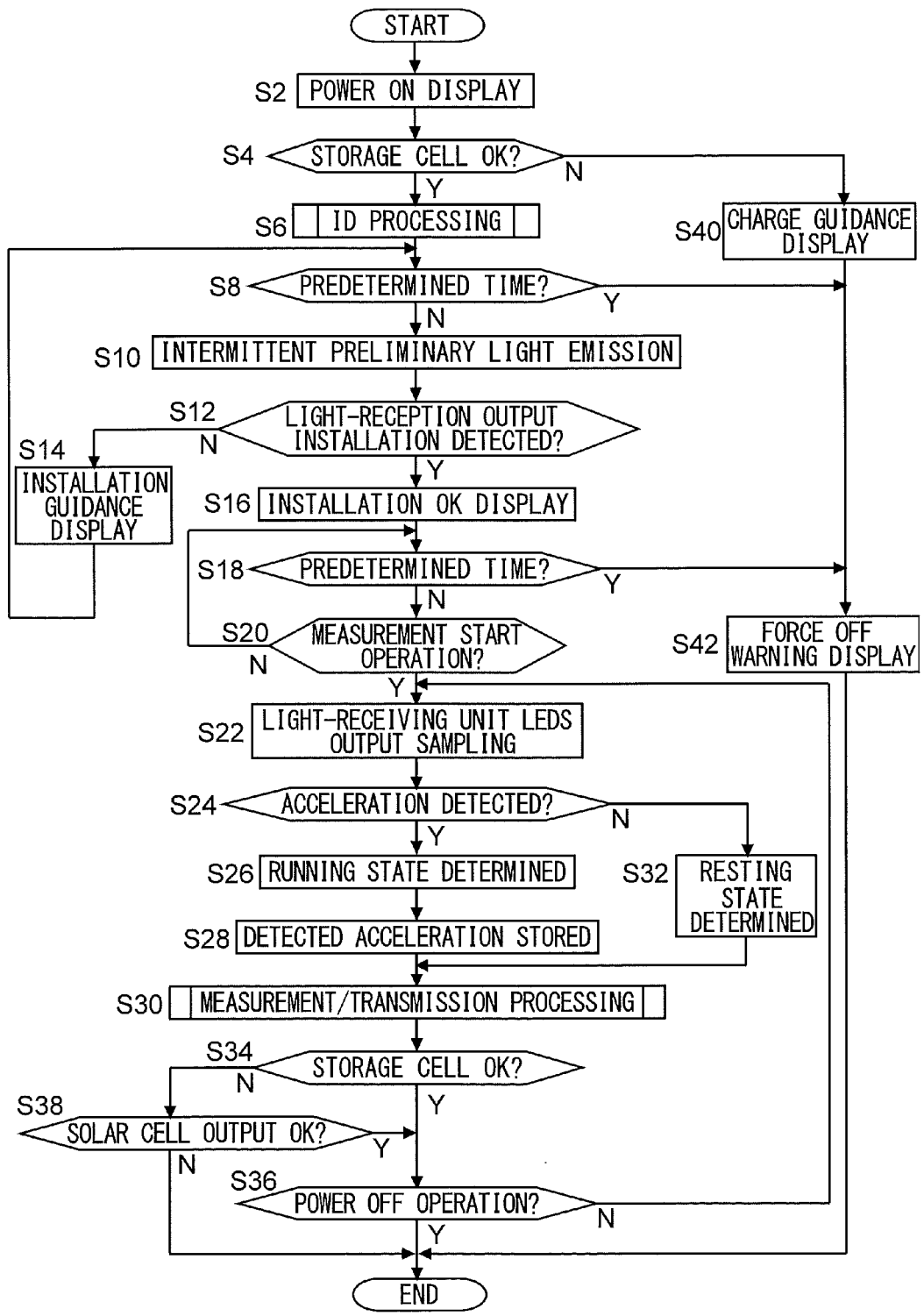
FIG. 2 is a flowchart showing the action of the sensor control unit in Example 1.

FIG. 2 is a flowchart showing the operation of the sensor control unit 22 in Example 1 of FIG. 1. The flow starts when the power switch in the operating unit 41 is turned on. In Step S2, an instruction is issued to display the power ON status on the display unit 39. In Step S4, a check is made as to whether or not the charge of the storage cell 32 is sufficient. When sufficient, the flow moves to the ID process in Step S6, and processing is performed to register the ID of the first runner ring sensor block 2 and the personal ID of the first runner, or the like. A detailed description is provided below.

When the ID process in Step S6 has been completed, a check is made in Step S8 as to whether or not a predetermined period of time has elapsed since the power was turned on. When the period of time has elapsed, an instruction is issued for intermittent preliminary light emission of the light-emitting unit 18 in Step S10, and the flow advances to Step S12. In Step S12, a check is made as to whether or not the first runner ring sensor block 2 has been attached to a finger 14 based on the output from the light-receiving unit 20. When attachment has not been detected, the flow advances to Step S14. An instruction is issued to display attachment guidance on the display unit 39, and the flow returns to Step S8. Subsequently, the flow from Step S8 to Step S14 is repeated and the process stands by for attachment to a finger until it is detected at Step S8 that the predetermined amount of time has elapsed, or until a check is made at Step S12 that the block has been attached to the finger 14. Here, the light-emitting unit 18 and the light-receiving unit 20 used in the measurement process are used to check whether or not the block has been attached to a finger. Unlike the measurement process, light emission from the light-emitting unit 18 used to detect whether the block has been attached to a finger is intermittent in order to conserve power.

The flow advances to Step S16 when it has been detected from the light-reception output that the block has been attached to the finger 14 in Step S12. An instruction is issued to display "attached" on the display unit 39, and the flow advances to Step S18. At this time, in combination with Step S16, the escort-vehicle-mounted/base-installed processing block 4 is notified via a communication that the block has been attached. In Step S18, a check is made as to whether or not a predetermined period of time has elapsed since attachment to the finger 14 has been detected. If the predetermined period of time has not elapsed, the flow advances to Step S20 where a check is made as to whether or not the measurement startup operation has been performed using the operating unit 41. If the measurement startup operation has not been detected, the flow returns to Step S18. Step S18 and Step S20 are repeated to await the measurement startup operation until the predetermined period of time has elapsed.

When the measurement startup operation has been detected in Step S20, the flow advances to Step S22, and the output from the light-receiving unit 20 is sampled based on the time-divided light emission from the plurality of LEDs in the light-emitting unit 18. The flow then advances to Step S24 where the output from the acceleration sensor 25 during sampling is checked to determine whether or not acceleration has been detected, and a check is made as to whether or not the acceleration has been detected. When acceleration has been detected, the flow advances to Step S26 where it is determined whether the runner is in a running state and whether the runner is running slowly or sprinting. The flow then proceeds to Step S28 where the acceleration detected in Step S24 is stored. The flow then advances to Step S30. If acceleration has not been detected in Step S24, the flow advances to Step S32. When a resting state has been determined, the flow advances to Step S30. In Step S30, the measuring process is performed based on the output sampled in Step S22 and based on the acceleration detected in Step S24, and the measurement results are transmitted. A description is given in further detail below.

When the measurement/transmission process has been completed in Step S30, the flow advances to Step S34 where a check is made as to whether the charge of the storage cell 32 is sufficient. If it is sufficient, the flow advances to Step S36 where a check is made as to whether the power switch has been turned off using the operating unit 41. If it has been judged in Step S34 that the charge of the storage cell is insufficient, the flow advances to Step S38 where a check is made as to whether sufficient output can be obtained from the solar cell 40 to continue the measurement process. When the output is sufficient, a check is made in Step S36 as to whether or not the power switch has been turned off. In either case, the flow returns to Step S22 if it has not been detected in Step S36 that the power switch has been turned off.

The flow from Step S22 to Step S38 is repeated and the measurement process continued until it has been detected in Step S36 that the power switch has been turned off. Here, one sampling is performed in Step S22 with respect to the light reception output of the various LEDs whose light emission is time-divided; however, a plurality of samplings can also be performed. In the case of the latter, the samplings are performed to the extent that the pulse wave shape can be identified. This can be determined appropriately based on the time allocated for the flow from Step S22 to Step S38, and based on the resolution of the pulse wave measurements and acceleration detection. The configuration of the steps can be changed where appropriate to achieve the same intended functions.

When it has been detected in Step S36 that the power switch has been turned off, the flow is ended immediately. As a consequence of flow ending, the power supply to the first runner ring sensor block 2 is turned off. At this time, any measurement data that has not been transmitted to the first runner ring sensor block 2 is held in the non-volatile storage unit 24 without consuming power in order to await the next transmission opportunity. When it has been judged in Step S38 that the output from the solar cell is insufficient, the flow is ended immediately, and the power supply to the first runner ring sensor block 2 is turned off. When it has been judged in Step S4 that the charge of the storage cell 32 is insufficient, the flow advances to Step S40, and guidance is displayed on the display unit 39 indicating the need for charging. The flow advances to Step S42, an instruction is given to display a warning on display unit 39 indicating that the power supply will be forcibly turned off, and the flow is ended. When it has been detected in Step S8 that the predetermined period of time has elapsed, or when it has been detected in Step S18 that the predetermined period of time has elapsed, the flow advances to Step S42 where an instruction is similarly given to display a warning indicating that the power supply will be forcibly turned off, and the flow is ended.

Figure 3:
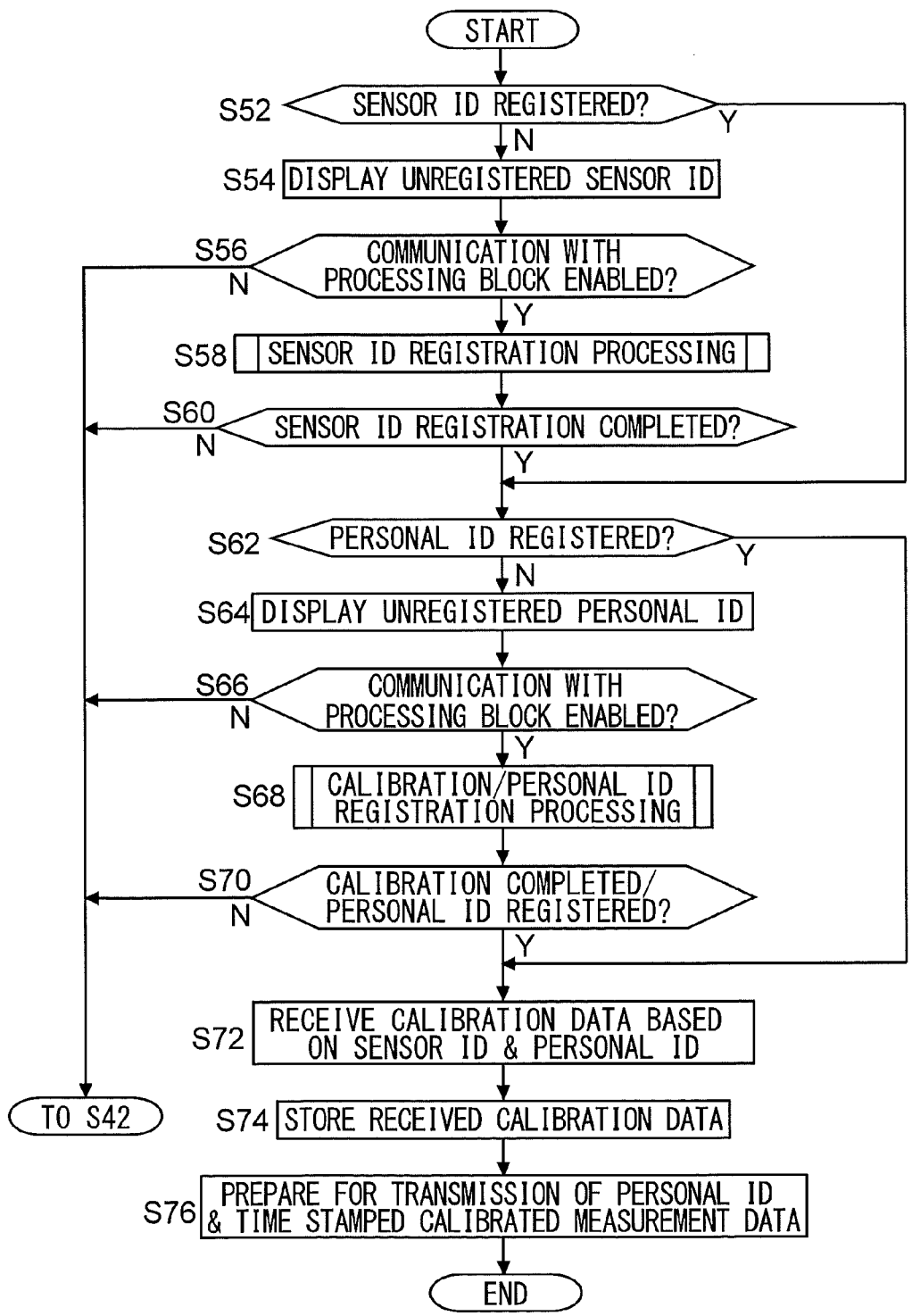
FIG. 3 is a flowchart showing Step S6 in FIG. 2 in greater detail.

FIG. 3 is a flowchart showing the ID process in Step S6 of FIG. 2 in greater detail. When the flow has been started, a check is made in Step S52 as to whether or not the ID of the first runner ring sensor block 2 has been registered in the escort-vehicle-mounted/base-installed processing block 4. If the ID is not registered, the flow advances to Step S54 where a message is displayed on the display unit 39 that the sensor ID is unregistered. A check is then made in Step S56 as to whether or not communication can be established with the escort-vehicle-mounted/base-installed processing block 4. When communication can be established, the flow advances to Step S58 and the sensor ID registration process is performed including transmission of the sensor ID and a registration confirmation signal. If registration cannot be performed in Step S58 due to a problem such as a communication blackout or serious malfunction, the flow advances to Step S60 without being locked and a check is made as to whether or not registration of the sensor ID has been completed. When completion has been confirmed, the flow advances to Step S62. When in Step S52 it has been confirmed that the ID of the first runner ring sensor block 2 has already been registered in the escort-vehicle-mounted/base-installed processing block 4, the flow advances directly to Step S62.

In Step S62, a check is made as to whether or not the calibrated data for the first runner calibrated using the first runner ring sensor block 2 has been registered along with personal ID in the escort-vehicle-mounted/base-installed processing block 4. When unregistered, the flow advances to Step S64 where instructions are provided to display a message on the display unit 39 indicating that the personal ID is unregistered. In Step S66, a check is made as to whether or not communication can be established with the escort-vehicle-mounted/base-installed processing block 4. When communication can be established, the flow advances to Step S68 where calibration/personal ID registration is performed. The calibration/personal ID registration process includes calibration processing on the first runner using the first runner ring sensor block 2, transmission of the calibrated data with the personal ID affixed, and transmission of a registration confirmation signal. As in Step S58, when registration is difficult to perform in Step S68 because of a problem, the flow advances to Step S70 without being locked and a check is made as to whether or not calibration has been completed and whether or not registration of the personal ID accompanying the calibrated data has been completed. When completion has been confirmed, the flow advances to Step S72. When in Step S62 it has been confirmed that the calibrated data for the first runner calibrated using the first runner ring sensor block 2 has been registered along with the personal ID in the escort-vehicle-mounted/base-installed processing block 4, the flow advances directly to Step S72.

Because reaching Step S72 means the sensor ID, personal ID, and calibrated data for the person obtained from the sensor has been registered, calibrated data is received from the escort-vehicle-mounted/base-installed processing block 4 based on the indicated sensor ID and personal ID. The received calibrated data is stored in the non-volatile storage unit 24 in Step S74. Thus, even when a measurement is performed using a sensor with a possibility of variability, measurement data related to the person identified by the same personal ID and calibrated for variability is sent to the escort-vehicle-mounted/base-installed processing block 4. In Step S76, the preparation steps for transmitting calibrated measurement data obtained using measurements performed in this environment and stamped with the personal ID and time are set, and the flow is ended.

The flow advances to Step S42 in FIG. 2 when it has been determined in Step S56 that communication cannot be established with the escort-vehicle-mounted/base-installed processing block 4, when it has been determined in Step S60 that the sensor ID registration is incomplete, when it has been determined that communication cannot be established with the escort-vehicle-mounted/base-installed processing block 4 in Step S66, and when it has been determined in Step S70 that calibration and registration of the personal ID accompanying the calibrated data are incomplete.

Figure 4:
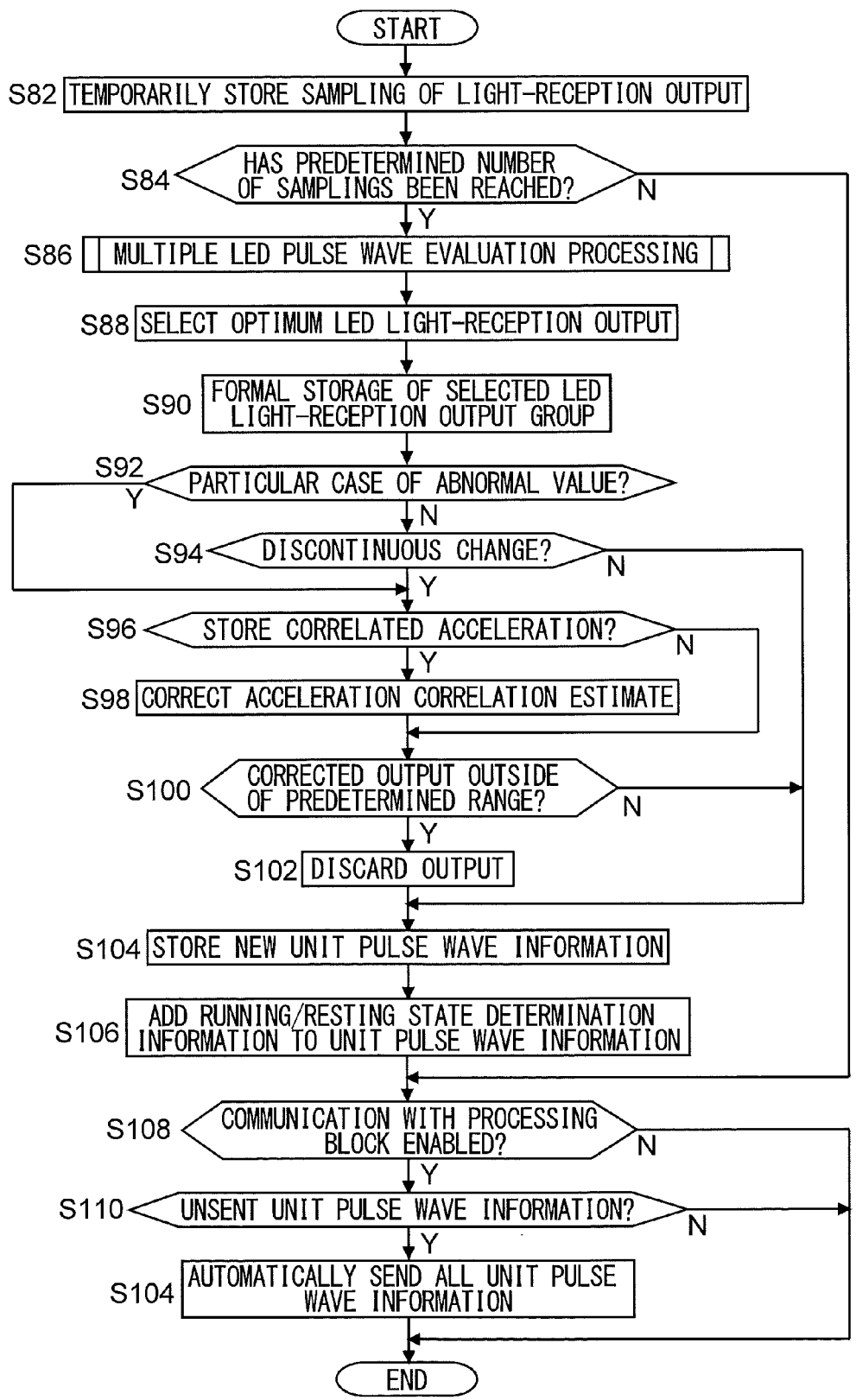
FIG. 4 is a flowchart showing Step S30 in FIG. 2 in greater detail.

FIG. 4 is a flowchart showing the measurement/transmission processing in Step S30 of FIG. 2 in greater detail. When the flow has been started, updated sampling light reception output in which various LEDs with time-divided light emission are used as the light source is temporarily stored in Step S82, and a check is made in Step S84 as to whether or not the cumulative number of samplings has reached a predetermined number. The predetermined number of samplings is a number sufficient for judging the pulse wave shape. When it has been confirmed in Step S84 that the number of samplings has reached the predetermined value, the flow advances to Step S86, and the pulse waves using the various LEDs with time-divided light emission are evaluated. This evaluation is performed based on the relative size and the S/N ratio of the output. In Step S88, light reception output using the optimum LEDs as the light source is selected based on this evaluation, and in Step S90 the selected LED output group is formally stored in the non-volatile storage unit 24 as pulse wave information.

Next, in Step S92, a check is made as to whether there are any unlikely abnormal values in the sampling output that was formally stored. When it has been verified that there are none, a check is made in Step S94 as to whether or not there are unlikely discontinuous changes in the sampling output. When there are discontinuous changes, the flow advances to Step S96. When a particular case of an abnormal value has been detected in Step S92, the flow advances directly to Step S96. In Step S96, a check is made as to whether or not an acceleration pattern having a correlation known to be caused by these abnormal values or discontinuities has been stored. When such a pattern has been determined, the flow advances to Step S98 where the original measurement values are estimated from the acceleration correlation, and the abnormal values or discontinuities are corrected. The flow then proceeds to Step S100. When the storing of correlated acceleration has not been detected in Step S96, the flow advances directly to Step S100.

In Step S100, a check is made as to whether or not the corrected output obtained above (including uncorrected output) falls outside of a predetermined range. When it falls outside of this range, the flow advances to Step S102. The output is discarded, and the flow advances to Step S104. When it has not been detected in Step S100 that the corrected output is outside of the predetermined range, the flow advances directly to Step S104. When discontinuous changes have not been detected in Step S94, the flow advances directly to Step S104. In Step S104, new light reception output from the predetermined number of samplings processed in the manner described above (referred to as "unit pulse wave information) is stored. In Step S106, information indicating whether the runner is in a running state or resting state is affixed to the unit pulse wave information, and the flow advances to Step S108. When it has not been detected in Step S84 that the number of samplings has reached the predetermined value, the number of sampling of output is not yet sufficient form unit pulse wave information. Thus, the flow advances directly to Step S108.

In Step S108, a check is made as to whether or not communication can be established with the escort-vehicle-mounted/base-installed processing block 4. When communication can be established, a check is made in Step S110 as to whether or not there is any unsent unit pulse wave information. When there is unsent unit pulse wave information, the flow advances to Step S112 where the information is automatically transmitted all at once and the flow is ended. When it cannot be detected in Step S108 that communication can be established or when it has been judged in Step S110 that there is no unsent unit pulse wave information, the flow is immediately ended.

Example 2

Figure 5:
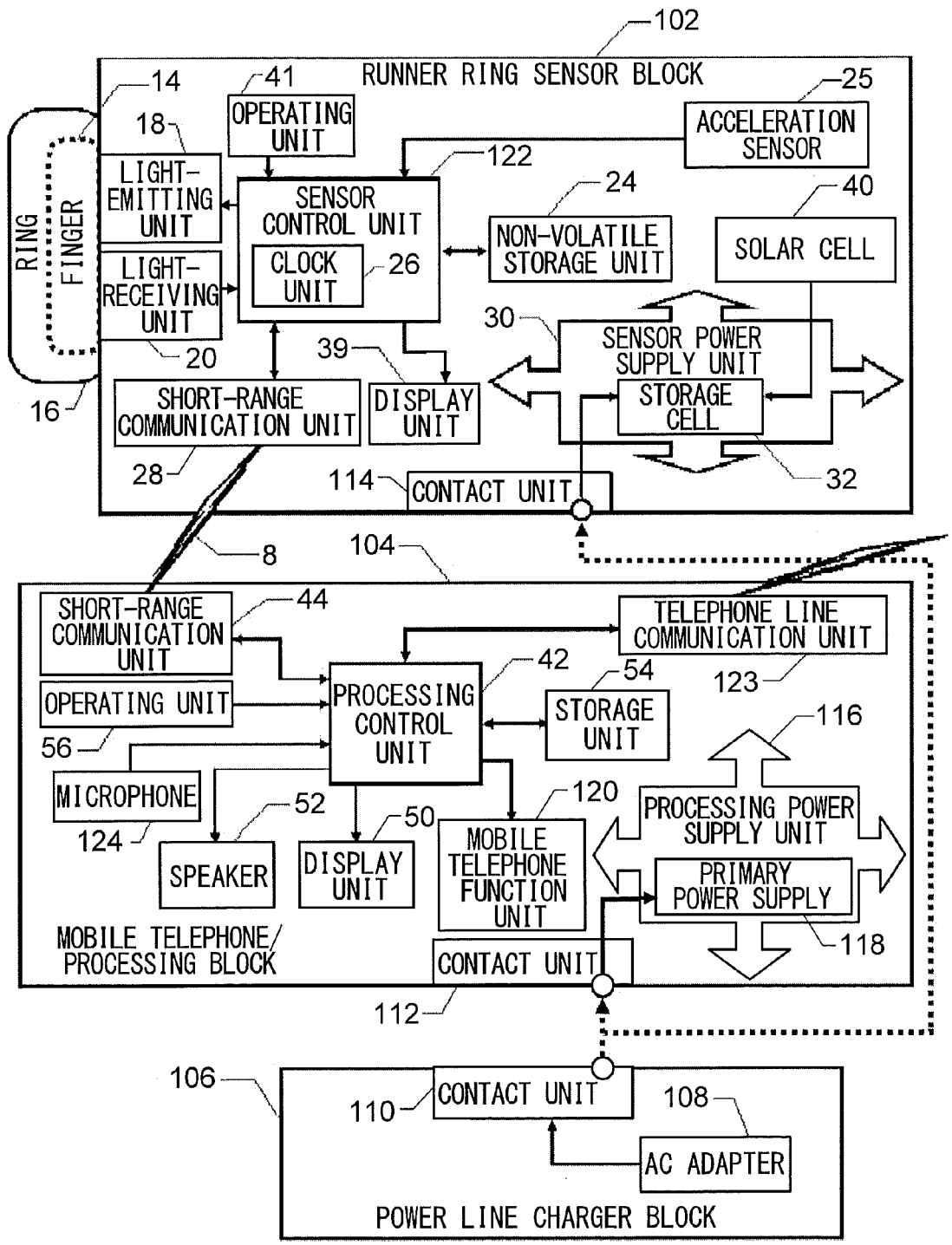
FIG. 5 is a block diagram showing Example 2 of the present invention configured as a biometric information measurement device.

FIG. 5 is a block diagram showing Example 2 of the present invention configured as a biometric information measurement device according to an embodiment of the present invention. As in the case of Example 1, Example 2 is configured from a biometric information measuring system able to measure oxygen saturation using the pulse waves and pulse of a runner while running. The primary structural elements are a runner ring sensor block 102 that can be attached to a finger 14 of the runner, and a mobile telephone 104 able to establish short-range wireless communication. Because the mobile telephone 104 functions as a processing block for the biometric information received from the runner ring sensor block 102, it is referred to below as the "mobile telephone/processing block 104." The biometric information measuring system in Example 2 includes a power line charger block 106 for charging a storage cell 118 in the mobile telephone/processing block 104. The power line charger block 106 has a configuration similar to a charger of an ordinary mobile telephone. Power from an alternating current power line is converted to direct current of a predetermined voltage via an AC adapter 108, and then outputted from the charging contact unit 110. The power line charger block is also used as the charger for the storage cell 32 in the runner ring sensor block 102.

Most of the configuration in Example 2 is similar to Example 1. The components similar to those in Example 1 are denoted by the same numbers, and further description of these components has been omitted. The following description will focus on the differences. The runner ring sensor block 102 in Example 2 is not connected to the mobile telephone/processing block 104 for wired communication and charging. Instead, it has a charging contact unit 114 with the same contact shape, rated current, and rated voltage as a charging contact unit 112 on the mobile telephone/processing block 104. When the storage cell 118 in a processing power supply unit 116 of the mobile telephone/processing block 104 is charged, the storage cell 32 can be charged by connecting the charging contact unit 114 to the charging contact unit 110 in the power line charger block 106.

The mobile telephone/processing block 104 has a mobile telephone function unit 120 and a telephone line communication unit 123 for providing the functions needed to conduct ordinary telephone calls. It also has a speaker 52 and a microphone 124 for conducting telephone calls. In this configuration, biometric information is transmitted from the runner ring sensor block 102 to the mobile telephone/processing block 104 in Example 2 via the exchange of radio waves 8 between the short-range communication unit 28 and the short-range communication unit 44. The biometric information received and processed by the mobile telephone/processing block 104 can be transmitted to a personal physician via the mobile telephone function unit 120 and the telephone line communication unit 123. This can be set so that biometric information is automatically transmitted as soon as it is obtained.

As in Example 1, an operating unit 41 is provided in the runner ring sensor block 102 of Example 2. This is primarily used to turn on and off the power supply, and the various operations for obtaining biometric information are performed centrally by operating the operating the operating unit 56 in the mobile telephone/processing block 104. The various screens related to obtaining biometric information using these operations are primarily displayed on the display unit 50 of the mobile telephone/processing block 104. The display unit 39 in the runner ring sensor block 102 has only limited display functions including displaying the on/off status. Thus, the runner ring sensor block 102 functions as a mobile-telephone sensor accessory having a biometric information obtaining function serving as an application. Most of the operations and displays related to obtaining biometric information are centrally managed on the mobile telephone/processing block 104 side. Thus, instructions to obtain and transmit biometric information are performed on the mobile telephone/processing block 104 side.

Most of the functions for the sensor control unit 122 in Example 2 can be executed in accordance with the flowchart of Example 1 shown in FIG. 2. The following description will focus on the different components. First, in Example 2, when the runner ring sensor block 102 is used with a privately owned mobile telephone/processing block 104, the ID processing in Step S6 can be omitted. When, as in Example 1, runner ring sensor blocks are attached to the fingers of a plurality of runners, and a coach accompanying the runners is holding a mobile telephone/processing block 104, the ID process in Step S6 can be utilized.

In Example 2, "display" in Steps S14, S16, S40, and S42 of the flowchart in FIG. 2 can be understood to mean "instruction to display information on the display unit 50 of the mobile telephone/processing block 104." "Measuring startup operation?" in Step S20 can be understood to mean "Measurement startup signal received from mobile telephone/processing block 104?"

Even though the flowchart in FIG. 4 shows the measurement/transmission process in Step S30 of FIG. 2 in greater detail, some changes are required in Example 2. In the runner ring sensor block 102 of Example 2, the biometric information can be transmitted in either all-at-once transmission mode or real-time transmission mode. The mode is set based on instruction signals from the mobile telephone/processing block 104. When the all-at-once transmission mode has been set, Step S108 in FIG. 4 is interpreted to mean "Transmission request from mobile telephone/processing block 104?" When set to the real-time transmission mode, Step S108 is interpreted to mean "Mobile telephone in standby?" In other words, in the real-time transmission mode, unit pulse wave information is transmitted as soon as it is created as long as the mobile telephone is in standby and other functions are not being executed. While another function is being executed by the mobile telephone such as a telephone call, the transmission is placed on hold.

Example 3

Figure 6:
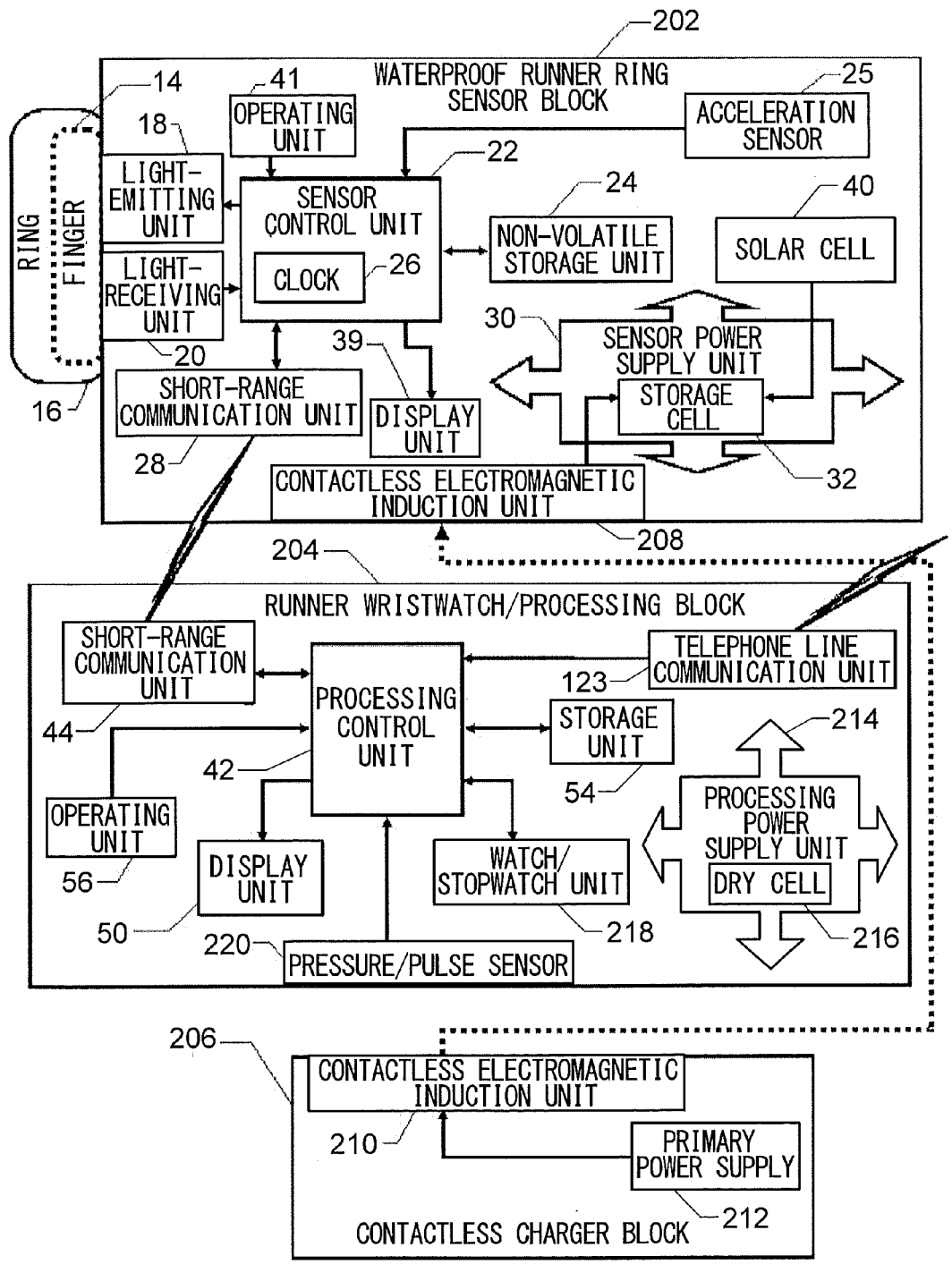
FIG. 6 is a block diagram showing Example 3 of the present invention configured as a biometric information measurement device.

FIG. 6 is a block diagram showing Example 3 of the present invention configured as a biometric information measurement device according to an embodiment of the present invention. As in Example 1 and Example 2, Example 3 is configured as a biometric information measuring system able to measure oxygen saturation using the pulse waves and pulse from a runner while running. The primary structural elements are a waterproof runner ring sensor block 202 that can be attached to a finger 14 of the runner, and a runner wristwatch 204 able to establish short-range communication with the ring. Because the runner wristwatch 204 functions as the processing block for the biometric information received from the waterproof runner ring sensor block 202, it is referred to below as the "runner wristwatch/processing block 204." The biometric information measuring system in Example 3 includes a contactless charger block 206 for charging the storage cell 32 in the runner ring sensor block 202.

Most of the configuration in Example 3 is similar to Example 2. The components similar to those in Example 2 are denoted by the same numbers, and further description of these components has been omitted. The runner wristwatch/processing block 204 has a telephone line communication unit 123 dedicated to data communication. As in Example 2, biometric information data can be transmitted to a personal physician. Example 3 differs from Example 2 in that the waterproof runner ring sensor block 202 has a contactless electromagnetic induction unit 208. When this is brought close to a contactless electromagnetic induction unit 210 in the contactless charger block 206, charge voltage is generated using electromagnetic induction. The contactless charger block 206 has a primary power source 212 for supplying electric power to the contactless electromagnetic induction unit 210 in order to charge the device. This primary power supply 212 can be a large battery or an AC adapter connected to an electric power line as in Example 2. A processing power supply unit 214 of the runner wristwatch/processing block 204 includes a replaceable dry cell 216. The dry cell 216 can be replaced with a storage cell chargeable from the outside.

The waterproof runner ring sensor block 202 in Example 3 is adapted so that perspiration produced during running can be washed off with water, and so that the block can be washed with water on being shared an unspecified number of times. The waterproof runner ring sensor block 202 having a contactless electromagnetic induction unit 208 in Example 3 can be applied to the configurations in Example 1 and Example 2.

The runner wristwatch/processing block 204 has an ordinary clock/stopwatch unit 218 used to measure the lap time or elapsed time at a checkpoint while running. The waterproof runner ring sensor block 202 is separated from the runner wristwatch/processing block 204 because the wrist is not suitable for optical measurement of pulse waves. In order to address this problem, a pressure pulse sensor 220 is installed in the runner wristwatch/processing block 204, and the measured pulse signals are used as synchronization signals when correcting the pulse wave signals transmitted from the waterproof runner ring sensor block 202. The function of the sensor control unit 22 in the waterproof runner ring sensor block 202 is similar to the one in Example 2, and the flow from FIG. 2 to FIG. 4 can be applied substantially in the form modified in Example 2.

Example 4

Figure 7:
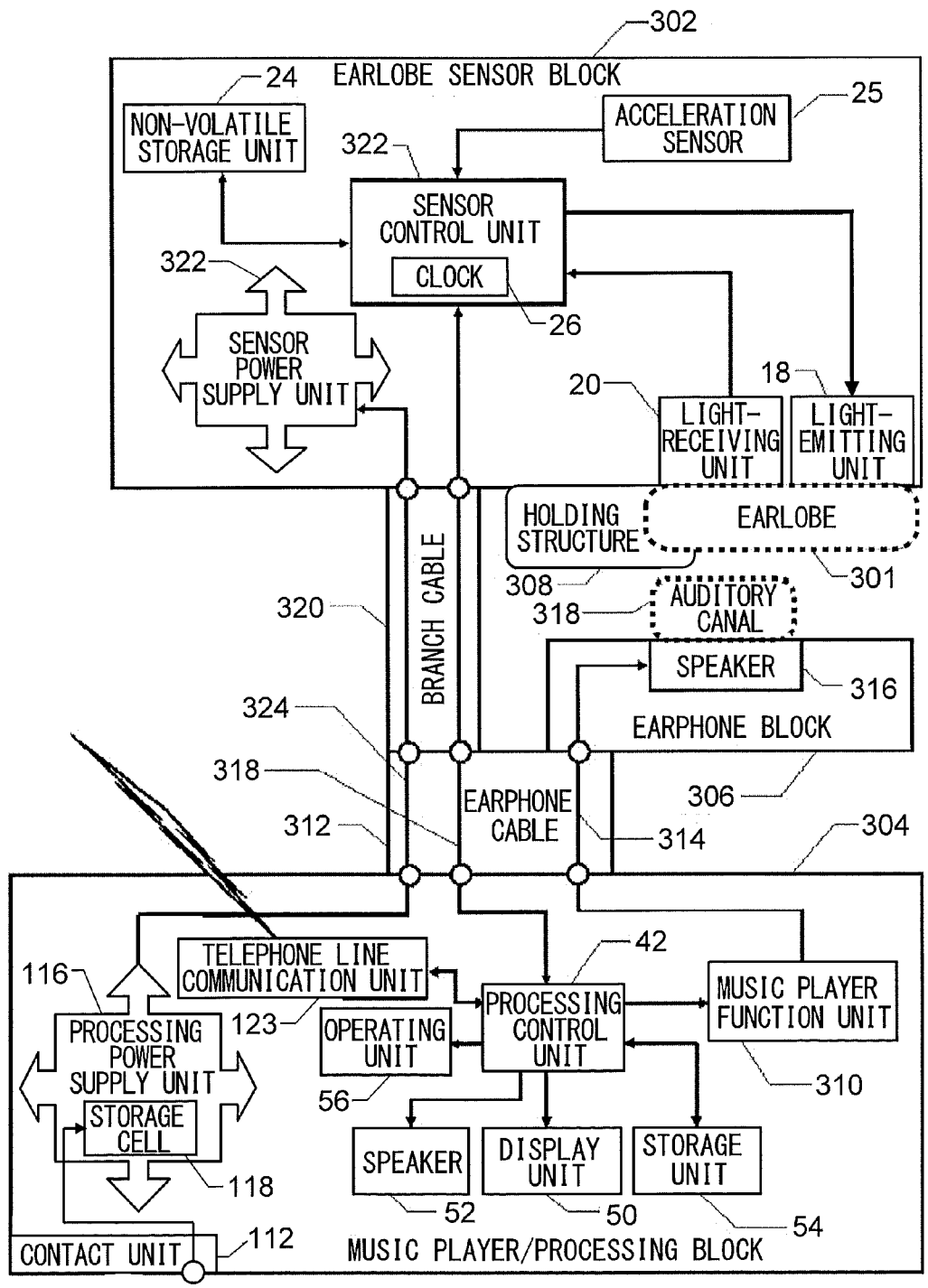
FIG. 7 is a block diagram showing Example 4 of the present invention configured as a biometric information measurement device.

FIG. 7 is a block diagram showing Example 4 of the present invention configured as a biometric information measurement device according to an embodiment of the present invention. As in the first through Example 3s, Example 4 is configured as a biometric information measuring system able to measure oxygen saturation using the pulse waves and pulse from a runner while running. The primary structural elements are an earlobe sensor block 302 that can be attached to an earlobe 301 of the runner, a music player/processing block 304 able to communicate via a cable, and an earphone block 306 able to hear music from the music player/processing block 304. The music player/processing block 304 is configured as a portable music terminal and functions both as a music player whose music source is the earphone block 306 as mentioned above, and as a processing block for biometric information from the earlobe sensor block 302. As in Examples 2 and 3, the system in Example 4 includes a power line charger block for charging the music player/processing block 304. In order to avoid complexity, this has been omitted from the drawing.

Because the basic configuration of Example 4 is similar to Examples 2 and 3, the components common to all of them are denoted by the same reference numerals as those used in Examples 2 and 3, and further description has been omitted. However, while the measurement target in Examples 1 through 3 is a finger 14, the target in Example 4 is an earlobe 301. The earlobe sensor block 302 has a holding structure 308 for holding the earlobe 301 so that the light-emitting unit 18 and the light-receiving unit 20 make contact with the earlobe 301. This holding structure 308 can be a pincher or hook.

The music player/processing block 304 is equipped with a music player function unit 310 for outputting music signals. The outputted music signals are transmitted to the speaker 316 in the earphone block 306 via a music signal line 314 in an earphone cable 312, and music is outputted into an auditory canal 318 in which the earphone block 306 has been inserted. The earphone cable 312 includes a biometric information transmission line 318 connected by wires to the processing control unit 42 in the music player/processing block 304 and the sensor control unit 322 in the earlobe sensor block 302, and branches into a branch cable 320. The earphone cable 312 also includes a power supply line 324 for supplying electric power from the processing power supply unit 116 in the music player/processing block 304 to a sensor power supply unit 322 in the earlobe sensor block 302, and branches into the branch cable 320. Because the earlobe sensor block 302 is configured to hold the earlobe 301 of the same ear as the auditory canal 318 in which the earphone block 306 has been inserted, the earphone cable 312 can also include the music signal line 314 from the music player/processing block 304 to the earphone block 306, and the biometric information transmission line 318 and power supply line 324 from the music player/processing block 304 to the earlobe sensor block 302.

In Example 4, the earlobe sensor block 302 can be configured as an earring. When it is not desirable from a design standpoint that a cable be connected, the biometric information transmission between the earlobe sensor block 302 and the music player/processing block 304 can be performed wirelessly using short-range communication units 28, 44 similar to those in FIG. 6. In the power supply configuration, a storage cell 32 and contactless electromagnetic induction unit 208 similar to those in FIG. 6 are installed in the sensor power supply unit 322, and these are configured so that charging can be performed using a contactless charger block 206 similar to the one in FIG. 6. The earlobe sensor block 302 is not restricted to the configuration shown in FIG. 7 in which light emitted from a light-emitting unit 18 and reflected by the earlobe tissue while being absorbed by the blood inside the earlobe 301 is returned to a light-receiving unit 20 on the same side of the earlobe 301. For example, the light-receiving unit 20 can be installed on the opposite side of the earlobe 301 from the light-emitting unit 18, and the earlobe 301 can be held by the light-emitting unit 18 and the light-receiving unit 20.

The function of the sensor control unit 322 in Example 4 is substantially similar to the one in Example 2, and the flow from FIG. 2 to FIG. 4 can be used essentially in the form modified in Example 2. Therefore, the various operations used to obtain biometric information are performed together by operating the operating unit 56 in the music player/processing block 304. Also, the various displays related to obtaining biometric information based on these operations are displayed primarily on the display unit 50 of the music player/processing block 304. Thus, the earlobe sensor block 302 functions as a sensor accessory of a music player having a biometric information obtaining function. The operations and display screens related to obtaining biometric information are centrally managed on the music player/processing block 304 side.

There are many other advantages in addition to those described above related to linking a music player with a biometric information measurement device and using an ear listening to music as the measurement target, as in Example 4. For example, because the music outputted during biometric information measurements can be identified, the effects of music on biometric information and the correlation between them can be ascertained as information. Also, biometric information can be monitored, and music suitable for relieving tension or overload can be automatically selected or the volume and acoustic quality of the music can be automatically adjusted.

Example 5

Figure 8:
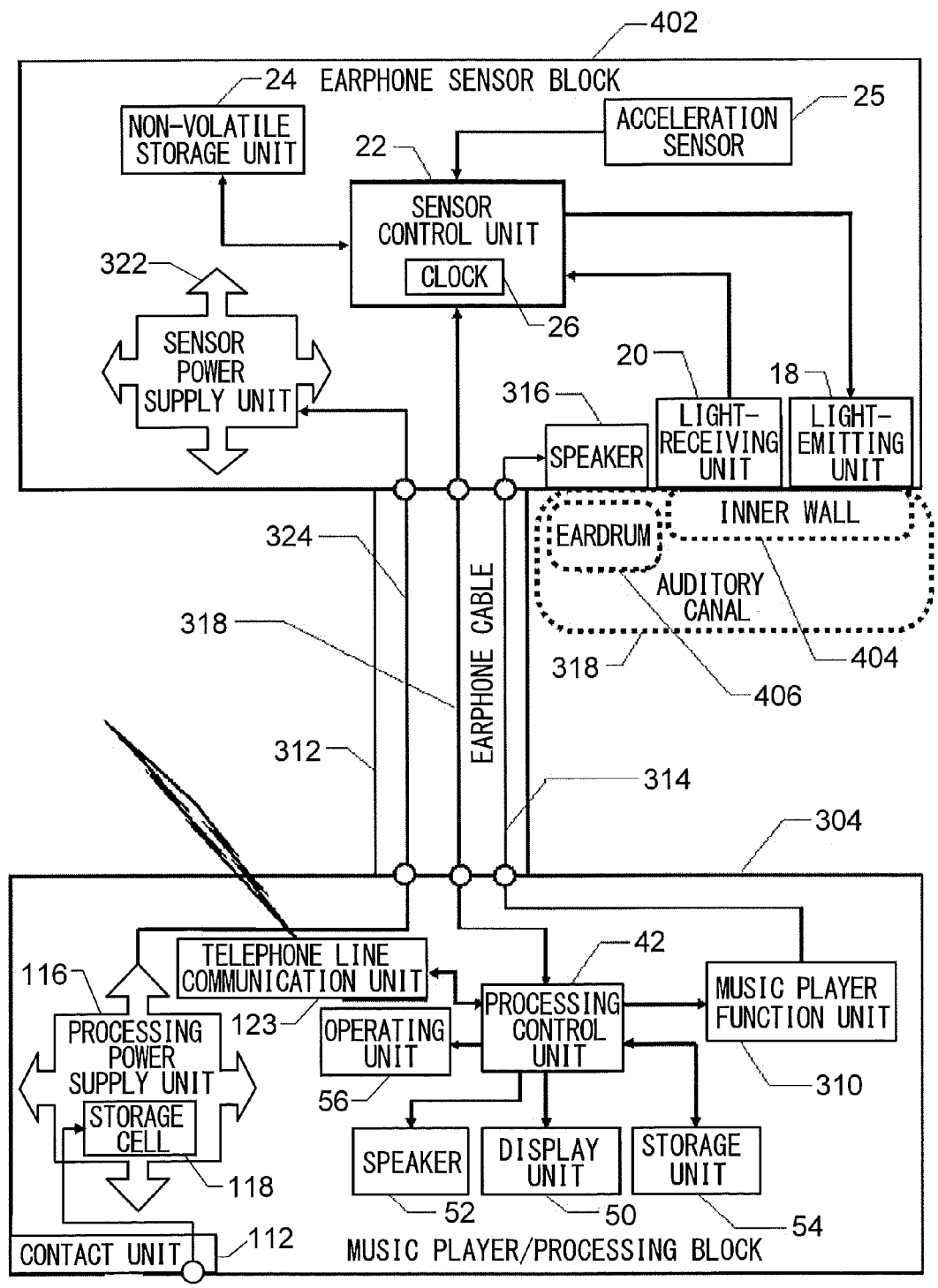
FIG. 8 is a block diagram showing Example 5 of the present invention configured as a biometric information measurement device.

FIG. 8 is a block diagram showing Example 5 of the present invention configured as a biometric information measurement device according to an embodiment of the present invention. As in Example 4, Example 5 is configured as a biometric information measuring system which uses an ear as the measurement target and which is able to measure oxygen saturation using the pulse waves and pulse from a runner while running. Because most of the configuration is similar to the one in Example 4, components common to both are denoted by the same reference numerals as those used in Example 4 and further description has been omitted. The points of difference between Example 5 in FIG. 8 and Example 4 in FIG. 7 are the integration of the sensor block with the earring block to constitute an earphone sensor block 402. Also, the measurement target is not the earlobe, but the inner wall of the auditory canal.

The following is a detailed description. The earphone sensor block 402 is configured so that the light-emitting unit 18 and the light-receiving unit 20 come into close contact with the inner wall 404 of the auditory canal 318 when the earphone sensor block 402 is inserted into the auditory canal 318. As a consequence, light emitted from the light-emitting unit 18 and reflected by the tissue surrounding the auditory canal while being absorbed by the blood in the blood vessels surrounding the auditory canal is returned to the light-receiving unit 20. At the same time, sound is outputted from the speaker 316 inside the auditory canal 318 towards the eardrum 406. In this integrated configuration, the music signal line 314, the biometric information transmission line 318, and the power supply line 324 pass through the earphone cable 312 and are connected by wires to the earphone sensor block 402 and the music player/processing block 304.

Example 6

Figure 9:
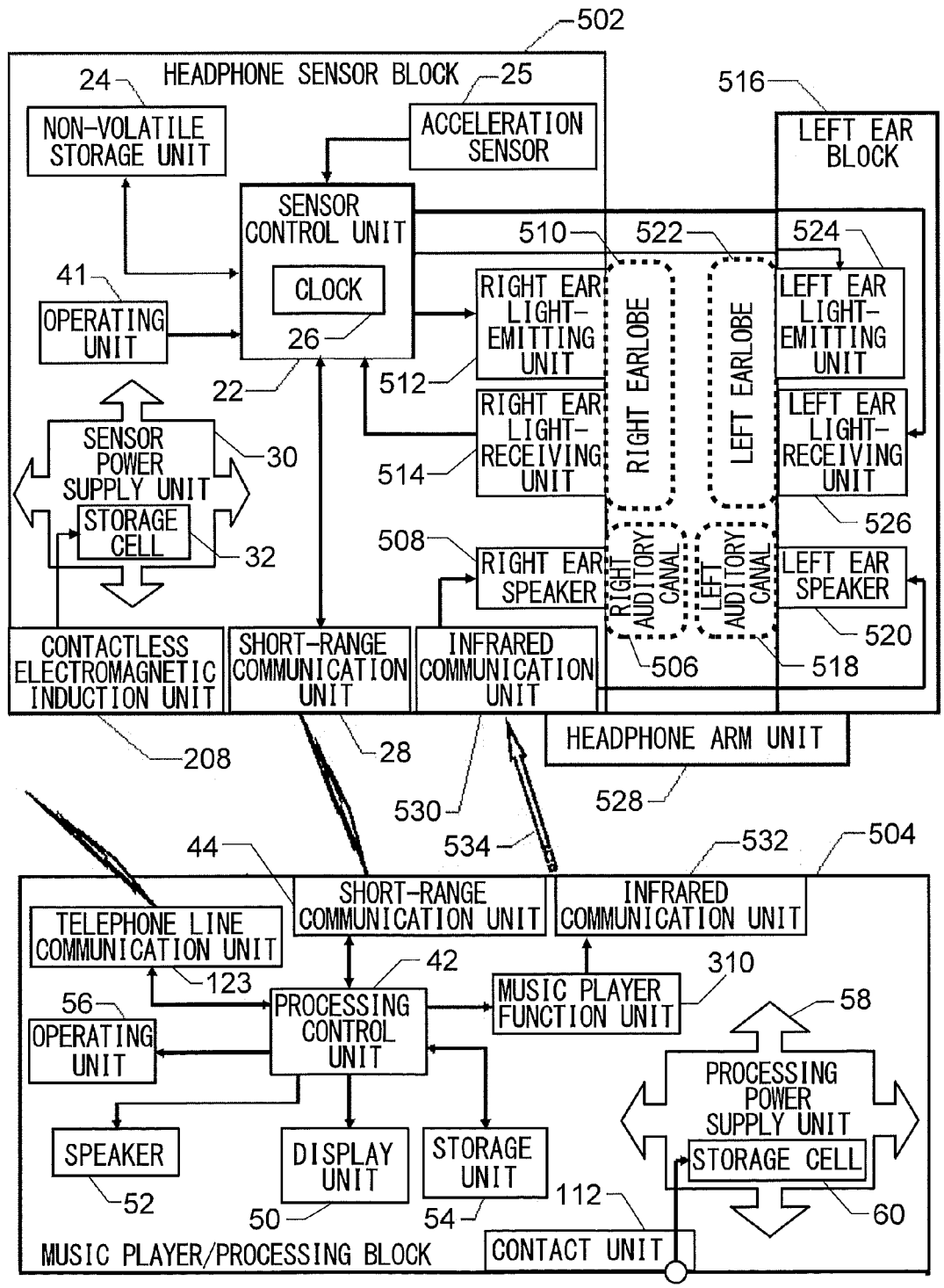
FIG. 9 is a block diagram showing Example 6 of the present invention configured as a biometric information measurement device.

FIG. 9 is a block diagram showing Example 6 of the present invention configured as a biometric information measurement device according to an embodiment of the present invention. As in Example 5, Example 6 is configured as a biometric information measuring system which uses an ear as the measurement target and which is able to measure oxygen saturation using the pulse waves and pulse from a runner while running. As in Example 5 in FIG. 8, the system in Example 6 has a sensor block integrated with the headphones serving as a music output unit for a music player in order to constitute a headphone sensor block 502. Also, the headphone sensor block 502 communicates wirelessly with a music player/processing block 504. The measurement target in Example 6, as in Example 4, is the earlobe. Because the basic internal configuration of Example 6 is similar to the configurations in Example 1 through 5, the components common to all of them are denoted by the same reference numerals as those used in Examples 1 through 5 and further description has been omitted.

The following is a detailed description of the portion characterizing Example 6. The headphone sensor block 502 has a right ear speaker 508 for a right ear auditory canal 506, and a right ear light-emitting unit 512 and a right ear light-receiving unit 514 for a right earlobe 510. Correspondingly, a left ear block 516 has a left ear speaker 520 for a left ear auditory canal 518, and a left ear light-emitting unit 524 and a left ear light-receiving unit 526 for a left earlobe 522. The left ear block 516 is held on the headphone block 502 by a headphone arm unit 528, and both ears are clasped over the crown of the head by the headphone sensor block 502 and the left ear block 516. When the headphones are attached to the head, the right ear light-emitting unit 512, the right ear light-receiving unit 514, the left ear light-emitting unit 524, and the left ear light-receiving unit 526 can thereby make contact, respectively, with the right earlobe 510 and the left earlobe 522 below the right ear auditory canal 506 and the left ear auditory canal without requiring a special holding means. By measuring both the right earlobe 510 and the left earlobe 520 at the same time, the amount of pulse wave measurement information is increased. In order to simplify the drawing, the overall positional relationship between the headphone sensor block 502, the left ear block 516, and the headphone arm unit 528 is inverted with respect to top and bottom in FIG. 9.

The right ear light-emitting unit 512, the right ear light-receiving unit 514, the left ear light-emitting unit 524, and the left ear light-receiving unit 526 are each connected to and controlled by the sensor control unit 22. The right ear speaker 508 and the left ear speaker 520 also output audio, respectively, to the right ear auditory canal 506 and the left ear auditory canal 518 based on stereo audio signals received by an infrared communication unit 530. The audio signals outputted from the music player function unit 310 are converted to infrared light 534 by the infrared communication unit 532 in the music player/processing block 504, and transmitted to the infrared communication unit 530 in the headphone sensor block 502. This is depicted conceptually in FIG. 9 in order to avoid complexity. The audio signal line from the infrared communication unit 530 to the left ear speaker 520, and the connection line connecting the left ear light-emitting unit 524 and the left ear light-receiving unit 526 to the sensor control unit 22 are both actually linked to the headphone sensor block 502 and the left ear block 516 via the headphone arm unit 528.

Seventh Example

Figure 10:
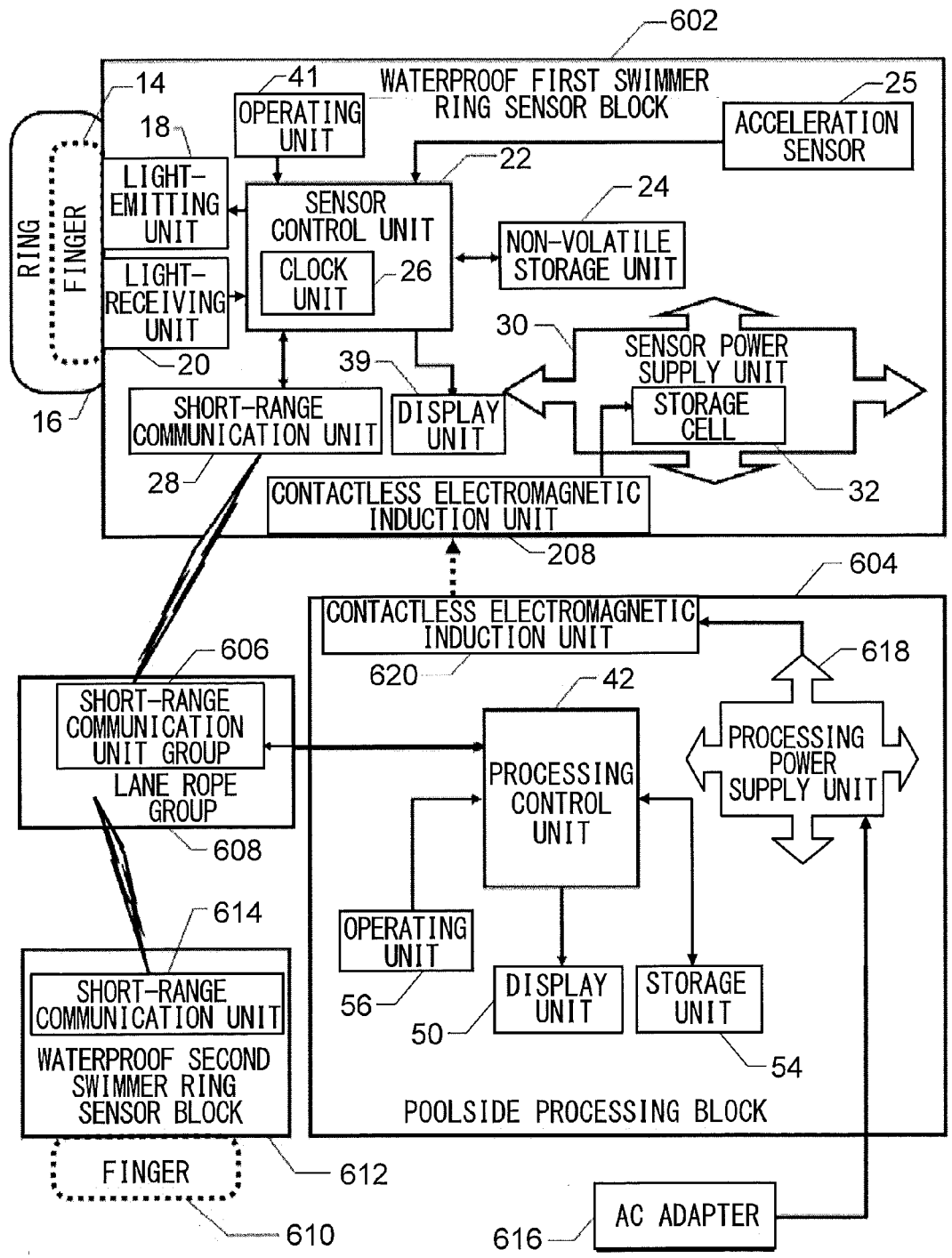
FIG. 10 is a block diagram showing Example 7 of the present invention configured as a biometric information measurement device.

FIG. 10 is a block diagram showing Example 7 of the present invention configured as a biometric information measurement device according to an embodiment of the present invention. Example 7 is configured as a biometric information measuring system which can use pulse waves and the pulse of a plurality of swimmers during training in a pool to measure oxygen saturation. In a manner similar to Example 1, the minimum units include a lane rope group 608 in a pool equipped with a waterproof first swimmer ring sensor block 602 that can be attached to a finger 14 of the first swimmer, a poolside processing block 604, and a short-range communication unit group 606 for receiving the biometric information transmitted from the short-range communication unit 28 in the waterproof first swimmer ring sensor block 602. The short-range communication unit group 606 has reception antenna units in numerous locations along the lane rope group 608 in order to be able receive biometric information in real time irrespective of where the first swimmer is swimming in the pool. Also, the short-range communication unit group 606 or its antenna unit is distributed at least among every other among a plurality of lane ropes inside the pool in order to be able to receive biometric information from the lane ropes on at least the left side or the right side of the lane when a swimmer is swimming through the lane.

The poolside processing block 604 can also process biometric information from a plurality of swimmers inside a pool via short-range communication unit groups 606 installed in the lane rope groups 608 in the manner described above. For example, short-range wireless communication can be performed via a lane rope group 608 with a short-range communication unit 614 in the waterproof second swimmer ring sensor block 612 attached to a finger 610 of a second swimmer. Because the configuration of the waterproof second swimmer ring sensor block 612 is similar to the waterproof first ring sensor block 602, depiction of the internal configuration has been omitted from FIG. 10 except for the short-range communication unit 614. In order to simplify the drawing, only the waterproof first swimmer ring sensor block 602 and the waterproof second swimmer ring sensor block 612 are shown in FIG. 10. The poolside processing block 604 can communicate with waterproof swimmer ring sensor blocks having the same configuration attached to the fingers of even more swimmers in the pool and can obtain biometric information from each swimmer via the short-range communication unit group 606 installed in the lane rope group 608.

Power is supplied to the various components in the poolside processing block 604 from a processing power supply unit 618 supplied power, in turn, from an AC adapter 616. The power supply unit 618 also supplies power to a contactless electromagnetic induction unit 620. Thus, when the contactless electromagnetic induction unit 208 in the waterproof first swimmer ring sensor block 602 is brought close to the contactless electromagnetic induction unit 620 in the poolside processing block 604, the storage cell 32 can be charged using electromagnetic induction. Because the rest of the configuration of Example 7 in FIG. 10 is similar to Examples 1 through 6, the components common to all of them are denoted by the same reference numerals used in Examples 1 through 5, and further description has been omitted. The internal configuration of the waterproof first swimmer ring sensor block 602 in particular is nearly identical to Example 3 in FIG. 6. However, whereas the device of Example 3 has a waterproofness of approximately the level encountered in everyday situations, the waterproofness of the device of the seventh example is of a higher-level specification because the swimmer is immersed in a pool and engages in intense activity in the water.

Example 8

Figure 11:
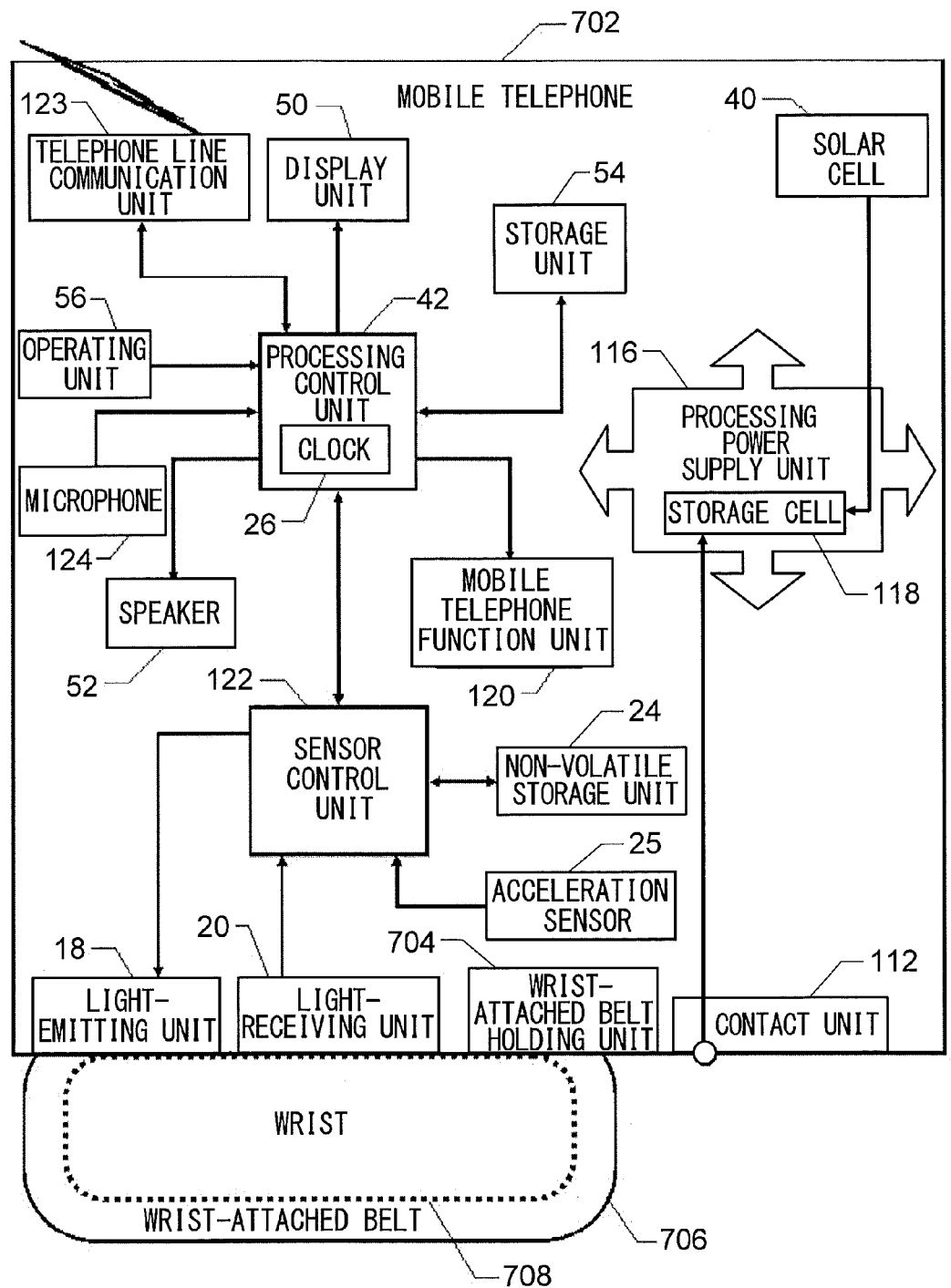
FIG. 11 is a block diagram showing Example 8 of the present invention configured as a biometric information measurement device.

FIG. 11 is a block diagram showing Example 8 of the present invention configured as a biometric information measurement device according to an embodiment of the present invention. As in the case of the first and Example 2s, Example 8 comprises a biometric information measuring system able to measure oxygen saturation using the pulse waves and pulse of a person. As in Example 2, Example 8 is linked to a mobile telephone function. However, in Example 2, the configuration of the mobile telephone/processing block 104 is essentially an ordinary mobile telephone. A separate runner ring sensor block 102 is provided, and the functions of the processing block in the mobile telephone/processing block 104 are provided as application software for the mobile telephone. By contrast, in Example 8, a mobile telephone 702 is combined with a biometric information sensor, and the light-emitting unit 18 and the light-receiving unit 20 are installed in the mobile telephone 702 as hardware.

In the configuration of Example 8, the runner ring sensor block 102 and the mobile telephone/processing block 104 in Example 2 are essentially combined as the mobile telephone 702. The internal configurations of these components are essentially the same. Thus, the components identical to those in Example 2 are denoted by the same reference numerals, and further description has been omitted. The following description will focus on the differences. First, a result of the combination is that the processing control unit 42 and the sensor control unit 122 communicate directly inside the mobile telephone 702 and not via short-range communication units or the like. Another result of the combination is that the processing power supply unit 116 is also used to supply power to the structural elements for measuring biometric information. The solar cell 40 provides output to the storage cell 118 in the dual-purpose processing power supply unit 116. The separately installed operating unit 56 and display unit 50 above are also integrated into one.

As for the functions of the sensor control unit 122 in Example 8, the flow from FIG. 2 to FIG. 4 can be used essentially in the form modified in Example 2. As a result of the light-emitting unit 18 and the light-receiving unit 20 being arranged on the surface of the mobile telephone 702, measurements can be performed simply by placing a finger or the like where the light-emitting unit 18 and light-receiving unit 20 are positioned. In this form, the measurement of biometric information is accordingly suitable for a resting state rather than, e.g., during running. In order to perform measurements of the runner while they are running, a wrist attachment belt 706 is passed through a wrist attachment belt holder 704, and the telephone is attached to a wrist 708 so that the light-emitting unit 18 and the light-receiving unit 20 face the wrist 708.

Figure 12:
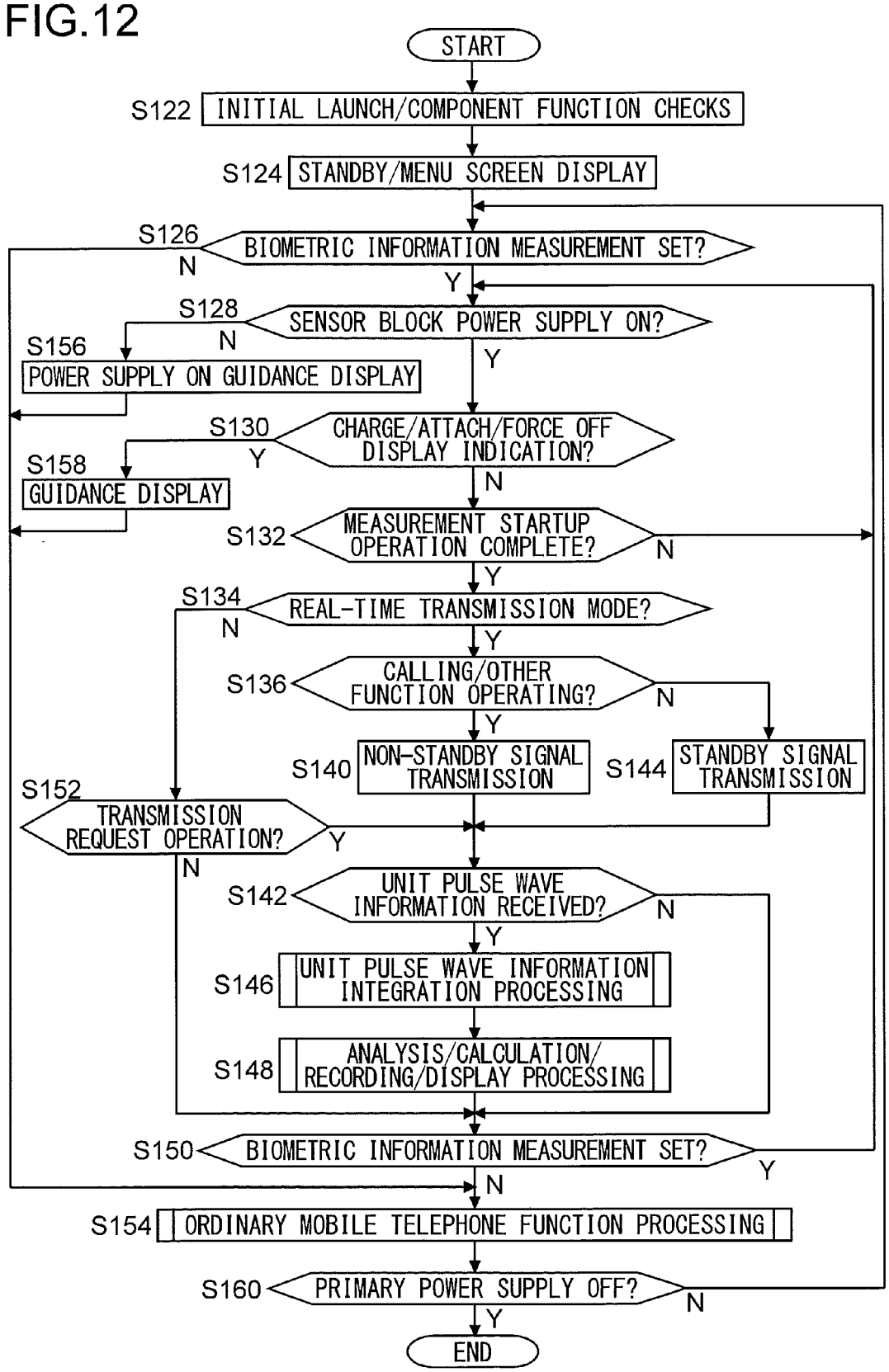
FIG. 12 is a flowchart showing the functions of the processing control unit in Example 2.

FIG. 12 is a flowchart showing the functions of the processing control unit 42 in Example 2 of the present invention as shown in FIG. 5. The flow is started by turning on the primary power supply unit of the mobile telephone/processing block 104, and in Step S122 a check is made as to whether or not the telephone has been initialized and the functions of the various components are checked. In Step S124, the device goes into standby and a menu screen is displayed on the display unit 50. The menu includes biometric information measurement and can be selected.

Next, the flow advances to Step S126, and a check is made as to whether or not biometric information measurement has been selected from the menu and the measurements set by an operation of the operating unit 56. When set, a check is made in Step S128 as to whether or not the power supply of the runner ring sensor block 102 is in the ON state. When the power supply is in the ON state, the flow advances to Step S130. In Step S130, a check is made as to whether or not instructions for the charge guidance display, the finger attachment guidance display, or the force OFF warning display have been issued by the runner ring sensor block 102 in accordance with the flow in FIG. 2. If no instructions have been issued, the flow advances to Step S132 where a check is made as to whether or not the measurement startup operation has been activated using the operating unit 56. When the operation has occurred, the flow advances to Step S134.

When the activation of the measurement startup operation has not been detected in Step S132, the flow returns to Step S128 and, subsequently, the power supply to the runner ring sensor block 102 is turned on, and the loop from Step S128 to Step S132 is repeated and the flow stands by for the measurement startup operation unless a display instruction such as charging is issued. As described below, when the measurement startup operation has not been performed even after a predetermined period of time has elapsed since the runner ring sensor block 102 was turned on, the runner ring sensor block 102 is forcibly turned off based on a YES determination in Step S8 in FIG. 2. Therefore, when there is a NO determination in Step S128, the loop from Step S126 to Step S132 is removed, and the biometric information measurement setting is cancelled.

In Step S134, a check is made as to whether or not the real-time transmission mode has been set. When the real-time transmission mode has been set, the flow advances to Step S136 where a check is made as to whether or not the mobile telephone/processing block 104 is being used to conduct a telephone call or perform a function other than biometric information measurement. When a telephone call is being conducted or another function is being performed, the flow advances to Step S140. A signal indicating no standby state is transmitted to the runner ring sensor block 102, and the flow advances to Step S142. The runner ring sensor block 102 receives the signal indicating no standby state, and transmission of unit pulse wave information is put on hold based on a NO response in Step S108 of FIG. 4. When it is detected in Step S136 that a telephone call is being conducted or another function is being performed, the flow advances to Step S144. A signal indicating a standby state is transmitted to the runner ring sensor block 102, and the flow advances to Step S142. This is received by the runner ring sensor block 102, and new unit pulse wave information is transmitted in real time to the mobile telephone/processing block 104 as soon as it is obtained from Step S108 to Step S112 in FIG. 4.

In Step S142, a check is made as to whether or not unit pulse wave information has been received. When unit pulse wave information has been received, the flow advances to Step S146, and integration processing is performed on the unit pulse wave information. In this processing, the unit pulse wave information, which is a fragment of pulse wave information, is integrated according to wavelength and individual. Next, the flow advances to Step S148 where the information is analyzed (the pulse wave shape is assessed, the information is matched with typical patterns or diagnostic purposes, and other analyses are performed.), oxygen saturation is calculated based on the pulse wave information, the analysis and calculation results are recorded, and the biometric information measurement results based on these are displayed. The flow then proceeds to Step S150. A process can be added in Step S148 to automatically transmit the pulse wave information from the telephone line communication unit 123 to a personal physician. When the reception of unit pulse wave information is not detected in Step S142, the flow advances directly to Step S150.

If the real-time transmission mode is not detected in Step S134, it means that the all-at-once transmission mode has been set. The flow proceeds to Step S152 where a check is made as to whether or not a transmission request operation has been performed using the operating unit 56. When a transmission request operation has been detected, the flow advances to Step S142, and a check is made as to whether or not unit pulse wave information has been received. When a transmission request operation has not been detected in Step S152, the flow advances directly to Step S150.

In Step S150, a check is made as to whether or not a biometric information measurement has been set. A biometric information measurement setting is disabled by operating the operating unit 56. However, as a result of the disabling operation, the flow advances to Step S154 unless it has been detected in Step S150 that no biometric information measurement setting has been made. When the continuation of a biometric information setting has been detected in Step S150, the flow returns to Step S128. Subsequently, the flow from Step S128 to Step S152 is repeated and the measurement continues until the sensor block power supply is turned off, a display instruction such as charge guidance is issued, or the biometric information measurement setting is disabled.

When a biometric information measurement setting is not detected in Step S126, the flow advances immediately to Step S154. Also, when it cannot be detected in Step S128 that the power supply to the runner ring sensor block 102 has been turned on, instructions are issued in Step S156 to display guidance on the display unit 50 to turn on the power supply for the runner ring sensor block 102. The flow then proceeds to Step S154. Furthermore, when it has been detected in Step S130 that instructions have been issued from the runner ring sensor block 102 for the charge guidance display, the ring attachment guidance display, or the force off warning display, the corresponding guidance is displayed on the display unit 50 in Step S158, and then the flow advances to Step S154.

Processing related to ordinary mobile telephone functions is performed in Step S154. When the processing related to ordinary mobile telephone functions in Step S154 has reached a milestone or has ended, and the standby/menu screen display has returned, the flow advances to Step S160 where a check is made as to whether or not the primary power supply for the mobile telephone/processing block 104 has been turned off. When it has been detected that the primary power supply has been turned off, the flow is ended. When it has not been detected in Step S160 that the primary power supply has been turned off, the flow returns to Step S126. The flow from Step S126 to Step S160 is then repeated until the primary power supply has been turned off.

Figure 13:
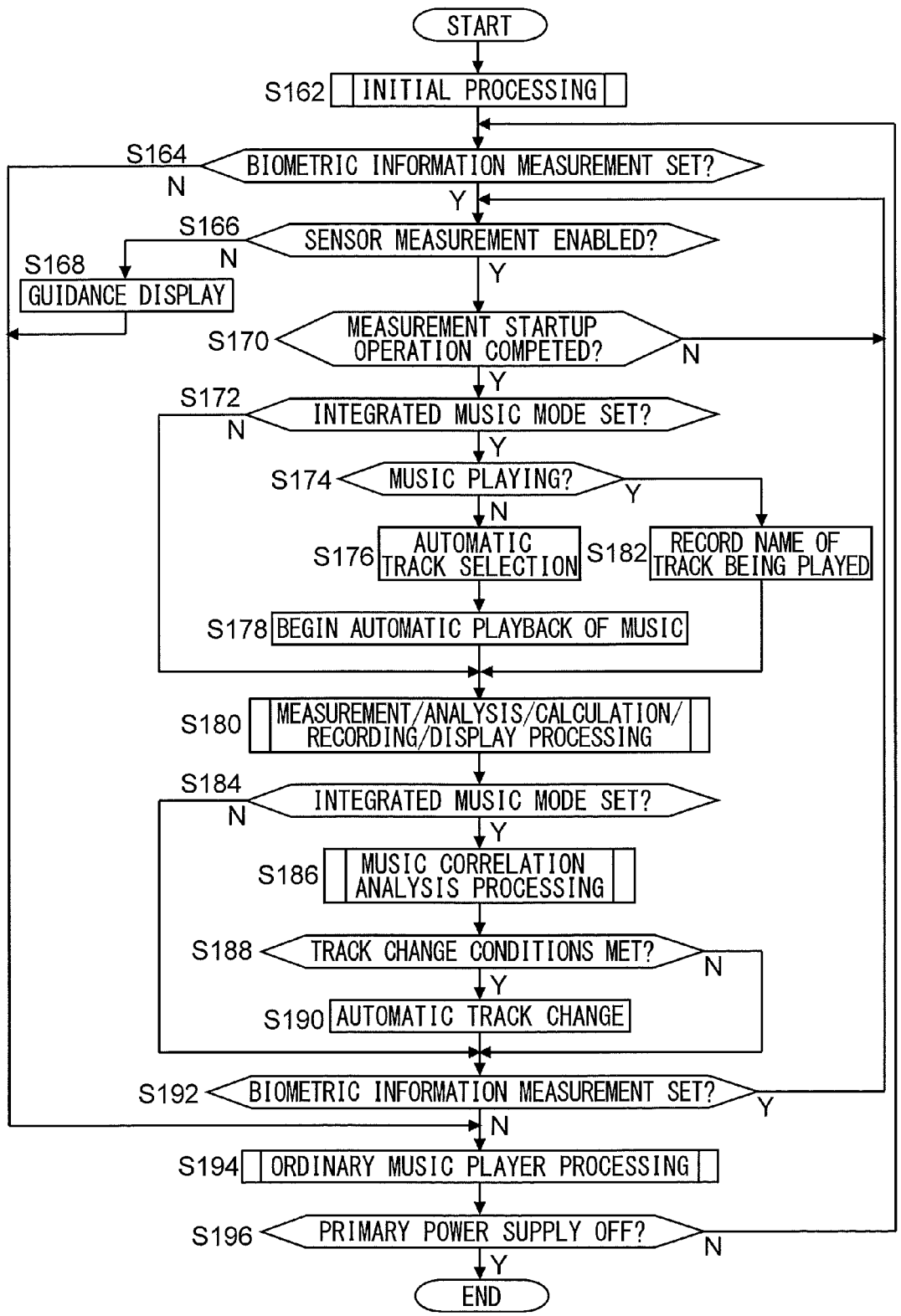
FIG. 13 is a flowchart showing the functions of the processing control unit in Examples 1 through 6.

FIG. 13 is a flowchart showing the functions of the processing control unit 42 in the music player/processing block 304, 504 of Example 4 shown in FIG. 7 to Example 6 shown in FIG. 9. The flow is started when the primary power supply to the music player/processing block 304, 504 is turned on. The flow in FIG. 13 shares many components with the flow in FIG. 12. These shared components are shown in FIG. 13 so as to be described separately in the following description. Where appropriate, further description has been omitted. When the flow in FIG. 13 is started, initialization is performed in Step S162, and the flow advances to Step S164. The initialization process in Step S162 corresponds to Step S122 and Step S124 in FIG. 12.

Next, the flow advances to Step S164 where a check is made as to whether or not a biometric information measurement has been set by operating the operating unit 56. When one has been set, the flow advances to Step S166 where a check is made as to whether or not the earlobe sensor block 302, the earphone sensor block 402, or the headphone sensor block 502 is able to perform measurements. Step S166 and Step S168 correspond to Step S128, Step S130, Step S156, and Step S158 in FIG. 12. These have been combined in the drawing.

When it has been detected in Step S166 that the sensor block can perform measurements, the flow advances to Step S170 where a check is made as to whether or not the measurement startup operation has been performed using the operating unit 56. When it has been performed, the flow advances to Step S172. When it is not detected in Step S170 that a measurement startup operation has been performed, the flow returns to Step S166. Subsequently, the flow from Step S166 to Step S170 is repeated and the flow stands by for a measurement startup operation as long as the sensor block is able to perform measurements.

When measurement startup has been detected in Step S170, the flow advances to Step S172 where a check is made as to whether or not the integrated music mode has been set. When the integrated music mode has been set, the flow advances to Step S174 where a check is made as to whether or not music is already playing. When music is not already playing, music suitable for correlation with biometric information measurements is automatically selected in Step S176, automatic playback is started in Step S178, and the flow advances to Step S180. When it has been detected in Step S174 that music is already playing, the flow advances to Step S182 where the name of the music being played is recorded as correlation information with the biometric information measurement, and the flow advances to Step S180. When the integrated music mode is not set in Step S172, the flow advances directly to Step S180. Even when music is being played, biometric information measurements can be measured uncorrelated to the music. Automatic play can also be started when no music is being played.

The measurement, analysis, calculation, recording, and display processing in Step S180 are summarized in Step S134 to Step S148 and Step S152 as shown in FIG. 12, for which reason a detailed description has been omitted. When the flow advances from Step S180 to Step S184, a check is again made as to whether or not the integrated music mode has been set. When this setting has been detected, the flow advances to Step S186, and music correlation analysis is performed. In this analysis, the correlation between biometric information and song tempo, time signature, musical instruments, dynamic changes, and volume are analyzed. The uplifting and relaxing effect of music on mental states can thereby be studied. The flow proceeds to Step S188 where a check is made as to whether or not the biometric information obtained as a result of the analysis in Step S186 indicates a situation in which the music should be changed. When such a situation is indicated, the music is automatically changed to something more appropriate in Step S190, and the flow advances to Step S192. When a music changing situation is not indicated in Step S188, the flow advances directly to Step S192. Even when the integrated music mode setting is not detected in Step S184, the flow advances directly to Step S192.

In Step S192 a check is made as to whether or not a biometric information measurement has been set. When the disabling of a biometric information measurement has been detected, the flow advances to Step S194. When the continuation of a biometric information setting is detected in Step S192, the flow returns to Step S166. Subsequently, the flow from Step S166 to Step S192 is repeated as long as the sensor block can no longer perform measurements or the biometric information setting has not been disabled, and the association between the measurement and the playback of music based on the settings is continued.

When a biometric information measurement setting is not detected in Step S164, the flow advances directly to Step S194. When it is detected in Step S166 that the sensor block can no longer perform measurements, instructions are given in Step S168 to display guidance on the display unit 50, and the flow advances to Step S194.

In Step S194, the ordinary music player processing is performed. When the ordinary music player processing performed in Step S194 reaches a milestone or ends, the process returns to the menu screen display and the flow advances to Step S196 where a check is made as to whether or not the primary power supply for the music player/processing block 304 or 504 has been turned off. When it is detected that the primary power supply has been turned off, the flow ends. When it is not detected in Step S196 that the primary power supply has been turned off, the flow returns to Step S164 and the flow from Step S164 to Step S196 is repeated until the primary power supply has been turned off.

Figure 14:
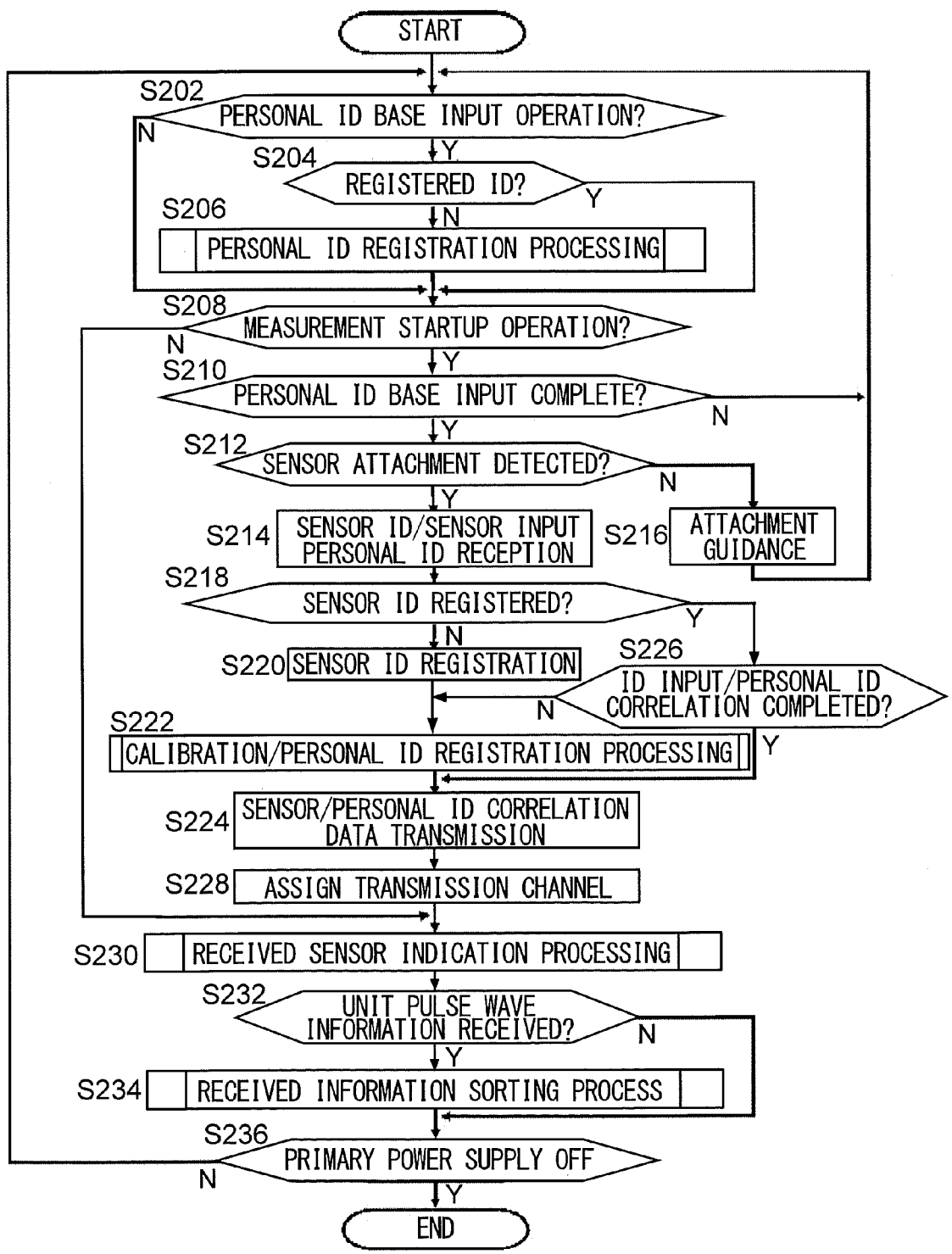
FIG. 14 is a flowchart showing the functions of the processing control unit in Examples 1 and 7.

FIG. 14 is a flowchart showing the functions of the processing control unit 42 for Example 1 of the invention as shown in FIG. 1 and the processing control unit 42 for Example 7 of the invention as shown in FIG. 10. The flow starts when the primary power supply for the escort-vehicle-mounted/base-installed processing block 4 or the poolside processing block 604 in FIG. 10 has been turned on. When the flow has started, first, a check is made in Step S202 as to whether or not a personal ID for starting the measurement process has been inputted to the escort-vehicle-mounted/base-installed processing block 4 or the poolside processing block 604 (referred to below simply as the "base").

When the personal ID has been inputted at the base, the flow advances to Step S204 where a check is made as to whether or not the inputted personal ID has been registered. When the ID has not been registered, the flow advances to Step S208 through the personal ID registration process in Step S206. When it has been confirmed in Step S204 that the personal ID has been registered, the flow advances directly to Step S208. When input of the personal ID has not been confirmed in Step S202, the process proceeds directly to Step S208.

In Step S208 a check is made as to whether or not measurements have been started in a specific sensor block. This check can be performed by checking whether or not a report of the measurement startup operation has been transmitted from the sensor block to the base. The measurement startup operation can be performed from the base. Here, a measurement startup instruction signal is transmitted to the sensor block. When the measurement startup operation has been detected as a result of this check, the flow advances to Step S210 where a check is made as to whether or not the personal ID of the person beginning measurements has been inputted prior to the measurement startup operation. When the personal ID has not been inputted, the flow returns to Step S202 in order to respond to the input. In other words, when a new measurement has been started by a specific sensor block, the measurement is not performed unless a personal ID has been inputted prior thereto, even when a measurement startup operation has been detected in Step S208.

When it has been confirmed that a personal ID has been inputted in Step S210, the flow advances to Step S212 where a check is made as to whether the sensor block has been attached to a finger of the person beginning the measurement. This check can be performed by having the sensor block perform the functions in Step S10 through Step S14 in FIG. 2 and then receiving an attachment OK signal. When sensor attachment has been detected in Step S212, the flow advances to Step S214. When sensor attachment has not been confirmed in Step S212, the flow advances to Step S216, guidance for attachment is displayed on the display unit 50, an attachment guidance signal is transmitted to the sensor block, this is displayed on the display unit 39 of the sensor block, and the flow returns to Step S202. Even when a measurement operation has been performed, the measurement does not occur unless sensor attachment has been confirmed in this way.

In Step S214, the ID unique to the sensor block and the personal ID inputted using the sensor block are received from the sensor block, and the flow advances to Step S218. In Step S218, a check is made as to whether or not the sensor ID received in Step S214 has been registered. When it has not been registered, the flow advances to Step S220 where the sensor ID is registered anew. Next, the flow advances to Step S222 where the sensor block cooperates in the calibration/personal ID registration process. Calibration data is stored in the storage unit 54 so that it can be identified by the sensor ID and the personal ID, and the flow advances to Step S224. When it has been confirmed in Step S218 that the sensor ID has been registered, the flow advances to Step S226 where a check is made as to whether or not the sensor block currently attached to the finger of the person who has inputted the ID information in order to perform the current measurement has been calibrated. When calibration has not been performed, the flow advances to the calibration/personal ID registration process in Step S222. Also, when it has been confirmed in Step S226 that the finger of the person who has inputted the ID information has been calibrated, the flow advances to Step S224.

In Step S224, the sensor/personal correlation data identified by a sensor ID and personal ID is retrieved from the storage unit 54 and transmitted to the sensor block. Communication with the base required for the functions in Step S208 through Step S224 is performed using a dedicated channel for registration settings. Next, in Step S228, a channel is allocated for transmissions to a sensor block able to transmit measurement data using the process explained above, and the flow advances to Step S230. When a measurement startup operation is not detected in Step S208, the flow advances directly to Step S230.

In Step S230, one of the plurality of sensor blocks controlled by the base during the measurement process is specified to receive data. This is described below in greater detail. The flow then proceeds to Step S232 where a check is made as to whether or not unit pulse wave information has been received from the specified sensor block. When the information has been received, the flow advances to Step S234 where the received information is organized, and then proceeds to Step S236. The received information organization process in Step S234 is described below in greater detail. If it cannot be confirmed in Step S232 that the unit pulse wave information has been received, the flow advances directly to Step S236. In Step S236, a check is made as to whether or not the primary power supply at the base has been turned off. When it has been turned off, the flow returns to Step S202 and the loop from Step S202 to Step S236 is repeated. As long as the primary power supply is not turned off, the base is thereby capable of inputting a personal ID for a new measurement, beginning a new measurement, and responding to the receiving and organizing of the unit pulse wave information from a plurality of sensor blocks during the measurement.

Figure 15:
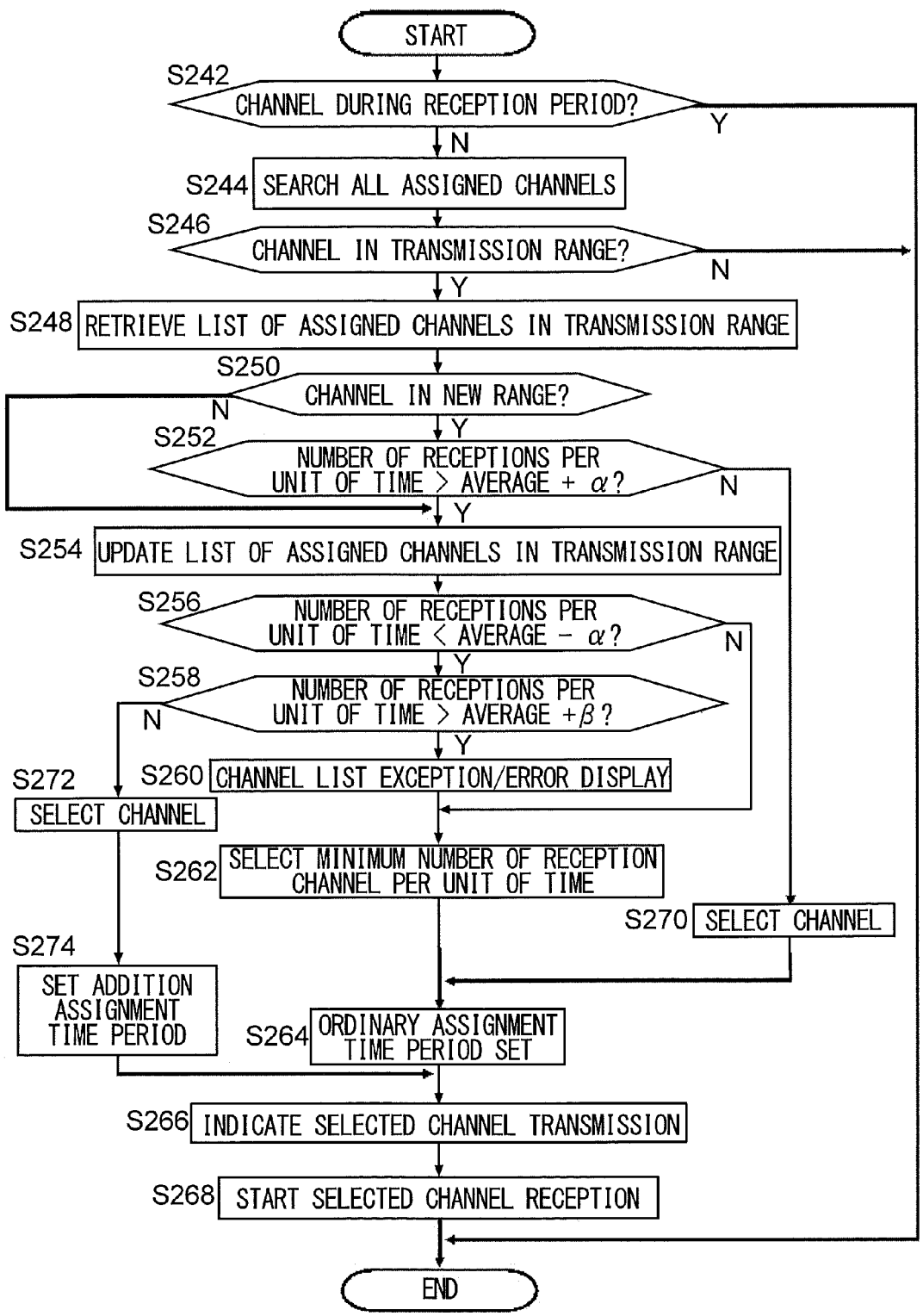
FIG. 15 is a flowchart showing Step S230 in FIG. 14 in greater detail.

FIG. 15 is a flowchart showing the received sensor specification process in Step S230 of FIG. 14 in greater detail. When the flow has started, a check is made in Step S242 as to whether or not the channel allocated to a given sensor block is within the current reception time period. When the channel is within the current reception time period, the flow ends immediately without another channel being specified. In other words, reception of data from the sensor block to which the channel is allocated, or a standing by for the reception, continues for the channel in question until the allocated period of time has ended.

By contrast, when there is no channel within the reception time period, or the allocated period of time has ended before allocation of the channel, the flow advances to Step S244 and subsequent steps in order to specify a channel within the next allocated period of time. First, in Step S244, all of the allocated channels are searched in successive order to determine whether or not any are within communication range, and the presence or absence of a response is confirmed. The flow advances to Step S246 where it is determined from the search results whether or not at least one sensor block is within communication range, and a check is made as to whether or not there has been a response via an allocated channel. When there is no sensor block within communication range and a response has not been received over any channel, the flow ends immediately.

When at least one sensor block is within communication range, the flow advances to Step S248 where a list of allocated channels confirmed to be within communication range during the previous time is retrieved. The flow then proceeds to Step S250 where the results of the check in Step S246 are compared to the list retrieved in Step S248 to check whether or not there are new channels within communication range. When as a result there is a new channel within range, the flow advances to Step S252 where a check is made as to whether or not the number of receptions of unit pulse wave information per unit of time over the channel is greater than the average for all channels by a predetermined amount. When so, the new communication range channel is not given special treatment, and the flow advances to Step S254 where the list of allocated channels in communication range is simply updated. When it is confirmed in Step S250 that there are no new channels in communication range, the flow advances directly to Step S254 where the list of allocated channels in communication range is updated. Because no new channels in communication range are added at this time, the update only entails the deletion of channels outside of communication range.

Next, in Step S256, a check is made as to whether or not the number of receptions of unit pulse wave information per unit of time over a channel is greater than the average for all channels by a predetermined amount. When so, the flow advances to Step S258 where a check is made as to whether the number of selections per unit of time for a channel is greater than the average for all channels by a predetermined amount. When so, it means the actual number of receptions by a channel is less than the average by a predetermined amount despite being specified more times than the average by a predetermined amount. The flow then proceeds to Step S260. When the channel is not on the specified target list, and the ability to transmit to the sensor block assigned to the channel is indicated to be abnormal, the flow advances to Step S262. When in Step S56 the number of receptions per unit of time is less than the average for all channels by a predetermined amount, the flow advances directly to Step S262.

In Step S262, the channel with the minimum number of unit pulse wave receptions per unit of time is selected based on the list updated in Step S54 and revised when necessary in Step S260. The flow then proceeds to Step S264. When there is more than one channel with the same minimum number, a channel is selected randomly. Thus, a channel is selected among those with a similar number of receptions beginning with the one having the fewest number of receptions. By contrast, when in Step S252 it is determined that a new channel in reception range does not have a number of unit pulse wave information receptions per unit of time that is greater than the average for all channels by a predetermined amount, the flow advances to Step S270 where the new channel in reception range is immediately given priority. The flow then proceeds to Step S264. When a sensor unit has been outside of communication range, there is a chance that it will again be outside of communication range. It is also unclear whether it will again return to communication range. In order not to miss an opportunity when the sensor unit is within communication range, it is given priority and the latest unit pulse wave information is received from the sensor unit. However, when the number of receptions is greater than the average of all channels, it does not have to be given special treatment. Therefore, as explained above, the flow advances from Step S252 to Step S54.

In Step S264, the normal allocated period of time for reception is set for the channel selected in Step S262 or Step S270, and the flow advances to Step S266. By contrast, if the list has a channel for which it is determined in Step S256 that the number of unit pulse wave information receptions per unit of time is less than the average for all channels by a predetermined amount or more, and for which it is determined in Step S258 that the number of selections per unit of time does not exceed the average for all channels by a predetermined amount or more, the flow advances to Step S272 where the channel is immediately selected. In other words, when it is clear that there is a channel on the list with fewer receptions than average, it is given priority. In Step S274, an allocated period of time for reception is set for the channel that is longer than normal, and the flow then proceeds to Step S266. Because poor reception conditions of indeterminate cause are presumed to be a contributing factor when the actual number of receptions is low, the allocated period of time is proportionately increased as well as the channel being selected at maximum priority, whereby more reception opportunities are afforded.

In Step S266, unit pulse wave information transmission instructions are issued over the channel selected in the manner described above to the sensor block assigned to the channel, reception startup instructions are issued in Step S268, and the flow is ended.

Figure 16:
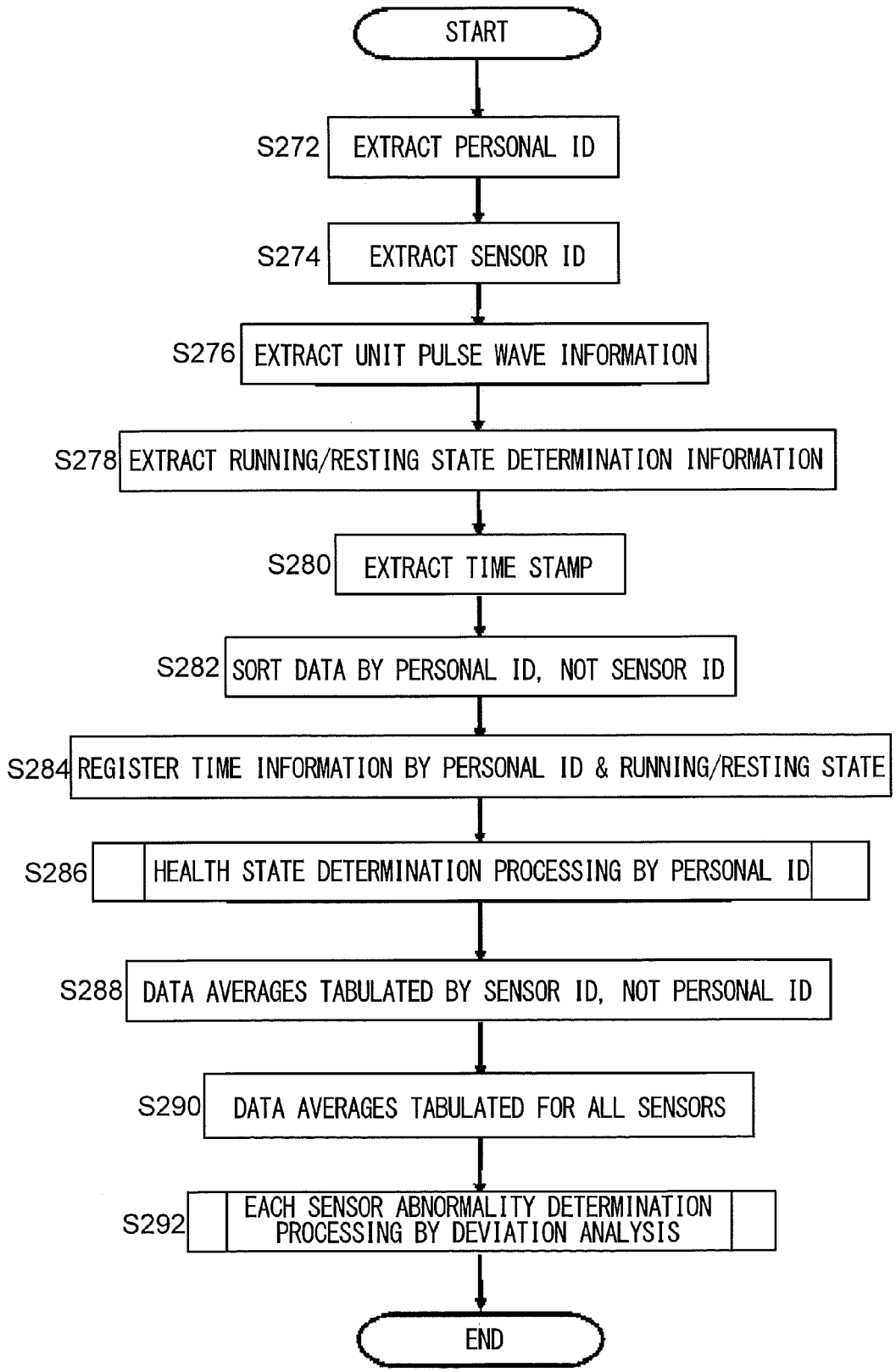
FIG. 16 is a flowchart showing Step S234 in FIG. 14 in greater detail.

FIG. 16 is a flowchart showing the received information organization process in Step S234 of FIG. 14 in greater detail. When the flow is started, first, in Step S272, the personal ID is extracted from the received data. Next, in Step S274, the sensor ID is extracted. In Step S276, the unit pulse wave information which is the main body of the information is extracted. In Step S278, the running/resting state information is extracted as reference information. In Step S280, the time stamp is extracted.

Next, in Step S282, the data is sorted not by sensor ID but by personal ID. In Step S284, the change over time in the unit pulse wave information is recorded by personal ID and by running or resting state. Processing is then performed in Step S286 on the basis of the recorded change to determine the health of each individual including any change over time. In this example, correlation data is created for each combination of sensors and persons in order to address variations among a plurality of sensor blocks and variations in the relationship between sensors and the fingers of different individuals. Sorting can thereby be performed regardless of the sensor being used. In other words, personal data can be sorted without recourse to sensor IDs.

In Step S288, data averages are tabulated not by personal ID but by sensor ID. In Step S290, the sensor data from all sensors is tabulated. In Step S292, abnormality determination processing is performed on each sensor using deviation analysis based on the tabulations for each sensor and the averages for all sensors. The flow is then ended.

The embodiment of the various features explained above is not limited to this example. Other embodiments are certainly possible. An example is the relationship between sensor blocks and the persons wearing the sensor blocks. In the example, as shown in Step S214 of FIG. 14, a personal ID inputted on the sensor block side is received along with the sensor ID of the sensor block. However, the relationship between specific information on the sensor block and specific information on the individual is not limited to the embodiment in this example. For example, when there is a personal ID input operation check in Step S202 of FIG. 14, and the sensor block ID is inputted on the base side along with the personal ID when the person is handed the sensor to put on, only the sensor ID has to be received in Step S214. The personal ID does not have to be inputted on the sensor block side in order to confirm the person wearing the sensor block. The flow can then advance from Step S218.

Example 9

Figure 17:
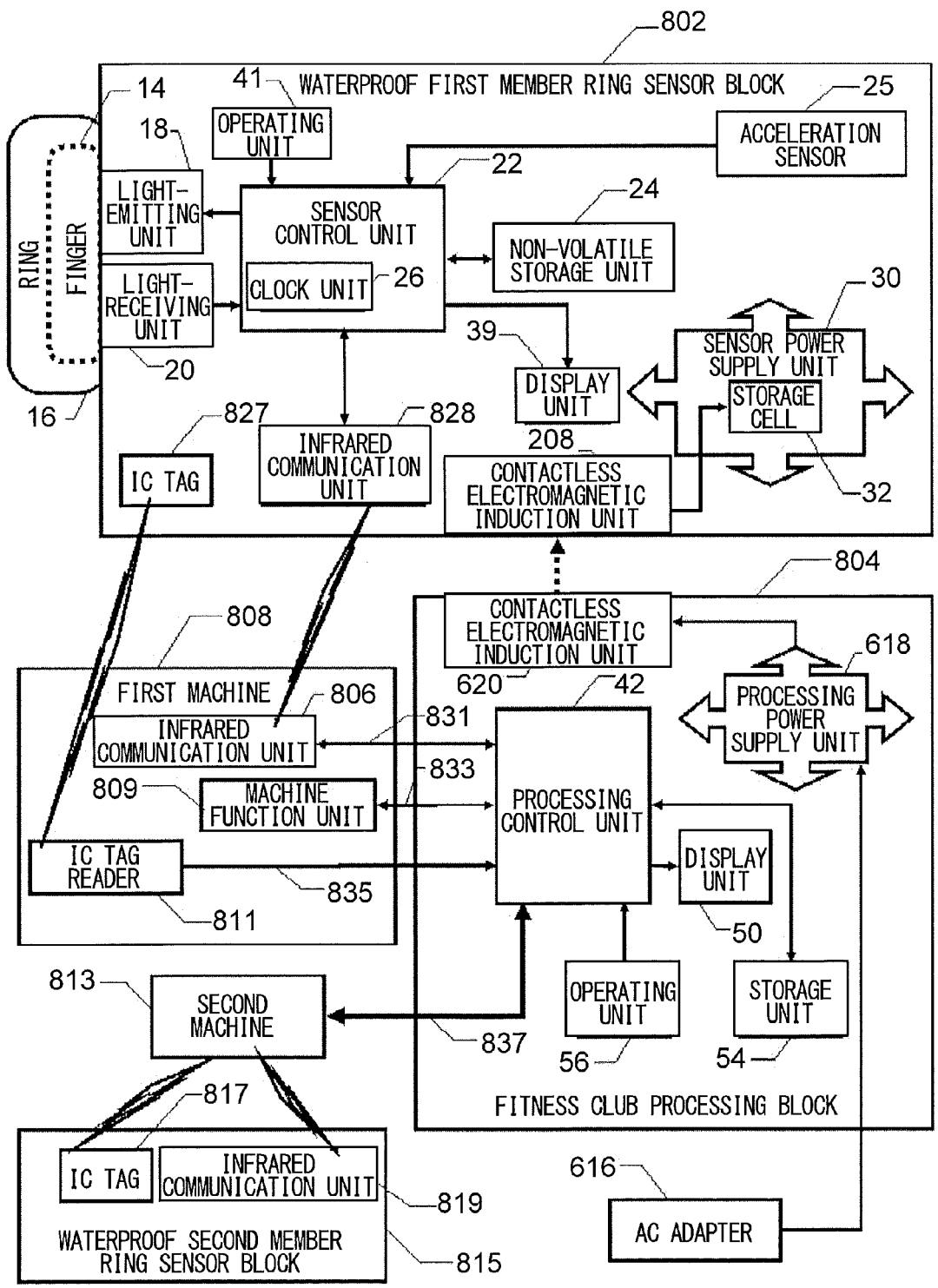
FIG. 17 is a block diagram showing Example 9 of the present invention configured as a biometric information measurement device.

FIG. 17 is a block diagram showing Example 9 of the present invention configured as a biometric information measurement device according to an embodiment of the present invention. Example 9 is configured as a biometric information measuring system with which measurements can be made of pulse waves and pulses of a plurality of members training at a fitness center. The oxygen saturation can also be measured in certain configurations. The minimum units include a first machine 808 having a waterproof first member ring sensor block 802 that can be attached to a finger 14 of a first member, a fitness center processing block 804, and an infrared communication unit 806 for receiving biometric information transmitted from an infrared communication unit 828 in the waterproof first member ring sensor block 802. The first machine 808 can be, e.g., a running machine having a machine function unit 809 composed of a drive unit and a control unit for the running machine. The machine function unit 809 stores the machine ID unique to the machine. Because most of the detailed configuration of Example 9 in FIG. 17 is similar to Example 1 in FIG. 1 and to Example 10 in FIG. 10, the components common to all of them are denoted by the same reference numerals, and further description has been omitted.

The waterproof first member ring sensor block 802 has an IC tag 827 storing the sensor ID for the waterproof first member ring sensor block 802. Whether or not the waterproof first member ring sensor block 802 is attached to a finger 14 of a member is inputted using the operating unit 56 in the fitness center processing block 804, and stored in a storage unit 54. The input is performed, for example, when the waterproof first member ring sensor block 802 is distributed to a member who has recently joined the fitness center. The first machine 808 has an IC tag reader 811 for reading the sensor ID on the IC tag 827. When the sensor ID on the IC tag 827 is read by the IC tag reader 811, it is detected that the first member wearing the waterproof first member ring sensor block 802 is accessing the first machine 808 for training, and short-range communication between the infrared communication units 828, 806 is triggered.

The infrared communication unit 806, the machine function unit 809, and the IC tag reader 811 in the first machine 808 are able to communicate with the processing control unit 42 in the fitness center processing block 804, respectively, via communication lines 831, 833, and 835. The sensor ID read by the IC tag reader 811, the machine ID stored by the machine function unit 809, and the biometric information received by the infrared communication unit 806 are transmitted via this communication to the processing control unit 42.

A second machine 813 can be, e.g., a bicycle-type ergometer used by a second member to which a waterproof second member ring sensor block 815 has been attached. Short-range communication is established with the second machine 813 via an IC tag 817 and an infrared communication unit 819. The second machine 813 essentially has the same configuration as the first machine except for the machine function unit. Because the configuration of the waterproof second member ring sensor block 815 is essentially the same as that of the waterproof first member ring sensor block 802, illustration of the internal components and further description have been omitted. In FIG. 17, the communication lines between the processing control unit 42 and the infrared communication unit, the machine function unit, and the IC tag reader in the second machine 813 are denoted for the sake of simplicity by a single thick line 837. The communication format is similar to the first machine 808. In FIG. 17, the processing control unit 42 is connected to the infrared communication unit 806, the machine function unit 809, and the IC tag reader 811, respectively, via dedicated communication lines 831, 833, 835. This configuration is provided in order to simplify the description. In reality, wired communication can be performed in time-division manner in accordance with a communication system using a single communication cable.

In this configuration, for example, when the first member wearing the waterproof first member ring sensor block 802 accesses the second machine 813 for training and when the second member wearing the waterproof second member ring sensor block 817 accesses the first machine 808 for training, the IC tag 827 of the first member is identified by the second machine 813, and the IC tag 817 of the second member is identified by the first machine 808. When various members train using different types of machines at a fitness center, it can thereby be identified who is training on which machine, and to whom the biometric information being collected by the fitness center processing block 804 via infrared communication belongs. Thus, biometric information for each individual obtained during training on the various types of machines can be transmitted to the processing control unit 42.

In order to simplify the description, only two machines and two waterproof member ring sensor blocks are shown in FIG. 17. In reality, a plurality of different types of machines are installed in a fitness center. The machines do not have to be different types of machines. A plurality of the same type of machine can be provided. Even when the same type of machine is provided, the machine IDs in the machine function units are all different so that each machine can be identified. The "machines" do not have to be used for training purposes. Personal chair-type machines can be provided to allow members to rest. These personal chair-type machines do not have a training function but do have a unique machine ID. Thus, when a member is resting in one of these machines, biometric information from the member in a resting state is transmitted to the processing control unit 42. There does not have to be a same number of machines and members. When the fitness center is empty, the number of machines is greater than the number of distributed waterproof member ring sensor blocks. When the fitness center is crowded, the number of distributed waterproof member ring sensor blocks is greater than the number of machines. In Example 9, there is one-to-one communication between waterproof member ring sensor blocks and machines even when the number of members is greater.

Figure 18:
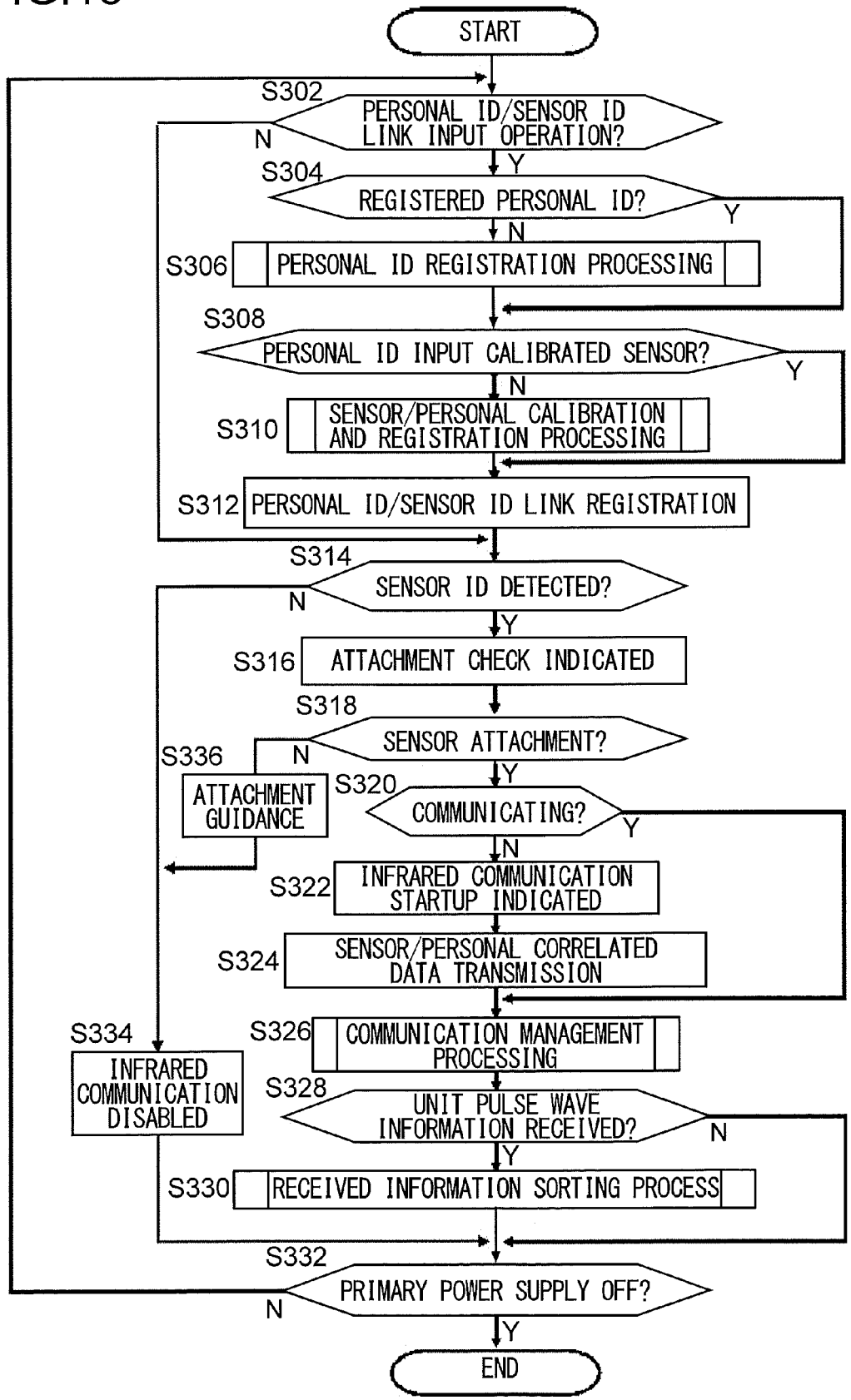
FIG. 18 is a flowchart showing the functions of the processing control unit in Example 9.

FIG. 18 is a flowchart showing the functions of the processing control unit 42 in Example 9 of the invention in FIG. 17. The flow is started when the primary power supply for the fitness center processing block 804 is turned on. When the flow has started and a member is admitted to the fitness center, a check is made in Step S302 as to whether or not an operation has been newly performed to input personal ID/sensor ID correlation information in regard to which waterproof member ring sensor block has been distributed to the member.

When personal ID/sensor ID correlation information has been entered in Step S302, the flow advances to Step S304 where a check is made as to whether or not the entered personal ID has been registered. When the personal ID has not been registered, the personal ID registration process is performed in Step S306, and the flow advances to Step S308. When it has been confirmed in Step S304 that the personal ID has been registered, the flow advances directly to Step S308.

In Step S308, the sensor block is calibrated with the individual based on the sensor ID and personal ID inputted in Step S302, and a check is made as to whether or not the resulting calibration data has been registered. When the data has not been registered, the flow advances to Step S310 where the combination of sensor block and person is calibrated and the resulting calibration data is registered. The flow then proceeds to Step S312. When it has been confirmed in Step S308 that the sensor block has registered calibration data, the flow advances directly to Step S312. In Step S312, the personal ID/sensor ID correlation information inputted in Step S302 is registered. This registration is retained until the person returns the sensor block and quits the fitness center.

Next, in Step S314, a check is made as to whether the IC tag reader has detected a new sensor ID from the ID tag in any of the machines. Because personal ID/sensor ID correlation information is registered in Step S312, this is a check to check whether or not the personal ID has been obtained. When the sensor ID has been detected, the flow advances to Step S316 where the sensor block is instructed to check whether or not the sensor block is attached to a finger of the member. This instruction is given via the infrared communication units 806, 828. Next, in Step S318 a check is made as to whether or not the sensor block is attached to a finger of the member. When attachment has been confirmed, the flow advances to Step S320 where a check is made as to whether infrared communication has already been established. When communication has not yet been established, the flow advances to Step S322 where an instruction is issued to initiate infrared communication. In Step S324, the correlation data for the sensor/person combination is transmitted to the sensor block, and the flow advances to Step S326. When it has been confirmed in Step S320 that infrared communication has been established, the flow advances directly to Step S326. Thus, in Example 9, infrared communication is triggered by detection of an IC tag. The measurement is triggered on the sensor blocks.

In Step S326, the management processing is performed related to infrared communication between the fitness center processing block 804 and the various machines that have established communication via the processing described above. The flow then proceeds to Step S328 where a check is made as to whether or not unit pulse wave information has been received from the sensor block via the machine based on the management processing. When unit pulse wave information has been received, the received information organization process is performed in Step S330, and the flow advances to Step S332. The received information organization process in Step S330 can be understood in greater detail by reinterpreting FIG. 16. Here, "running/resting state" in Step S278 and Step S84 of FIG. 16 is interpreted to mean "machine."

When a sensor ID has not been detected in Step S314, the flow advances to Step S334 where infrared communication is disabled. The flow then proceeds to Step S332. When it has not been confirmed in Step S318 that the sensor has been attached, the flow advances to Step S336 where attachment guidance is displayed on the display unit 50, and attachment guidance signals are transmitted to the sensor block for display on the display unit 39 of the sensor block. The flow then proceeds to Step S334.

When reception of unit pulse wave information cannot be confirmed in Step S328, the flow advances directly to Step S332. In Step S332, a check is made as to whether or not the primary power supply to the fitness center processing block 804 has been turned off. When it has not been turned off, the flow returns to Step S302 and the loop from Step S302 to Step S334 is repeated. As long as the primary power supply has not been turned off, the fitness center processing block 804 can thereby input personal ID/sensor ID correlation information for new measurements, and respond to the receiving and organizing of unit pulse wave information from a plurality of sensor blocks during the measurement process.

Figure 19:
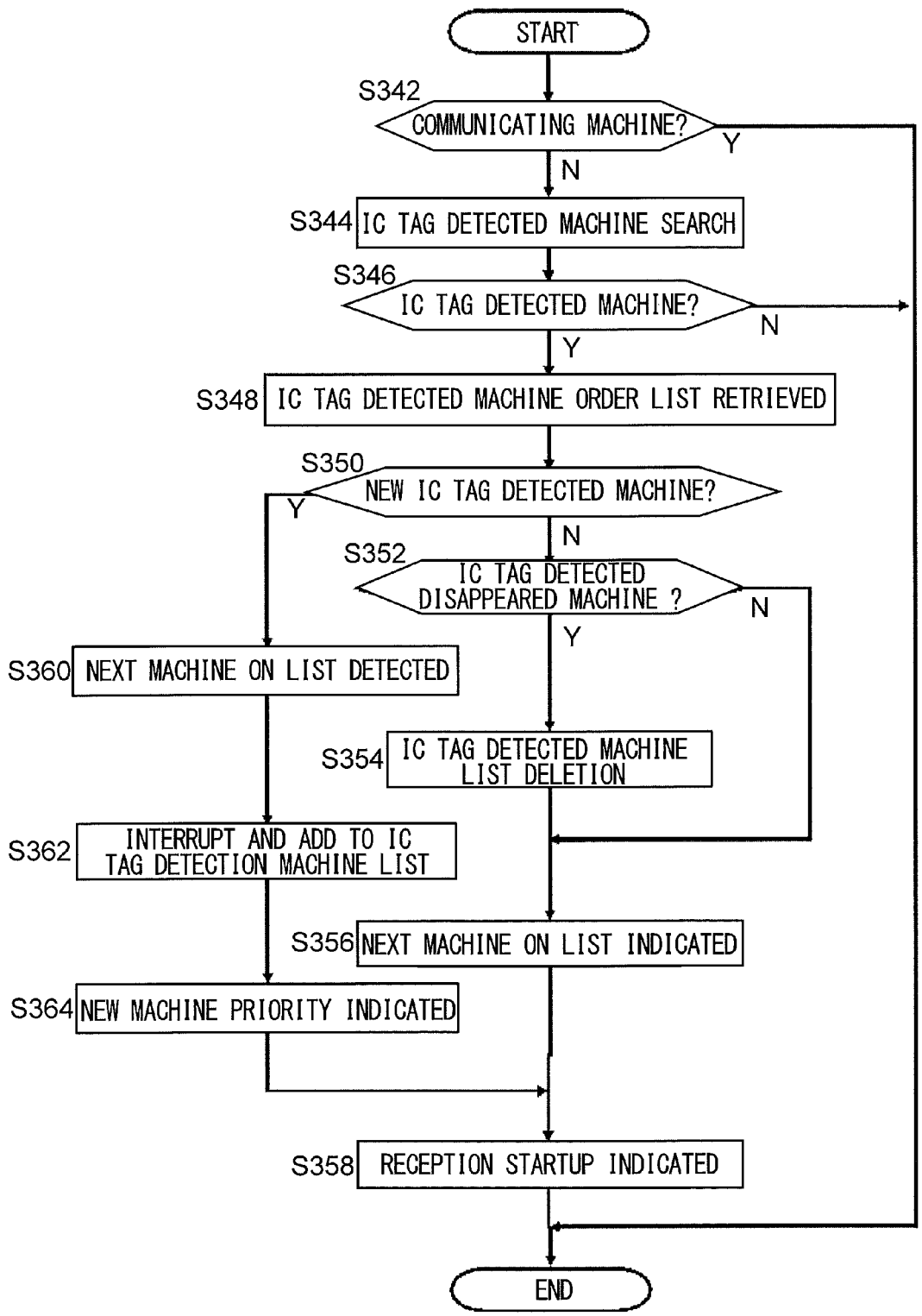
FIG. 19 is a flowchart showing Step S326 in FIG. 18 in greater detail.

FIG. 19 is a flowchart showing the communication management process in Step S326 of FIG. 18 in greater detail. When the flow is started, first, in Step S342, a check is made as to whether or not the processing control unit 42 is communicating with a machine receiving unit pulse wave information from a sensor block. When communicating with a machine, the flow is ended immediately without reception via another machine being started. In other words, when communicating with a machine, communication with the machine is continued until the communication time period allotted for communication has ended.

By contrast, when there is no communication with a machine or when the time period previously allotted for communication with a machine has ended, the flow advances to Step S344 for identifying the machine with the next allotted time period. In Step S344, a sequential search is performed for a machine which has detected the IC tag of a sensor block, and the presence or absence of a response is confirmed. The flow then advances to Step S346 where the presence or absence in the search results of at least one machine which has detected an IC tag is detected. When none of the machines have detected an IC tag, the flow is ended immediately.

When in Step S346 it is confirmed that at least one machine has detected the IC tag of a sensor block, the flow advances to Step S348 where a list is retrieved in which a designation order has been assigned by machines for which previous detection of IC tags has been confirmed. The flow then proceeds to Step S350 where the list retrieved in Step S348 is compared to the results of the check obtained in Step S346 to again perform a check in regard to the presence or absence of machines which are detecting IC tags. When there are no new machines, the flow advances to Step S352 where the list retrieved in Step S348 is compared to the results of the check obtained in Step S346 to check for the presence or absence of machines which have previously detected an IC tag but which are not currently detecting an IC tag. When appropriate, the flow advances to Step S354 where a machine is cleared from the IC tag detecting machine list, and the flow advances to Step S356. When it has been judged in Step S352 that there are no machines which are no longer detecting IC tags, the flow advances directly to Step S356.

In Step S356, the machines are specified in the next order of the machines which have ended their previous communication in accordance with the latest revised designation order for the IC tag detecting machine list. The flow then proceeds to Step S358 where instructions are issued to receive unit pulse wave information from a sensor block via the designated machine. The flow is then ended.

By contrast, when a machine which has newly detected an IC tag is detected in Step S350, the flow advances to Step S360 where the list position of the machine is detected in the next order of the machines which have ended their previous communication, in accordance with the latest revised designation order for the IC tag detecting machine list. The flow then proceeds to Step S362 where the machine which has newly detected an IC tag is inserted in a position prior to the machine detected in Step S360 and added to the list. Next, the flow advances to Step S364 where the new machine added in Step S362 is given priority. The flow then proceeds to Step S358. When there is a plurality of machines newly detecting an IC tag in Step S350, the machine which was the first to detect an IC tag is selected, and the flow advances to Step S360. When the flow next reaches Step S350, another machine is detected as a machine newly detecting an IC tag. Here, the detection conditions for Step S350 can be "a machine which has newly detected an IC tag but which has not yet been given priority in Step S364."

The flow in FIG. 19 is configured based on the assumption that a transmission will be made, all at once, of unit pulse wave information for an amount of data over a relatively unified time of communication with a single machine. However, the embodiment of the present invention is not limited to this example. For example, the communication time period can be time-divided so that the time allotted to a single machine is dramatically shorter. Step S326 of FIG. 18 can be configured so that the flow in FIG. 19 is repeated several times, whereby communication with each machine is performed in parallel. Step S366, in which a check is made as to whether or not the unit parallel communication time period has ended, is added in such a case in place of "END" in FIG. 19, and only in the given instance is the flow ended. The flow returns to Step S342 and Steps S342 to S366 are repeated as long as the unit parallel communication time has not ended.

In a configuration example using the communication management process in FIG. 19 or Step S366, the management of communication time period allotment is performed with greater precision when there is a machine newly detecting an IC tag or a machine ending detection of an IC tag. Alternatively, the communication management process in Step S326 in FIG. 18 can be simplified so that time-division communication is performed on all of the machines in the fitness center during the unit parallel communication time period whether or not an IC tag has been detected and unit pulse wave information is being transmitted from a sensor block. In Example 9, the short-range communication units are infrared communication units. However, there are no particular restrictions on the short-range communication means. Short-range wireless communication units can also be used. Conversely, when necessary, the short-range communication units in Examples 1 through 8 can also be infrared communication units.

The configuration of Example 9 in FIG. 17 to FIG. 19 can be applied to a biometric information measuring system able to measure oxygen saturation based on the pulse waves and pulses of a plurality of swimmers training in a pool as in Example 7 in FIG. 10. Also, the configuration of the pool system in Example 7 can be integrated with the fitness center in Example 9. In order to be able to identify lane rope groups in FIG. 10, lane rope IDs corresponding to the machine IDs of the machine function units 809 in FIG. 17 are provided for the various lane ropes. Also, in order to respond to sensor blocks with IC tags, an IC tag reader is provided in the appropriate location in the lane ropes.

All of the machines shown in FIG. 17 do not have to be configured separately from the fitness center processing block 804. There can be machines that are integrated with the fitness center processing block 804. Also, the various features related to the IC tag do not have to be limited to biometric information measuring systems. They can be applied more broadly to various measurement systems having measurement blocks and processing blocks.

In the examples described above, the present invention is configured as a biometric measurement device. However, the biometric information can be measured while the person being measured is engaged in everyday physical activities; therefore, the measured biometric information may also be interpreted as being information indicating that the person being measured is in good health. Thus, by monitoring this biometric information within the system or at a remote location via a telephone line, the safety and well-being of runners, people listening to a music player, swimmers, and people training at a fitness center can be monitored. Also, for example, adult children living in the city can monitor elderly parents living alone in their hometown, and elderly neighbors living alone can confirm whether each is in good health and develop a deeper sense of connection. The various features shown in Examples 1 through 9 have general features that can be used where appropriate for the purposes of monitoring others.

Example 10

Figure 20:
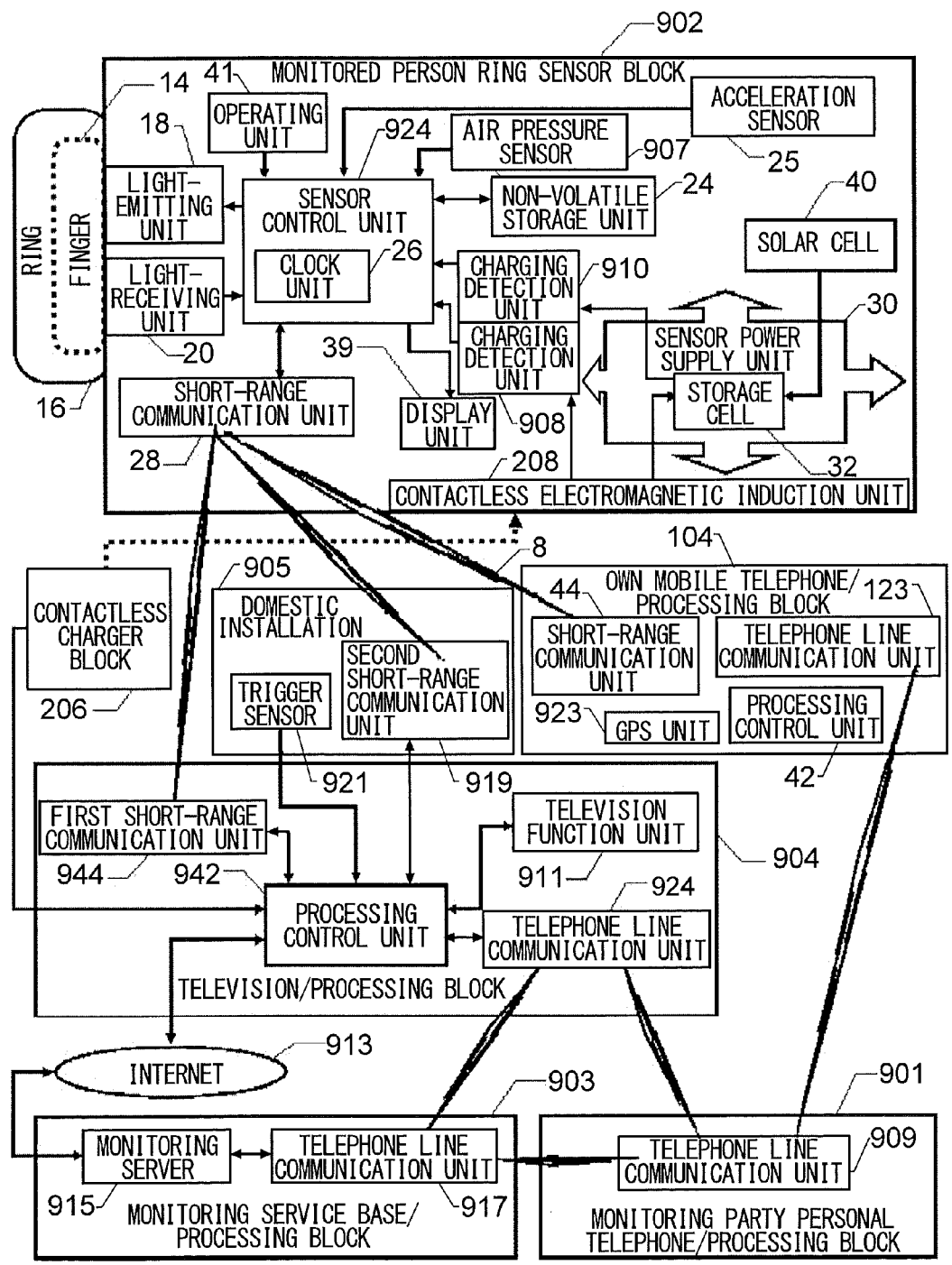
FIG. 20 is a block diagram showing Example 10 of the present invention configured as a biometric information measurement device (suitable for monitoring purposes)

FIG. 20 is a block diagram showing Example 10 of the present invention configured as a biometric information measurement device according to an embodiment of the present invention. This is configured as a monitoring system similar to one described above. The main components in the system configuration of Example 10 in FIG. 20 are arranged as described below in the vicinity of the monitored person such as in their household. The system in Example 10 includes a monitoring-person mobile telephone/processing block 901 possessed by a private monitor such as a family member at a remote location, and a monitoring service base/processing block 903 for the monitoring service provider.

The minimum units of the system configuration arranged in the vicinity of the monitored person include an active-individual ring sensor block 902 that can be attached to a finger 14 of the monitored person during daily activity, an involved-person mobile telephone/processing block 104 in a mobile telephone possessed by the involved active individual, a contactless charger block 206 arranged inside the household of the active individual, a television/processing block 904 serving as the heart of the system in the household of the active individual, and domestic installations 905 such as a bed, bathroom, toilet room, and kitchen installed for communication. The active-individual ring sensor block 902 has a waterproof structure to allow for use in a bathtub and is configured to ensure normal operation up to 60° C.

There is a plurality of domestic installations 905 as mentioned above, but for the sake of simplicity only one is shown in FIG. 20. As described below, the domestic installation 905 is standardized for the bed and bathroom, and simplified for the toilet and kitchen. Also, as described below, a plurality of active-individual ring sensor blocks 902 are provided to allow for alternating charging and use. In this configuration, two sensor blocks are prepared: one for bedtime use and one for daily activity. The one for bedtime use allows for continuous long-term monitoring of pulse wave information, and thus has a large storage capacity. The one for daily activity at least allows for detection of the presence or absence of a pulse for monitoring purposes. It has a relatively small storage capacity able to continuously measure pulse wave information for a relatively short period of time such as while bathing. The active-individual ring sensor blocks 902 for bedtime use and for daily activity will be described in greater detail below.

As mentioned above, the detailed configuration of the various components in Example 10 in FIG. 20 is very similar to those from Example 1 in FIG. 1 to Example 9 in FIG. 17. Therefore, most of them are denoted by the same reference numerals, and further description has been omitted unless otherwise necessary. The detailed configuration of the similar blocks has also been partially omitted from the drawing. For example, the detailed configuration of the involved-person mobile telephone/processing block 104 and the monitoring-person mobile telephone/processing block 901 in FIG. 20 are essentially the same as the mobile telephone/processing block 104 in Example 2 in FIG. 5, but most of the detailed configuration has been omitted from FIG. 20.

The active-individual ring sensor block 902 in Example 10 in FIG. 20 has a configuration which is essentially the same as, e.g., Example 7 in FIG. 10, but it also has an air pressure sensor 907. An air pressure sensor 907 has been proposed in which, e.g., the distortion in a diaphragm due to differences in air pressure is detected by a piezoelectric element. This structure, which is a micro-electromechanical system (MEMS), is mounted in the active-individual ring sensor block 902. The air pressure sensor 907 detects changes in the air pressure when the active individual opens a door to a room in the residence and enters or exits, and changes in the air pressure when the active individual goes between the first floor and second floor of the residence. The sensor control unit 922 is triggered by the changes in air pressure detected by the air pressure sensor 907, measures pulse waves using the light-emitting unit 18 and the light-receiving unit 20, and transmits the measurement results from the short-range communication unit 28. Separately from the trigger of the air pressure sensor 907, the clock unit 26 periodically (e.g., once every ten minutes) generates a periodic trigger signal. The sensor control unit 922 performs a pulse wave measurement using the light-emitting unit 18 and the light-receiving unit 20, and transmits the measurement results from the short-range communication unit 28 each time a periodic trigger signal is received. As described below, the sensor control unit 922 also performs a pulse wave measurement using the light-emitting unit 18 and the light-receiving unit 20, and transmits the measurement results from the short-range communication unit 28 each time an external trigger signal is received such as a trigger signal from a trigger sensor outside of the active-individual ring sensor block 902.

The active-individual ring sensor block 902 of Example 10 in FIG. 20 has a charging detection unit 908 for detecting whether or not the active-individual ring sensor block 902 is located in the contactless charging block 206 and is in the charging state based on the state of the contactless electromagnetic induction unit 208. The charging detection unit 908 also includes a charge complete state. It decides whether or not the active-individual ring sensor block 902 is located in the contactless charger block 206, and transmits the results of the decision to the sensor control unit 922. It can also be decided on the contactless charger block 206 side whether or not the active-individual ring sensor block 902 is located in the contactless charger block 206 and is charging. The results of the decision are transmitted to the processing control unit 942 in the television/processing block 904. The active-individual ring sensor block 902 in Example 10 also has a charge monitoring unit 910 for monitoring the voltage of the storage cell 32. It monitors charge completion and battery depletion, and transmits results to the sensor control unit 922.

As in Example 2 shown in FIG. 5, the pulse wave measurement signals transmitted from the short-range communication unit 28 are received by the short-range communication unit 44 in the involved-person mobile telephone/processing block 104. When normal pulse waves are received, the results are transmitted by automatic email from the telephone line communication unit 123 to the telephone line communication unit 909 in the monitoring-person mobile telephone/processing block 901. When the only purpose is monitoring, the detection of a normal pulse in the pulse wave monitoring signals is sufficient as good-health information. When necessary, the detection precision and amount of information can be lower than situations in which healthcare is provided. By receiving email information, the fact that the active individual is in good health can be monitored from a remote location by the monitoring person. The involved-person mobile telephone/processing block 104 in the monitoring system does not function simply as a portion of a household monitoring system. When the active individual goes out, monitoring can be performed using the mobile telephone email function as long as a charged active-individual ring sensor block 902 is attached and the involved-person mobile telephone/processing block 104 is being carried.

Because, as described above, the television/processing block 904 is the main component in the household monitoring system for the active individual, it has a first short-range communication unit 944 and a telephone line communication unit 924 in addition to the original television function unit 911. The processing control unit 942 controls these configurations. The first short-range communication unit 944 receives measurement results from the short-range communication unit 28 in the active-individual ring sensor block 902 when the active individual is watching television and within the communication range of the first short-range communication unit 944. The processing control unit 942 performs monitoring analysis based on the measurements results of the received pulse wave information, and the results of the analysis are transmitted automatically by email from the telephone line communication unit 924 to the telephone line communication unit 909 in the monitoring-person mobile telephone/processing block 901. The monitoring person can thereby learn that the monitored active individual is in good health via the television/processing block 904.

The processing control unit 942 also automatically transmits the monitoring analysis results to the monitoring server 915 in the monitoring service base/processing block 903 via the internet 913 which is always connected. In order to avoid excessive data collection from the plurality of clients at the information monitoring service base, transmission is limited to abnormal monitoring results unlike the email transmissions to the monitoring-person mobile telephone/processing block 901. The monitoring service base/processing block 903 stores and manages received monitoring analysis results, dispatches monitoring personnel who are always on standby in the case of an urgent situation, and automatically transmits by email the received monitoring analysis results via the telephone line communication unit 917 to the telephone line communication unit 909 of the monitoring-person mobile telephone/processing block 901 according to contract. In addition, emergency telephone contact is conducted from the monitoring service base/processing block 903 to the monitoring-person mobile telephone/processing block 901. Any monitoring target abnormalities can thereby be reported to the monitoring person via the monitoring service base/processing block 903. In this system, redundant monitoring analysis results having the same content and based on the same information source is received by email from the active-individual ring sensor block 902. In order to avoid complexity in this situation, the monitoring party mobile telephone/processing block 901 can be set to accept only the most recent information received and automatically discard older information based on the time stamp when identical content has been confirmed.

The domestic installations 905 are placed in strategic locations in the household such as the bed, bathroom, toilet, and kitchen. They have a second short-range communication unit 919 controlled by the processing control unit 942 which can receive pulse wave information from the active-individual ring sensor block 902 attached to a finger 14 of the monitored person when the monitored person is inside the residence. The domestic installations 905 also have a trigger sensor 921.

The trigger sensor 921, for example, can be the lid of the bathtub in the bathroom. Here, a detection signal is generated when the lid is opened. In the bed, the trigger sensor is a weight sensor. When the monitored person lies down on the bed, the additional weight generates a detection signal. The processing control unit 942 transmits sends a trigger signal to the active-individual ring sensor block 902 from the second short-range communication unit 919 based on these detection signals, and a pulse wave measurement is performed using the light-emitting unit 18 and the light-receiving unit 20. The configuration described above is for a standard domestic installation 905. In the simplified configurations for the toilet and kitchen, the trigger sensor 921 is omitted. In the simplified configuration, the second short-range communication unit shared by the domestic installations is installed in the television/processing block 904. Only an antenna connected to the communication unit is installed in the domestic installation 906. These are described below in greater detail.

In addition to what is described above, the trigger for a pulse wave measurement can be performed by sending a request signal from the telephone line communication unit 909 in the monitoring mobile telephone/processing block 901. Here, the request signal is transmitted from the telephone line communication units 909, 123 to the involved-person mobile telephone/processing block 104, and transferred to the active-individual ring sensor block 902 via the short-range communication units 44, 28. When a measurement is triggered by a request signal and monitoring result signals have been transmitted to the monitoring-person mobile telephone/processing block 901, a response signal based on the request signal is transmitted along with the result signals. In addition to monitoring result signals based on a pulse wave measurement trigger, information such as the attachment state and charge state of the active-individual ring sensor block 902 is also transmitted in response to a request signal. These are described below in greater detail.

Transmission of abnormal monitoring analysis results from the television/processing block 904 to the monitoring service base/processing block 903 is not performed only via the route from the active-individual ring sensor block 902 through a domestic installation 905. In order to avoid complexity, this has been omitted from the drawing. However, Example 10 is configured so that communication can be established from the short-range communication unit 28 in the active-individual ring sensor block 902 via the short-range communication unit 44 in the involved-person mobile telephone/processing block 104, and then via the Internet 913 between the involved-person mobile telephone/processing block 104 and the monitoring server 915 in the monitoring service base/processing block 903. Support service can thereby be received from the monitoring service base/processing block 903 during an abnormality, even when the active individual is not in communication range with the first short-range communication unit 944 or the second short-range communication unit 919 controlled by the television/processing block 904. When the active individual has gone out, the monitoring service base/processing block 903 identifies the destination based on information from the GPS unit 923 in the involved-person mobile telephone/processing block 104 so that the nearest monitoring personnel can respond in an emergency.

Figure 21:
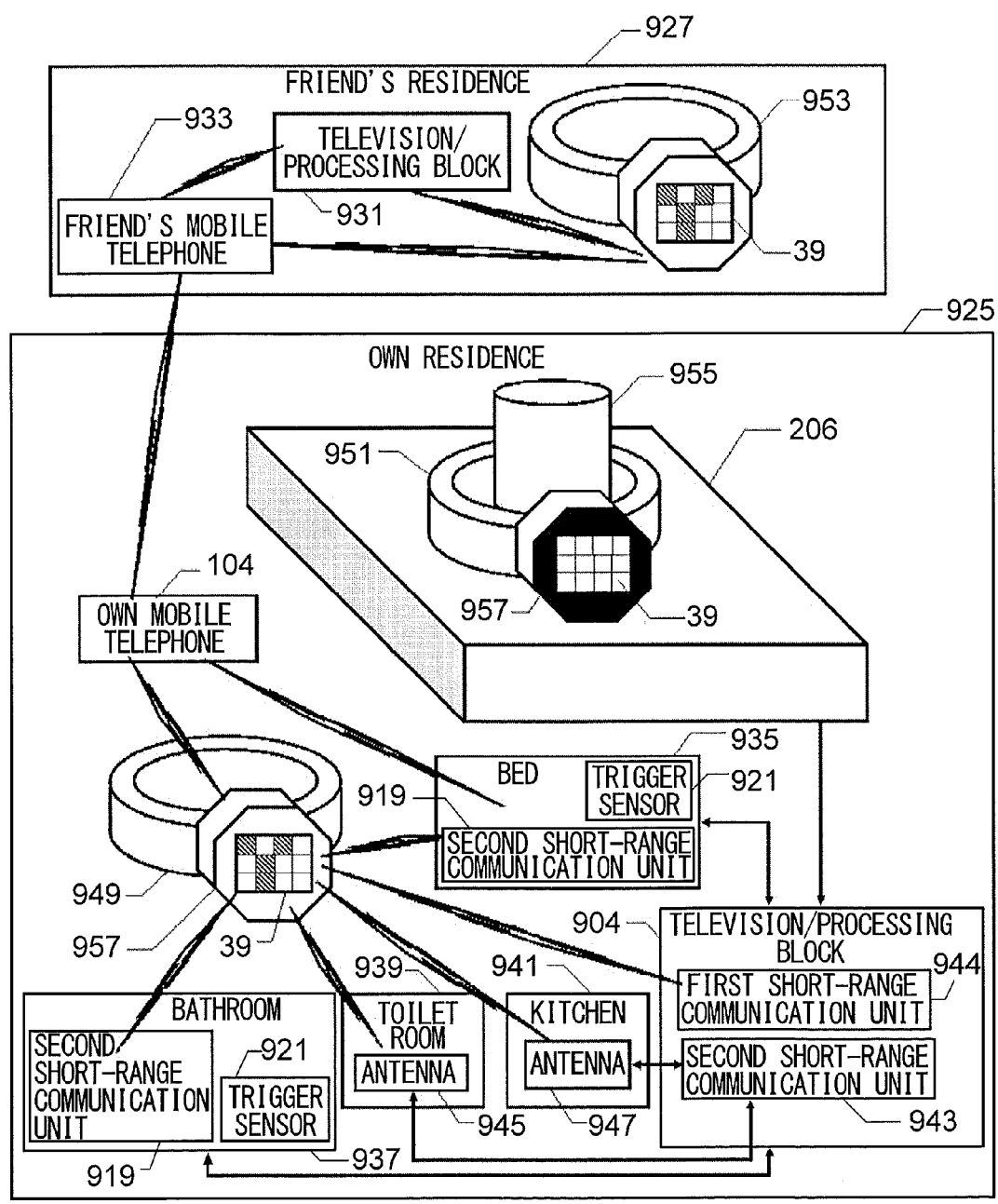
FIG. 21 is a block diagram of a monitoring system using Example 10 in FIG. 20 which allows friends living alone to monitor each other.

FIG. 21 is a block diagram of a monitoring system using Example 10 in FIG. 20 which allows friends living alone to monitor each other. A portion (the monitored person ring sensor block and the contactless charger block) of this drawing is a perspective view. In FIG. 21, the active-individual ring sensor block 902 is both a mid-activity-use ring 949 and a bedtime ring 951. When the former is being used, the latter has been placed on the contactless charger block 206 and is being charged. The system at a friend's residence 927 is similar to the one at the involved-person's residence (home) 925. For the sake of simplicity, the configuration at the friend's residence 927 has been omitted from the drawing except for the mid-activity-use ring 953 serving as the active-individual ring sensor block 902, the television/processing block 931, and the friend's mobile telephone 933. In the following description, the mid-activity-use ring 949 and the bedtime ring 951 are appropriately referred to merely as the active-individual ring sensor block 902.

Also, the monitoring-person mobile telephone/processing block 901 and the monitoring service base/processing block 903 are structural elements of the system but have been omitted from FIG. 21. In addition, because in FIG. 21 the internal configurations of the television/processing blocks 904, 931 in the involved-person's residence (home) 925 and the friend's residence 927 as well as the mobile telephone/processing blocks (involved-person's mobile telephone 104, friend's mobile telephone 933) are the same as those in FIG. 20, the details not required in the description have been omitted from the drawing. Also, the structural components depicted in FIG. 21 that are the same as those in FIG. 20 are denoted by the same reference numerals, and further description has been omitted unless necessary.

A plurality of domestic installations are specifically depicted in FIG. 21. A bed 935 and bathroom 937 are standard installations, and both have a second short-range communication unit 919 and trigger sensor 921. As described earlier, the trigger sensor 921, for example, can be the lid of the bathtub in the bathroom 937. Here, a detection signal is generated when the lid is opened. The processing control unit 942 in the television/processing block 904 transmits from the second short-range communication unit 919 a trigger signal to the short-range communication unit 28 in the mid-activity-use ring 949 or bedtime ring 951 serving as the active-individual ring sensor block 902 based on this. In the bed 935, the trigger sensor 921 is a weight sensor. When the monitored person lies down on the bed 935, the additional weight generates a detection signal. A toilet 939 and kitchen 941 both have simplified domestic installations in which the trigger sensor 921 has been omitted. In the simplified configuration, the second short-range communication unit 943 shared by the domestic installations is installed in the television/processing block 904. Only an antenna 945, 947 connected to the second short-range communication unit 943 is installed in each of the toilet 939 and the kitchen 941. The trigger to transmit monitoring result signals from measurements performed by the simplified domestic installations is spontaneously generated by the clock unit 26 or air pressure sensor 907 in the active-individual ring sensor block 902.

The following is a description of the mutual monitoring of each other by close friends, and the alternating use and charging of the mid-activity-use ring 949 and bedtime ring 951 based on FIG. 21. First, in the mutual monitoring performed by close friends, involved-person monitoring result signals from the mid-activity-use ring 949 are automatically transmitted to the friend's mobile telephone 933 via the involved-person's mobile telephone 104 according to a trigger signal at the times set by the close friends in the clock unit 26, and the results are transferred to the friend's mid-activity-use ring 953 and displayed on the display unit 39. The display unit 39 is a portion of block 12, and it is assigned in advance which close friend will be displayed. For example, the possessor of the mid-activity-use ring 949 is designated on the display unit 39 in the second column from the left and the second line from the top. When the pulse detected by the mid-activity-use ring 949 indicates good health, good health is displayed in the appropriate place on the display unit 39 such as by the cross-hatching in FIG. 21. The friend possessing a mid-activity-use ring 953 is designated on the display unit 39 in the third column from the left and the first line from the top. When the friend's own pulse detected by the mid-activity-use ring 953 indicates good health, good health is similarly displayed in the appropriate place on the display unit 39 such as by the cross-hatching in FIG. 21. At the same time, the friend's monitoring result signals from the mid-activity-use ring 953 are automatically transmitted via the friend's mobile telephone 933 to the involved-person's mobile telephone 104, and the results are transferred to the mid-activity-use ring 949 and displayed on the display unit 39. As in the case of the friend's mid-activity-use ring 953, the mid-activity-use ring 949 indicates on the display unit 39 that the friend is in good health and the involved person is in good health. The example in FIG. 21 allows up to twelve close friends to monitor each other.

The following is a description of the alternating use and charging of the mid-activity-use ring 949 and the bedtime ring 951. In FIG. 21, as explained above, the mid-activity-use ring 949 is being used in the involved-person's residence (home) 925, and the bedtime ring 951 has been placed on the contactless charger block 206 and is being charged. In order to avoid complexity, the finger on which the mid-activity-use ring 949 has been placed has been omitted from the drawing.

The contactless charger block 206 has a core unit 955 for positioning the mid-activity-use ring 949 or the bedtime ring 951 during placement and for generating an electromagnetic field for induction. During charging, as shown in FIG. 21, the mid-activity-use ring 949 or the bedtime ring 951 is inserted over the core unit 955 and placed on the contactless charger block 206. As shown in FIG. 21, the core unit 955 is long enough to accommodate a plurality of stacked active-individual ring sensor blocks 902. A contactless charger block 206 having this core unit 955 can effectively and reliably charge sensor blocks. It also prevents the active-individual ring sensor block 902 not in use from becoming lost. (In FIG. 21, the bedtime ring 951 is placed on the charger block.) The contactless charger block 206 detects whether or not the active-individual ring sensor block 902 placed on the charger block is being charged and whether or not the charging has been completed based on the change in electric current, and it notifies the television/processing block 904 of this over a wire. The television/processing block 904 can thereby ascertain the charging status of the active-individual ring sensor block 902 via wired communication with both the active-individual ring sensor block 902 and the contactless charger block 206.

In the system in Example 10 in which a plurality of active-individual ring sensor blocks 902 is alternatingly charged and used, monitoring can be performed without interruption, and one of the sensor blocks can be effectively charged while the other is being used. By providing different types of active-individual ring sensor blocks 902 adapted to different monitoring purposes, such as with the mid-activity-use ring 949 and the bedtime ring 951, the rings can be naturally replaced and charged according to a daily rhythm. Because this also helps the monitored person not to forget to put on and charge the rings, more reliable monitoring can be performed. Because, as mentioned above, the bedtime ring 951 is able to check the health status of the monitored person by continuously monitoring over a prolonged period of time the pulse waves of the monitored person while sleeping, its memory capacity is set to be larger than that of the mid-activity-use ring 949. Because the mid-activity-use ring 949 is primarily configured to monitor daily activity, its configuration can be simplified so that only the presence or absence of a pulse can be detected. When continuous measurement of pulse wave information is performed, the continuous measurement can be performed during relatively short periods of time such as during a bath. Therefore, as mentioned above, it may be provided with relatively small memory capacity.

When active-individual ring sensor blocks 902 with different functions are used, such as the daily use ring 949 and the bedtime ring 951, they can be marked "day" and "night" or "for daily activity" and "for bedtime" in an easy to see location. Alternatively, the exterior shape or exterior color of the rings can be different. For example, the color surrounding the display unit 39 on the front of active-individual ring sensor block 902 arranged in the portion 957 typically corresponding to a gemstone in an ordinary ring can be a light color such as white in the case of the mid-activity-use ring 949 and a dark color such as black in the case of the bedtime ring 951, as in FIG. 21.

Figure 22:
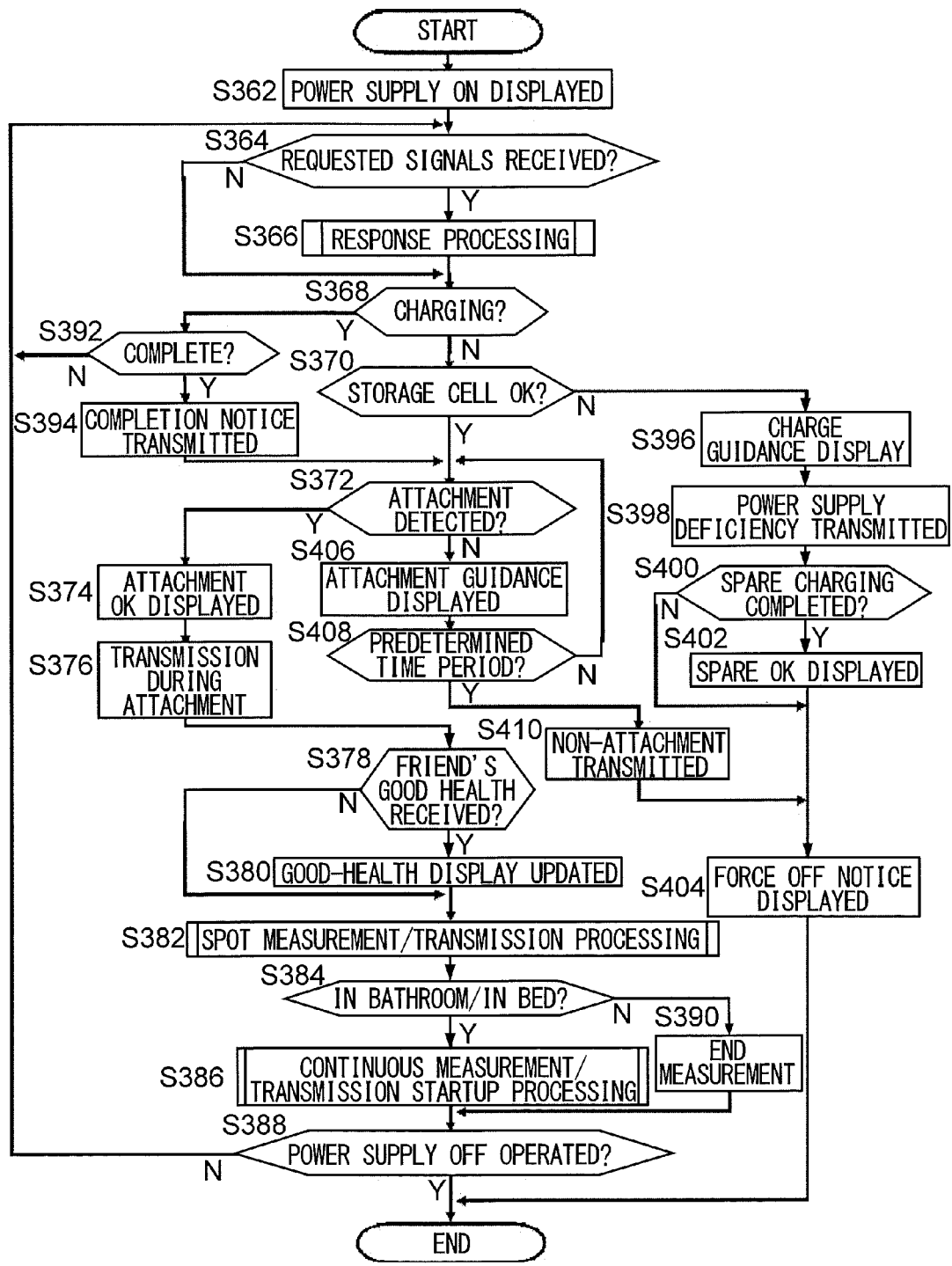
FIG. 22 is a flowchart showing the operation of the sensor control unit in Example 10.

FIG. 22 is a flowchart showing the operations of the sensor control unit 922 in Example 10 in FIG. 20. The flow is started when the power supply switch for the operating unit 41 is turned on. In Step S362, an instruction is issued to indicate on the display unit 39 that the power supply has been turned on. In Step S364, a check is made as to whether or not a measurement request signal has been received from the monitoring-person mobile telephone/processing block 901 via the involved-person's mobile telephone 104 and the short-range communication unit 28. When a request signal has been received, the flow advances to Step S366. The response process for responding to the monitoring-person mobile telephone/processing block 901 based on the request signal is executed, and the flow advances to Step S368. The response process is described below in greater detail. When reception of a request signal has not been detected in Step S364, the flow advances directly to Step S368.

In Step S368, a check is made as to whether or not the active-individual ring sensor block 902 of the involved person has been placed on the contactless charger block 206 and is being charged. This check can be performed by the charging detection unit 908. When it is not being charged, the flow advances to Step S370 where a check is made as to whether or not the charge of the storage cell 32 is sufficient based on information from the charge monitor unit 910. When the charge is sufficient, the flow advances to Step S372 where a check is made as to whether or not the active-individual ring sensor block 902 is attached to a finger 14. When the block has been detected to be attached to a finger, the flow advances from Step S372 to Step S374 where an instruction is issued to display on the display unit 39 that the block is attached. The flow then proceeds to Step S376. In Step S376, the information indicating that the ring is attached is transmitted directly or via a domestic installation 905 to the television/processing block 904. The flow then proceeds to Step S378. When the ring is in reception range at this time, the involved-person mobile telephone/processing block 104 also receives the transmitted information.

In Step S378, a check is made as to whether or not good-health information has been newly received from a friend's active-individual ring sensor block 902 (a friend's mid-activity-use ring 953, or the like). When good-health information has been received, the flow advances to Step S380 where the display in the friend's assigned field on the display unit 39 is updated, and the flow advances to Step S382. When good-health information has not been detected in Step S378 as having been newly received, the flow advances directly to Step S382. In Step S382, the spot measurement/transmission process is executed based on various triggers and the flow advances to Step S384. The spot measurement/transmission process is described below in greater detail.

In Step S384, a check is made as to whether or not a trigger signal has been received based on detection by the trigger sensor 921 in the bathroom 937 or the trigger sensor 921 in the bed 935. When received, the flow advances to Step S386 where the process for initiating continuous measurement and transmission is performed. The flow then proceeds to Step S388 where a check is made as to whether or not the power supply has been turned off. When detection by the trigger sensor 921 in the bathroom 937 or the trigger sensor 921 in the bed 935 has not been confirmed in Step S384, the flow advances to Step S390. An instruction is issued to end the measurement, and the flow advances to Step S388.

When it has been detected in Step S368 that the active-individual ring sensor block 902 of the involved person has been placed on the contactless charger block 206 (including both the charge complete state and the charging state), the flow advances to Step S392 where a check is made as to whether or not the charge has been completed based on information from the charge monitoring unit 910. When completion of the charging has been detected, the flow advances to Step S394 and information indicating that the charging is complete is transmitted directly or via a domestic installation 905 to the television/processing block 904. The flow then advances to Step S372. When the ring is in reception range at this time, the involved-person mobile telephone/processing block 104 also receives the transmitted information. The flow proceeds to Step S372, whereby it is possible to detect whether or not the ring has been removed from the contactless charger block 206 and attached to a finger 14 when the charging of the active-individual ring sensor block 902 has been completed. When the completion of the charging cannot be detected in Step S392, the flow returns to Step S364, and the steps are performed following detection of whether a request signal has been received.

Also, when it cannot be detected in Step S370 that the charging of the storage cell 32 is sufficient, the flow advances to Step S396 where an instruction is issued to display charging guidance on the display unit 39. In Step S398, information indicating an insufficient power supply is transmitted to the television/processing block 904 directly or via a domestic installation 905, and the flow advances to Step S400. In Step S400, a check is made as to whether or not the charging of the spare active-individual ring sensor block 902 has been completed. For example, when the mid-activity-use ring 949 is in use as in FIG. 21, the bedtime ring 951 is the spare active-individual ring sensor block. The check in Step S400 can be performed by transferring information from the functions in Step S392 and Step S394 for the spare monitored person ring sensor block indicating that the charging is complete from the television/processing block 904. When it has been confirmed in Step S400 that charging of the spare monitored person ring sensor block has been completed, the flow advances to Step S402. This information is displayed on the display unit 39, and the flow advances to Step S404. When it cannot be detected in Step S400 that charging of the spare has been completed, the flow advances directly to Step S404. In Step S404, instructions are displayed warning the user that the power supply will be forcibly turned off, and the flow is ended. The power supply is turned off when the flow ends.

When it has not been detected in Step S372 that the mid-activity-use ring sensor block 902 has been attached to a finger 14, the flow advances to Step S406. Attachment guidance is displayed on the display unit 39, and the flow advances to Step S408. In Step S408, a check is made as to whether or not a predetermined period of time has elapsed since the power supply was turned on. When the period of time has not elapsed, the flow returns to Step S372. Steps S372, S406, and S408 are repeated as long as attachment has not been detected and the elapsing of the predetermined period of time has not been detected in Step S372. When it has been detected in Step S408 that the predetermined period of time has elapsed, the flow advances to Step S410. Information indicating that the active-individual ring sensor block 902 has not been attached is transmitted directly or via a domestic installation 905 to the television/processing block 904, and the flow advances to Step S404. When in reception range at this time, the involved-person mobile telephone/processing block 104 also receives the transmitted information. Thus, while attachment guidance is displayed immediately in Step S406, time to attach the ring is provided relative to the transmission of non-attachment information immediately after the power supply has been turned on. After the power has been turned on, Steps S372, S406, and S408 are repeated and a predetermined amount of time is allowed to lapse before execution. This prevents a situation in which there is confusion because the user intends to attach the ring but must do so quickly before non-attachment information is transmitted.

Figure 23:
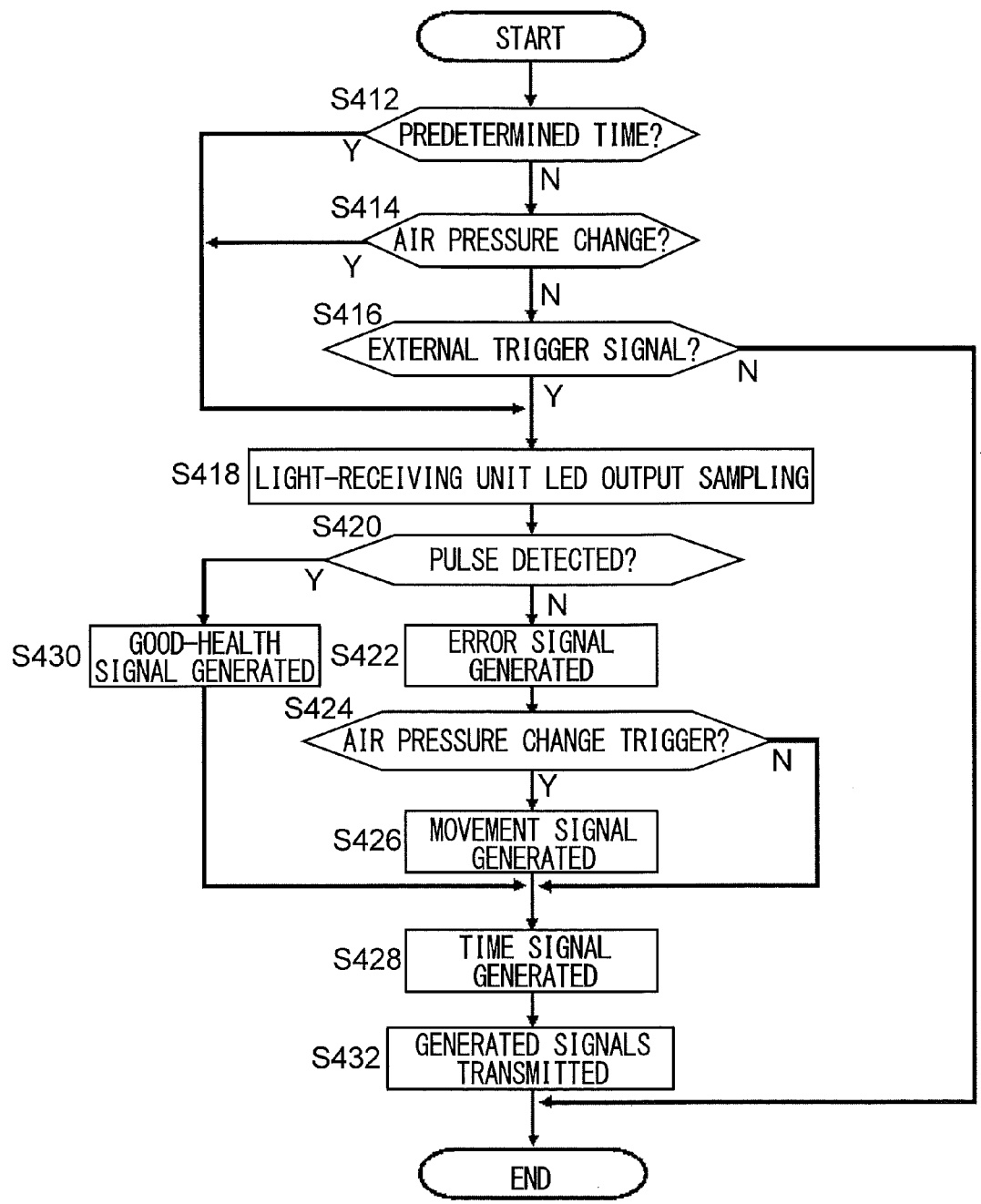
FIG. 23 is a flowchart showing Step S382 in FIG. 22 in greater detail.

FIG. 23 is a flowchart showing the spot measurement/transmission process in Step S382 of FIG. 22 in greater detail. When the flow is started, a check is made in Step S412 as to whether or not a predetermined time has been reached for triggering a measurement based on information from the clock unit 26. When the predetermined time has not been reached, the flow advances to Step S414 where a check is made as to whether or not there has been a predetermined change in air pressure based on information from the air pressure sensor 907. When there has been no change in air pressure, a check is made in Step S416 as to whether or not an external trigger signal has been received by the short-range communication unit 28. The external trigger signal in Step S416 is from a domestic installation 905. Request signals from the monitoring-person mobile telephone/processing block 901 are not included. Request signals are detected in Step S364 of FIG. 22.

When an external trigger signal has not been detected in Step S416, it means trigger signals have not been detected for all of the checklist items, and the flow ends immediately. In other words, in this situation, nothing is performed in Step S382 of FIG. 22. When it has been detected in Step S412 that the predetermined time has been reached, a pressure change has been detected in Step S414, or an external trigger signal has been detected in Step S416, the flow advances to Step S418 where the output from the light-receiving unit 20 is sampled based on time-division light emission from the plurality of LEDs in the light-emitting unit 18. The flow then advances to Step S420 where a check is made as to whether or not a pulse has been detected based on the sampled output. When a pulse cannot be detected, the flow advances to Step S422. A signal indicating an abnormality with the active individual being monitored is generated, and the flow advances to Step S424.

In Step S424, a check is made as to whether or not the trigger was activated by a change in air pressure. When so, the flow advances to Step S426. A signal indicating that the active individual being monitored has moved for some reason is generated, and the flow advances to Step S428. The change in air pressure is assumed to be caused by a door being opened or closed, or the active individual ascending or descending stairs. When the active individual moves, information indicating movement is generated as monitoring signals even when the pulse is not detected. This is not unusual during daily activity. When a pulse has been detected in Step S420, the flow advances to Step S430. A good-health signal is generated, and the flow advances to Step S428. In Step S428, time signals are generated as a time stamp. Afterwards, the flow advances to Step S432 where all of the signals generated in the manner described above are transmitted directly to the television/processing block 904 or via a domestic installation 905. The flow then ends. When in reception range at this time, the involved-person mobile telephone/processing block 104 also receives the transmitted information.

Figure 24:
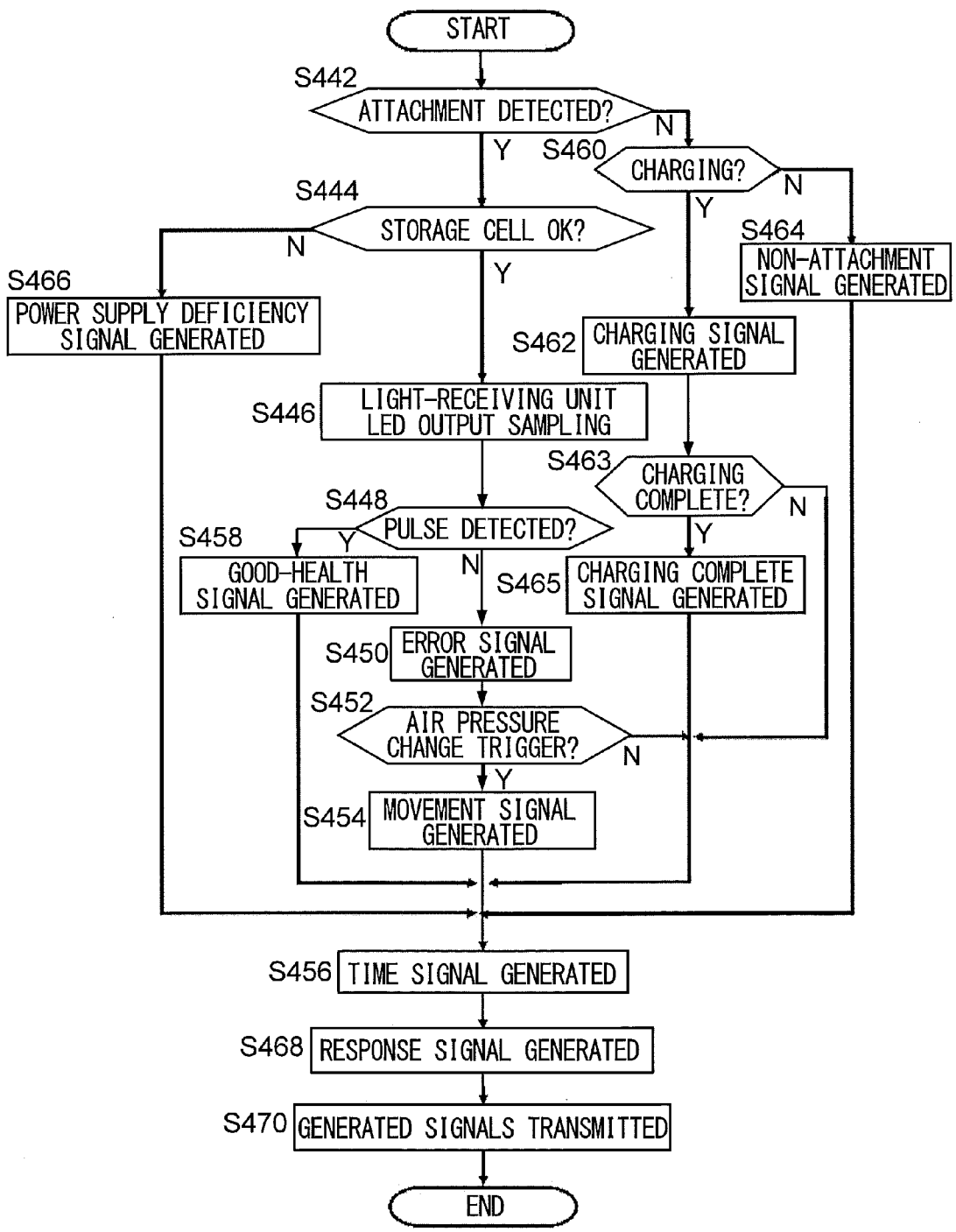
FIG. 24 is a flowchart showing Step S366 in FIG. 22 in greater detail.

FIG. 24 is a flowchart showing the response process in Step S366 of FIG. 22 in greater detail. When the flow is started, a check is made in Step S442 as to whether or not an active-individual ring sensor block 902 has been attached to a finger 14. When attachment has been detected, the flow advances to Step S444 where a check is made as to whether or not the charge of the storage cell 32 is sufficient. When the charge is sufficient, the flow advances to Step S446 where the output from the light-receiving unit 20 is sampled based on time-division light emission from the plurality of LEDs in the light-emitting unit 18. Because the flow from Step S446 to the generation of good-health signals in Step S458 is the same as the flow from Step S418 to Step S430 in FIG. 23, further description has been omitted. In other words, as in FIG. 23, these flows are functions in a state where the active-individual ring sensor block 902 has been attached to a finger 14 and the charge is sufficient.

When attachment of the active-individual ring sensor block 902 to a finger 14 has not been detected in Step S442, the flow advances to Step S460 where a check is made as to whether or not the active-individual ring sensor block 902 has been removed from the finger 14 and placed on the contactless charger block 206 for charging and is being charged. When the sensor block is being charged, the flow advances to Step S462 where a charging signal is generated. The flow then proceeds to Step S463. In Step S463, a check is made as to whether or not the charging has been completed. When completed, a fully charged signal is generated in Step S465 and the flow advances to Step S456. When the charge has not been completed, the flow advances from Step S463 directly to Step S456. When it is not detected in Step S460 that charging is occurring, the flow advances to Step S464. A signal is generated indicating that the active-individual ring sensor block 902 has not been attached to a finger 14, and the flow advances to Step S456. When the active-individual ring sensor block 902 is not attached but is confirmed to have been removed for charging, a non-attachment signal is not generated.

When it cannot be detected in Step S444 that the charge of the storage cell 32 is sufficient, the flow advances to Step S466 where an insufficient power supply signal is generated. The flow then proceeds to Step S456. In the response process in FIG. 24, time signal generation continues in Step S456, a response signal is generated in Step S468, and the flow advances to Step S470. The response signal generated in Step S468 is used to indicate which signals to be transmitted have been generated based on a request signal. In Step S470, as in Step S432 of FIG. 23, all of the generated signals are transmitted to the television/processing block 904 directly or via the domestic installation 905, and the flow is ended. When in reception range at this time, the involved-person mobile telephone/processing block 104 also receives the transmitted information.

Thus, in the response process of Example 10, when the LED output of the light-receiving unit is not sampled in Step S446, the status of the active-individual ring sensor block 902 is checked in a variety of states (charging, non-attachment, insufficient power supply, or the like), and response information is generated. By contrast, in the spot measurement/response process in FIG. 23, information is transmitted unilaterally in response to an automatic trigger, unlike with transmission as a response to an intentional request signal such as in FIG. 24. Therefore, in order to avoid complexity, a configuration is adopted in which the transmission is limited to the information normally used when the LED output of the light-receiving unit is sampled. However, the embodiment of the present invention is not limited to this configuration. For example, all information can be transmitted when a request signal is received or whenever an automatic trigger is activated. In another configuration, selection and transmission of specific information can be intentionally requested using a request signal.

Figure 25:
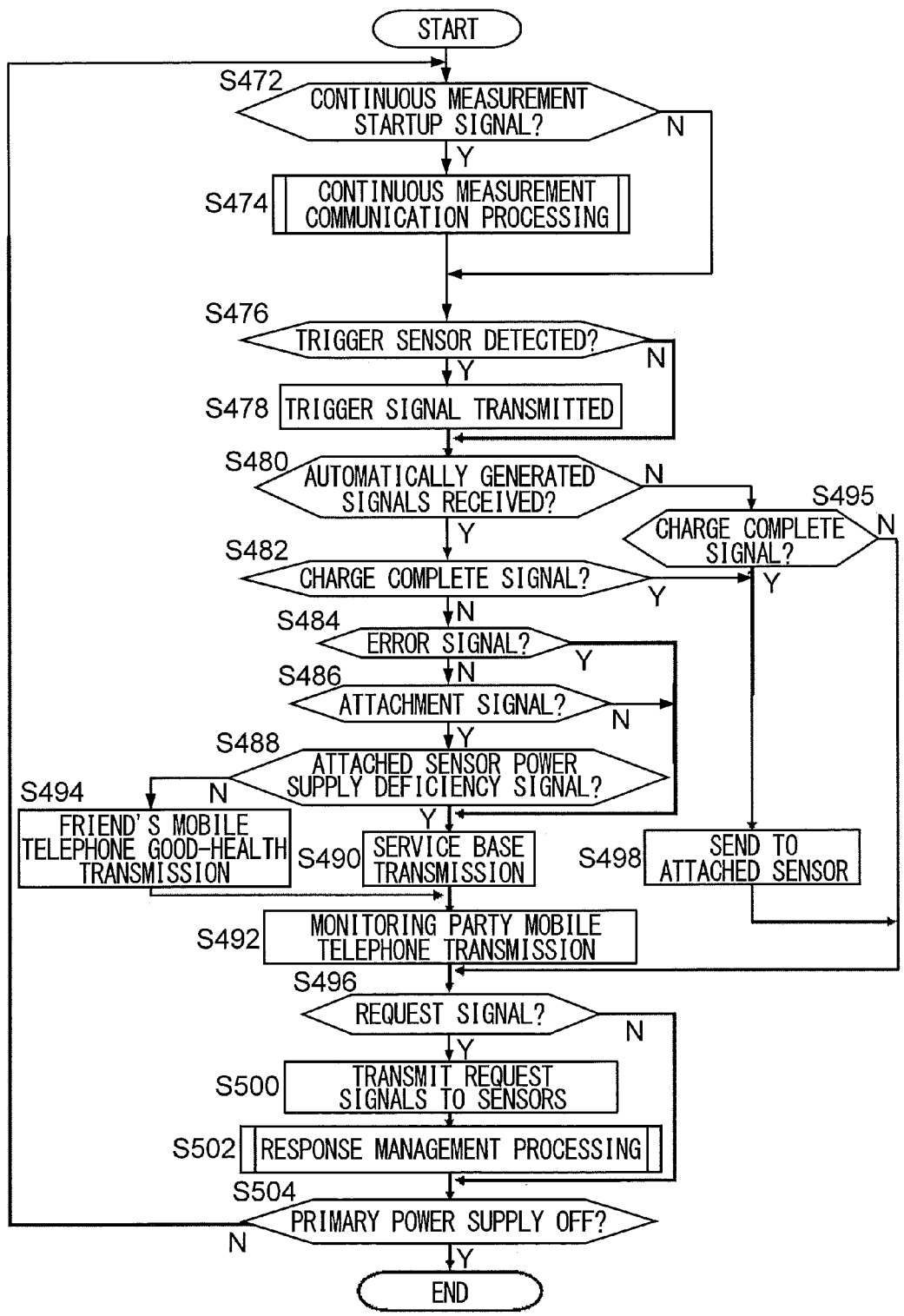
FIG. 25 is a flowchart showing the functions of the processing control unit for the television/processing block in Example 10.

FIG. 25 is a flowchart showing the functions of the processing control unit 942 for the television/processing block 904 in FIG. 20. In FIG. 25, the functions related to ordinary television operations have been omitted, and the functions related to the monitoring system are shown. The flow is started when the primary power supply to the television/processing block 904 is turned on. In Step S472, a check is made as to whether or not a signal indicating initiation of continuous measurement has been received from the active-individual ring sensor block 902. When a signal has been inputted, the flow advances to Step S474. In Step S474, the continuous measurement communication process is executed in a link with the active-individual ring sensor block 902. When this has ended, the flow advances to Step S476. When reception of a continuous measurement startup signal cannot be confirmed in Step S472, the flow advances directly to Step S476.

In Step S476, a check is made as to whether or not a detection signal has been inputted from the trigger sensor 921 in the bathroom 937 or the trigger sensor 921 in the bed 935. When a trigger signal has been inputted, the flow advances to Step S478. This is transmitted to the active-individual ring sensor block 902, and the flow advances to Step S480. When a detection signal from a trigger sensor cannot be confirmed in Step S476, the flow advances directly to Step S480.

In Step S480, a check is made as to whether or not signals generated automatically by the active-individual ring sensor block 902 and not in response to a request signal have been received. When automatically generated signals have been received for whatever reason, the flow advances to Step S482. A plurality of automatically generated signals can be generated in parallel, but these are scrutinized individually in the subsequent steps. First, in Step S482, a check is made as to whether or not a fully charged signal is included in the generated signals that have been received. A fully charged signal is transmitted not by the active-individual ring sensor block 902 attached to a finger 14 and currently in use, but from a active-individual ring sensor block 902 removed from a finger 14 and placed on the contactless charger block 206.

When a fully charged signal is not included in the automatically generated signals that have been received, the flow advances from Step S482 to Step S484, and a check is made as to whether or not an abnormal signal based on a measurement is included in the automatically generated signals that have been received. When an abnormal signal is not included, the flow advances to Step S486 where a check is made as to whether or not the automatically generated signals that have been received include an attachment signal from one of the active-individual ring sensor blocks 902. Because the attachment detected in Step S372 of FIG. 2 is performed repeatedly, the attachment signal ceases as soon as an active-individual ring sensor block 902 has been removed from a finger 14. In other words, an attachment signal is received essentially continuously as long as the active-individual ring sensor block 902 is attached to a finger 14. When an attachment signal is not included in the automatically generated signals whose reception is confirmed in Step S486, it means neither active-individual ring sensor block 902 is attached to a finger 14. Attachment detection as well as transmission and reception of attachment signals are essentially performed continuously as mentioned above, but transmission in Step S376 of FIG. 22 is not normal. For example, the interval for checking on the condition of the monitored person can be set at, e.g., 30-minute intervals. When a non-attachment signal generated in Step S410 of FIG. 22 conflicts with an attachment signal from the other active-individual ring sensor block 902, the latter is given precedent.

When it has been confirmed in Step S486 that an attachment signal is included in the automatically generated signals that have been received, the flow advances to Step S488 where a check is made as to whether or not a signal indicating that the attached active-individual ring sensor block 902 has an insufficient power supply is included in the automatically generated signals that have been received. When an insufficient power supply signal for the attached sensor is not included, the flow advances to Step S490. This information is transmitted to the monitoring service base/processing block 903, and the flow advances to Step S492. When it has been detected in Step S484 that an abnormal signal is included and when it has been detected in Step S486 that an attachment signal is included, the flow advances to Step S490 where this information is transmitted to the monitoring service base/processing block 903. In these situations, normal monitoring cannot be performed. The monitoring service base/processing block 903 responsible for monitoring can take the appropriate action based on this information.

When an insufficient power supply signal for the attached sensor is not included in the automatically generated signals that have been received in Step S488, the flow advances to Step S494. In this situation, the automatically generated signals that have been received are good-health signals confirmed by the fact that the attached active-individual ring sensor block 902 has a sufficient power supply. Thus, the transmission to the friend's mobile telephone 933 in Step S494 indicates that the monitored person is in good health. The flow then proceeds to Step S492. Because friends living alone who are monitoring each other are not responsible for monitoring details other than good-health status, the existence of a good-health signal is all that gets transmitted to the friend's mobile telephone 933. In order to avoid complexity in the communication and information relative to the monitoring service base/processing block 903 as mentioned above, the transmission of good-health signals, which constitutes most of the information, is omitted. Only details concerning situations in which normal monitoring cannot be performed are transmitted.

In Step S492, the received automatically generated signals are transmitted to the monitoring-person mobile telephone/processing block 901 irrespective of the situation, and the flow advances to Step S496. Because the monitoring person is monitoring the monitored person privately, good-health status and circumstances where proper monitoring cannot be performed can be transmitted in detail. When automatically generated signals are not received at all in Step S480, the flow advances to Step S495 where a check is made as to whether or not a fully charged signal have been inputted to the television/processing block 904 via a wire from the contactless charger block 206 on which the active-individual ring sensor block 902 has been placed for charging. When a fully charged signal has been inputted from the contactless charger block 206, the flow advances to Step S498 where the fully charged signal is transmitted to the other active-individual ring sensor block 902 attached to a finger 14 and currently in use. When input of a fully charged signal is not detected, the flow advances from Step S495 directly to Step S496. When an automatically generated signal has not been received in Step S480, the system is either malfunctioning or the system is functioning normally but there is no timing for signal transmission during attachment, and a time period has occurred in which the measurement trigger is not activated. When a fully charged signal has been generated in Step S482, as mentioned above, the active-individual ring sensor block 902 has been removed from the finger 14 and placed on the contactless charger block 206. The flow advances to Step S498 where a fully charged signal is transmitted to the other active-individual ring sensor block 902 attached to a finger 14 and currently in use. The flow then proceeds to Step S496.

In Step S496, a check is made as to whether or not a request signal has been received from the monitoring-person mobile telephone/processing block 901. When a request signal has been received, the signal is transmitted to the various sensors in Step S500, the response management process is performed in Step S502, and the flow advances to Step S504. When reception of a request signal has not been detected in Step S496, the flow advances directly to Step S504. In Step S504, a check is made as to whether or not the primary power supply to the television/processing block 904 has been turned off. When it has been turned off, the flow returns to Step S472. The loop from Step S472 to Step S504 is then repeated to respond to the various conditions related to the monitoring function until the primary power supply has been turned off.

Figure 26:
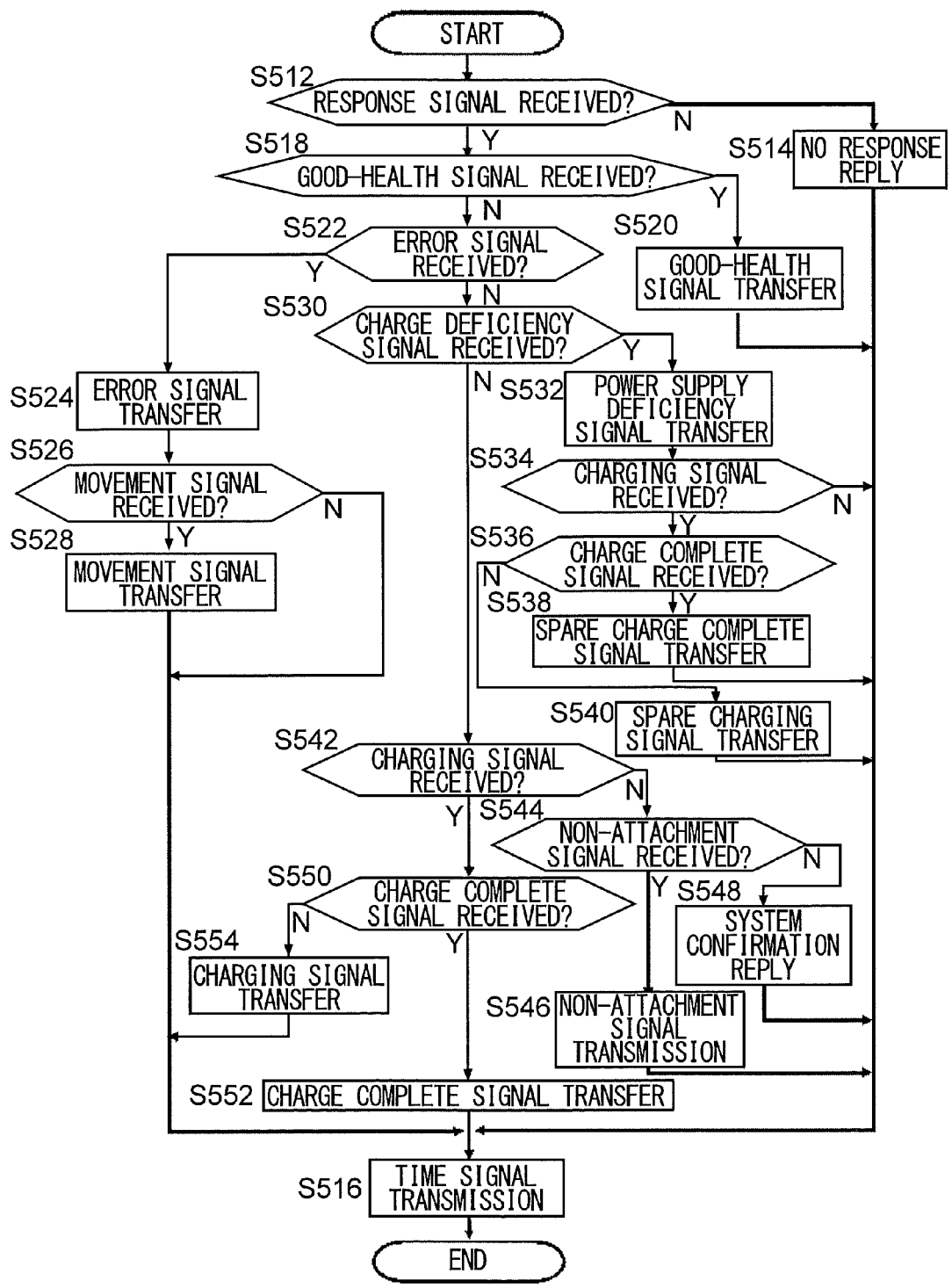
FIG. 26 is a flowchart showing Step S502 in FIG. 25 in greater detail.

FIG. 26 is a flowchart showing the response management process in Step S502 of FIG. 25 in greater detail. When the flow has started, first, in Step S512, a check is made as to whether or not a response signal generated by the active-individual ring sensor block 902 has been received in response to a request signal under any situation. When a response signal has not been received, the flow advances to Step S514. No response is returned to the monitoring-person mobile telephone/processing block 901, and the flow advances to Step S516. When a time signal has been received, this is used in Step S516. When a time signal has not been received, a time signal is generated and transmitted to the monitoring-person mobile telephone/processing block 901. The flow then ends immediately.

When a response signal has been received in Step S512, the flow advances to Step S518 where a check is made as to whether or not a good-health signal has been received from the active-individual ring sensor block 902. When a good-health signal has been received, the flow advances to Step S520. The health signal is transferred to the monitoring-person mobile telephone/processing block 901, and the flow advances to Step S516. In the same manner as above, a time signal is transmitted in Step S516 to the monitoring-person mobile telephone/processing block 901, and the flow is ended. By contrast, when reception of a good-health signal cannot be confirmed in Step S518, the flow advances to Step S522 where a check is made as to whether or not an abnormal signal has been received from the active-individual ring sensor block 902. When an abnormal signal has been received, the flow advances to Step S524. The abnormal signal is transferred to the monitoring-person mobile telephone/processing block 901, and the flow advances to Step S526. In Step S526, a check is made as to whether or not a movement signal has been received from the active-individual ring sensor block 902. When a movement signal has been received, the flow advances to Step S528. The movement signal is sent to the monitoring-person mobile telephone/processing block 901, and the flow advances to Step S516. When a movement signal has not been received in Step S526, the flow advances directly to Step S516. In the same manner as above, the time signal is sent to the monitoring-person mobile telephone/processing block 901 in Step S516, and the flow is ended.

By contrast, when reception of an abnormal signal has not been detected in Step S522, the flow advances to Step S530 where a check is made as to whether or not a low charge signal has been received from the active-individual ring sensor block 902 attached to a finger 14 and currently in use. When a low charge signal has been received, the flow advances to Step S532. The low charge signal is transferred to the monitoring-person mobile telephone/processing block 901, and the flow advances to Step S534. In Step S534, a check is made as to whether or not a charging signal has been received from the active-individual ring sensor block 902 not currently in use. When a charging signal has not been received, the flow advances immediately to Step S516. When a charging signal has been received, the flow advances from Step S534 to Step S536 where a check is made as to whether or not a fully charged signal has been received from the active-individual ring sensor block 902 receiving the charging signal. When a fully charged signal has been received, the flow advances to Step S538. The received signal is transferred to the monitoring-person mobile telephone/processing block 901 as a spare fully charged signal, and the flow advances to Step S516. This means the active-individual ring sensor block 902 currently being used can be immediately replaced by the fully charged spare. The flow advances to Step S540 when reception of the fully charged signal cannot be confirmed in Step S536. Information indicating that the spare active-individual ring sensor block 902 is still being charged is sent to the monitoring-person mobile telephone/processing block 901, and the flow advances to Step S516.

The flow advances to Step S542 when reception of a low charge signal cannot be confirmed in Step S530. Reaching Step S542 as a result of checking for a response to a request signal means that all of the active-individual ring sensor blocks 902 are not attached when neither a good-health signal nor an abnormal signal has been received despite performing a measurement with a charged power supply. Therefore, in Step S542, a check is made as to whether or not a charging signal has been received from any active-individual ring sensor block 902 currently not in use. When a charging signal has not been received, the flow advances to Step S544. As further confirmation, a check is made as to whether or not a non-attachment signal has been received from any of the active-individual ring sensor blocks 902. When reception of a non-attachment signal has been confirmed, the flow advances to Step S546. Information indicating that all of the active-individual ring sensor blocks 902 are not attached is transmitted to the monitoring-person mobile telephone/processing block 901, and the flow advances to Step S516. When in Step S544 it is impossible to confirm reception of a signal indicating that all of the active-individual ring sensor blocks 902 are in a non-attached state, the flow advances to Step S548. Because there is a possibility that the system is malfunctioning, information indicating that system confirmation is required is returned to the monitoring-person mobile telephone/processing block 901, and the flow advances to Step S516.

When reception of a charging signal has been confirmed in Step S542, the flow advances to Step S550 where a check is made as to whether or not a fully charged signal has been received from the active-individual ring sensor block 902 from which a charging signal had been received. When a fully charged signal has been received, the flow advances to Step S552. The received fully charged signal is transferred to the monitoring-person mobile telephone/processing block 901, and the flow advances to Step S516. The flow advances to Step S554 when reception of a fully charged signal cannot be confirmed in Step S550. Information indicating that the active-individual ring sensor block 902 is currently charging is transferred to the monitoring-person mobile telephone/processing block 901, and the flow advances to Step S516.

Figure 27:
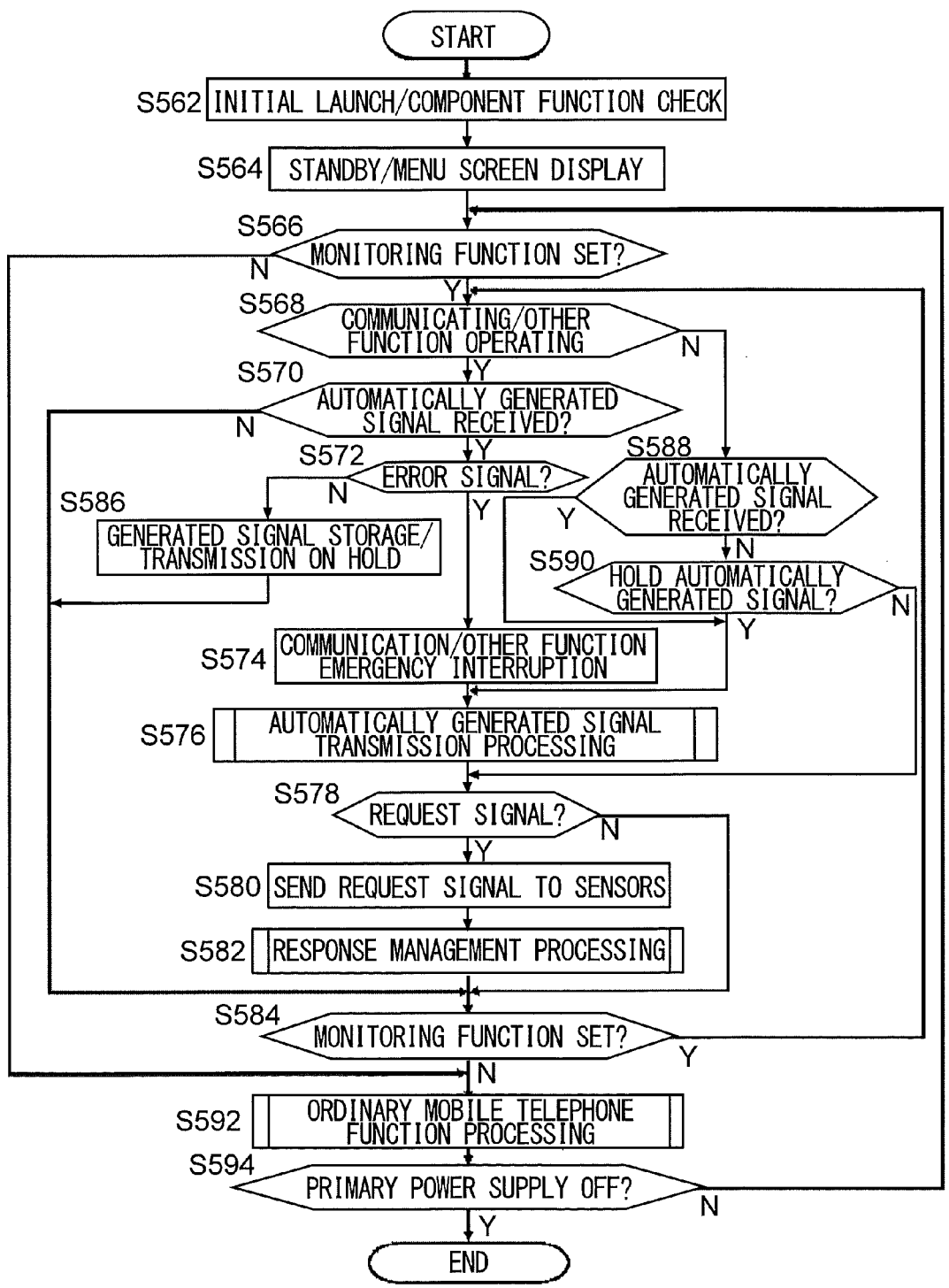
FIG. 27 is a flowchart showing the functions of the processing control unit for the involved-person mobile telephone/processing block in Example 10.

FIG. 27 is a flowchart showing the functions of the processing control unit 42 for the involved-person mobile telephone/processing block 104 in FIG. 20. The flow starts when the primary power supply for the mobile telephone/processing block 104 has been turned on. In Step S562, the telephone is initialized and the functions of the various components are checked. In Step S564, the device goes into standby and a menu screen is displayed on the display unit 50. The menu includes settings for the monitoring function, which can be selected.

Next, the flow advances to Step S566 where a check is made as to whether or not the monitoring function has been set by operating the operating unit 56 in accordance with the menu. When set, the flow advances to Step S568 where a check is made as to whether or not a telephone call is currently being conducted or a function other than the monitoring function is currently being performed by the mobile telephone/processing block 104. When a telephone call or other function is currently being performed, the flow advances to Step S570 where a check is made as to whether or not automatically generated signals have been received. When automatically generated signals have been received, the flow advances to Step S572 where a check is made as to whether or not an abnormal signal is included in the generated signals that have been received. When an abnormal signal is included, the flow advances to Step S574. The telephone call or function other than the monitoring function currently being performed is interrupted, processing of the abnormal signal is given priority, and the flow advances to the automatically generated signal transmission process in Step S576. Because Step S576 corresponds to Step S490 and Step S492 in FIG. 25, the abnormal signal received in Step S570 is transferred immediately to the monitoring service base/processing block 903 and the monitoring-person mobile telephone/processing block 901.

Next, Step S578 to Step S582 are similar to Step S496 to Step S502 in FIG. 25 and are related to handling request signals. Afterwards, in Step S584, a check is made as to whether or not the monitoring function settings are being continued. When automatically generated signals have not been received in Step S570, the flow advances directly to Step S584 where the telephone call or function other than the monitoring function is continued. When automatically generated signals have been received but reception of an abnormal signal has not been confirmed in Step S572, the flow advances to Step S586. The automatically generated signals that have been received are stored, transmission is put on hold, and the flow advances to Step S584. When automatically generated signals from the active-individual ring sensor block 902 are received by the short-range communication unit 44 while the involved-person mobile telephone/processing block 104 is conducting a telephone call or performing a function other than the monitoring function, and an urgent signal such as an abnormal signal is included in the automatically generated signals, the abnormal signal is given priority, and the call or function is interrupted. When the automatically generated signals allow for a relative degree of latitude, the received signals are stored and transmission is put on hold until the telephone call or function other than the monitoring function has been ended.

When it has been confirmed in Step S568 that the mobile telephone/processing block 104 is not being used to conduct a telephone call or perform a function other than the monitoring function, the flow advances to Step S588 where a check is made as to whether or not automatically generated signals have been received. When reception of automatically generated signals has not been confirmed, the flow advances to Step S590 where a check is made as to whether or not any automatically generated signals have been stored for later transmission by the function of Step S586. When automatically generated signals have been stored, the flow advances to the automatically generated signal transmission process in Step S576. The flow advances to the automatically generated signal transmission process in Step S576 when reception of automatically generated signals has been confirmed in Step S588. The flow thereby advances to the transmission process when the mobile telephone/processing block 104 is not being used to conduct a telephone call or perform a function other than the monitoring function, regardless of the automatically generated signals. When automatically generated signals are being held for transmission, the flow advances to the transmission process as soon as the mobile telephone is no longer being used to conduct a telephone call or perform a function other than the monitoring function. By contrast, when it has not been confirmed in Step S590 that there are automatically generated signals being held, it means there are no automatically generated signals that need to be transmitted at this time. The flow therefore proceeds to the process for responding to request signals in Step S578 and subsequent steps.

When Step S584 has been reached by any of the routes and it has been confirmed that the monitoring function settings have been continued, the flow returns to Step S568. Steps S568 to Step S590 are repeated and the various situations related to the monitoring function are addressed until the monitoring function settings have been disabled. The monitoring function can be disabled by operating the operating unit 56; however, when, as a result of the disabling operation, it has been detected in Step S584 that the monitoring function settings have not been continued, the flow advances to Step S592.

In Step S592, ordinary mobile telephone functions are performed. When the ordinary telephone function processing in Step S592 reaches a milestone or ends, and the flow has returned to standby/menu screen display in Step S594, a check is made as to whether or not the primary power supply for the involved-person mobile telephone/processing block 104 has been turned off. When the primary power supply is detected to have been turned off, the flow is ended. When it has not been detected in Step S594 that the primary power supply has been turned off, the flow returns to Step S566. The loop from Step S566 to Step S594 is repeated until the primary power supply has been turned off.

Example 11

Figure 28:
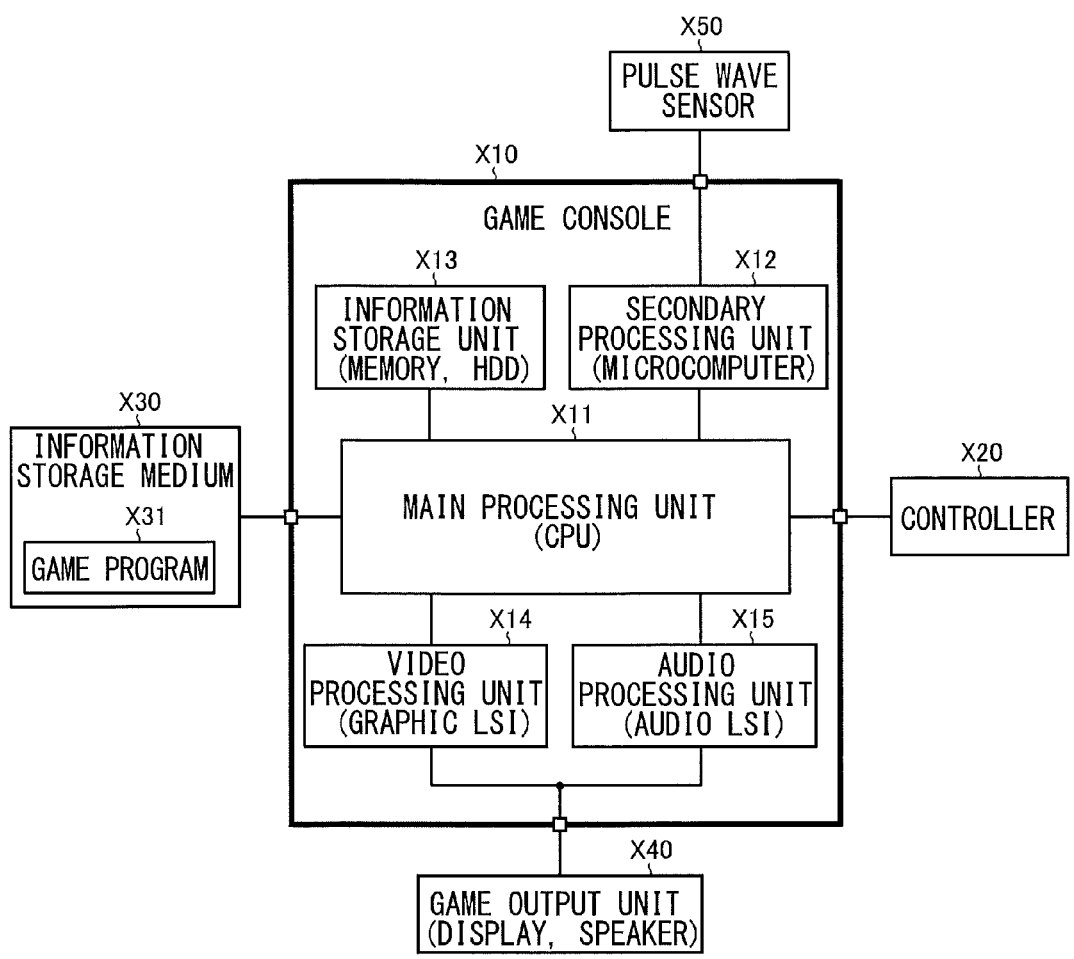
FIG. 28 is a block diagram showing Example 11 of the present invention configured as a game system.

FIG. 28 is a block diagram showing Example 11 of the present invention configured as a game system. The game system in this embodiment has a game console (main unit) X10, a controller X20, an information storage medium X30, a game output unit X40, and a pulse wave sensor X50.

The game console X10 is an electronic device constituting the core of a game system and having a main processing unit X11, a secondary processing unit X12, an information storage unit X13, a video processing unit X14, and an audio processing unit X15. A "game" executed by the game console X10 is commonly referred to as a computer game, and this can be a game of any genre such as an action, fighting, shooting, sports, racing, role-playing, adventure, simulation, puzzles, tables, educational, or music games.

The main processing unit X11 comprehensively controls all of the operations of the game system. The main processing unit X11 can be a central processing unit (CPU).

One of the important functions of the main processing unit X11 related to the seventh technical aspect is that pulse wave information obtained using the pulse wave sensor X50 is used as data in a game. As described in more detail below, the main processing unit X11 includes a function for sending instructions to the video processing unit X14 and the audio processing unit X15 so that at least one of the video data and audio data in the game is generated so as to reflect the pulse wave information.

For example, a game system can be constructed using this configuration in which the physical condition or degree of excitement of the player can be reflected in the game. The reflection of pulse wave information in a game will be explained below in greater detail using specific examples.

Here, "pulse wave information" includes not only a plethysmogram (raw data) obtained by the pulse wave sensor X50, but also a velocity plethysmogram and an acceleration plethysmogram obtained by differentiating this plethysmogram once or twice, and various types of information obtained by analyzing the wave forms (pulse, waveform patterns of acceleration pulse waves, detection state of specific waveform patterns, (number of times detected, detection frequency, continuous detection period), vascular age determined based on the waveform pattern of the acceleration pulse waves, and the like). Among these waveform analyses, the main processing unit X11 primarily executes secondary arithmetic processing with a heavy processing burden (chaos analysis, etc.).

The secondary processing unit X12 performs the primary arithmetic processing with a lighter processing burden on the plethysmogram (raw data) inputted from the pulse wave sensor X50 (first differential, second differential, etc.). The secondary processing unit X12 can be a small-scale microprocessor. Configurations using a secondary processing unit X12 can obtain and analyze pulse wave information without compromising the computing power of the main processing unit X11 (the computing power used to execute the game). When the computing power of the main processing unit X11 is sufficiently high, a secondary processing unit X12 is not required.

The information storage unit X13 is used as storage space for the basic software (OS or operating system), expansion space for the game program, or workspace for the main processing unit X11. A read-only memory (ROM), random-access memory (RAM), flash memory, hard disk drive, or the like can be suitably used as the information storage unit X13.

The video processing unit X14 generates video data based on instructions from the main processing unit X11, and outputs the generated video data to the game output unit X40. The video processing unit X14 can be a video processing large-scale integrated circuit (LSI).

The audio processing unit X15 generates audio data based on instructions from the main processing unit X11, and outputs the generated audio data to the game output unit X40. The audio processing unit X15 can be an audio processing LSI.

The controller X20 is a user interface for receiving input operations from a player. Examples include a ten-key pad, various types of buttons, a three-axis acceleration sensor, and a touch pad. The controller X20 can be an external unit with a wired or wireless connection to the game console X10, or an internal unit built into the game console X10.

The information storage medium X30 is readable by the game system, and stores a game program X31 used to control the game system and execute a game. The information storage medium X30 can be an optical disk (CD-ROM, DVD-ROM, or BD-ROM) or semiconductor memory (a dedicated cartridge, USB memory, or the like). In the game program X31, an important function related to the seventh technical aspect is a program which is read and executed by the primary processing unit X11 so that the primary processing unit X11 is controlled as means for sending instructions to the video processing unit X14 and the audio processing unit X15 to generate at least one of video data and audio data so as to reflect pulse wave information. The game program X31 does not have to be read and obtained from the information storage medium X30. It can also be downloaded from a network, or stored beforehand in the information storage unit X13 of the game console X10.

The game output unit X40 receives video data and audio data from the game console X10, and outputs game video and audio. The game output unit X40 can be a television having both a display and speaker.

The pulse wave sensor X50 measures pulse waves of a living body (a plethysmogram) by detecting with a light-receiving unit the intensity of light that is emitted from a light-emitting unit and passes through a body. The measurement results are outputted to the game console X10 (more specifically, the secondary processing unit X12). The pulse wave sensor X50 can be a ring or pouch placed over a finger of the player, or a clip attached to an earlobe of the player. The pulse wave sensor X50 can have a wired or wireless hookup with the game console X10, or can be built into the game console X10 or the controller X20. When, for example, the pulse wave sensor X50 is an internal unit built into the controller X20, the pulse wave sensor X50 is desirably provided in a position where a finger of the player inevitably makes direct contact with, or comes close to, the sensor when the player holds the controller X20 in their hand. In this configuration, pulse waves can be measured from a player and the measurements results can be reflected in a game without the player being aware of the means by which this occurs.

The game console depicted in FIG. 28 is a stationary unit for home use. However, application of the seventh technical aspect is not limited to this. For example, the technical aspect can be applied to a portable game console (including a mobile telephone with a built-in game function), or an arcade-type game console for commercial use. When the seventh technical aspect is applied to a portable game console, at least the controller X20 and the game output unit X40 are built into the main unit of the game console X10.

<Principles of Pulse Wave Measurement>

Figure 29:
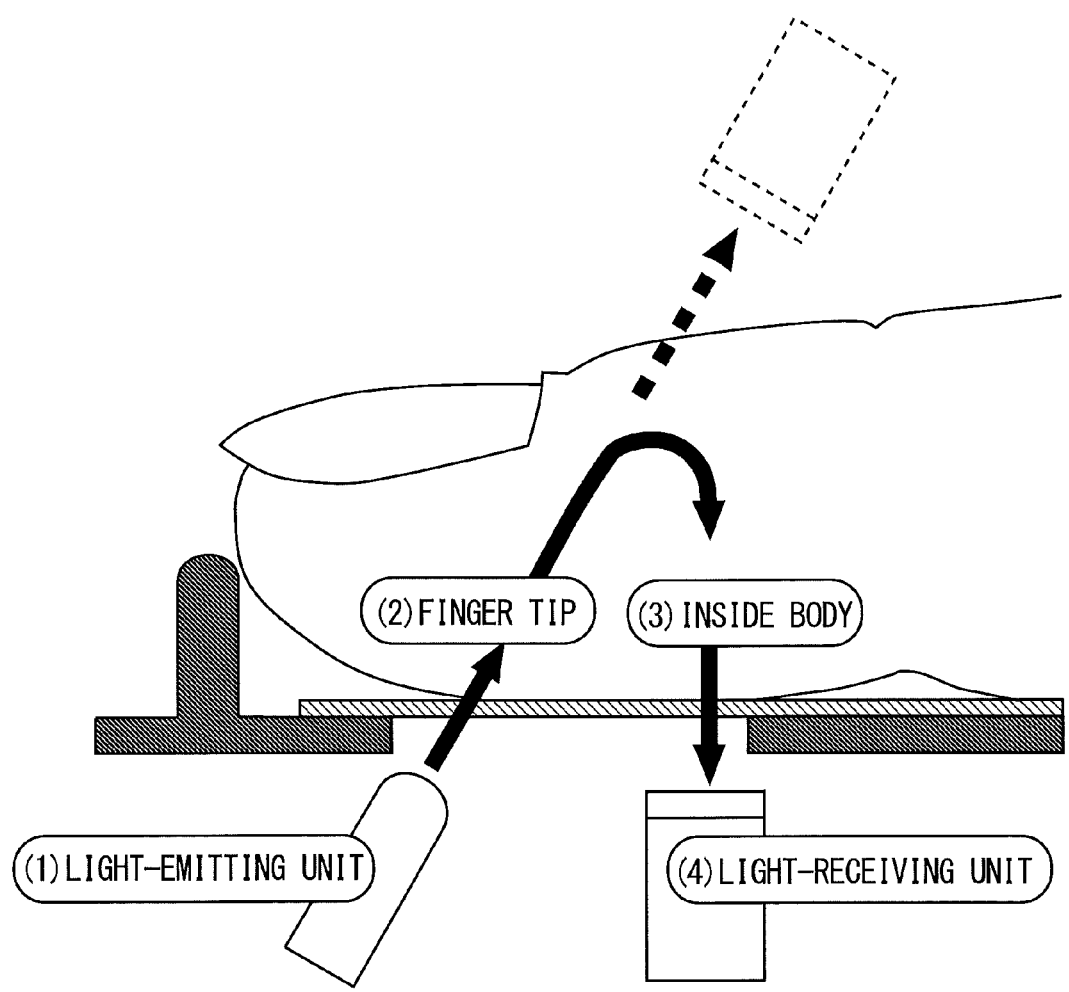
FIG. 29 is a schematic diagram used to describe the principles of pulse wave measurements.
Figure 30:
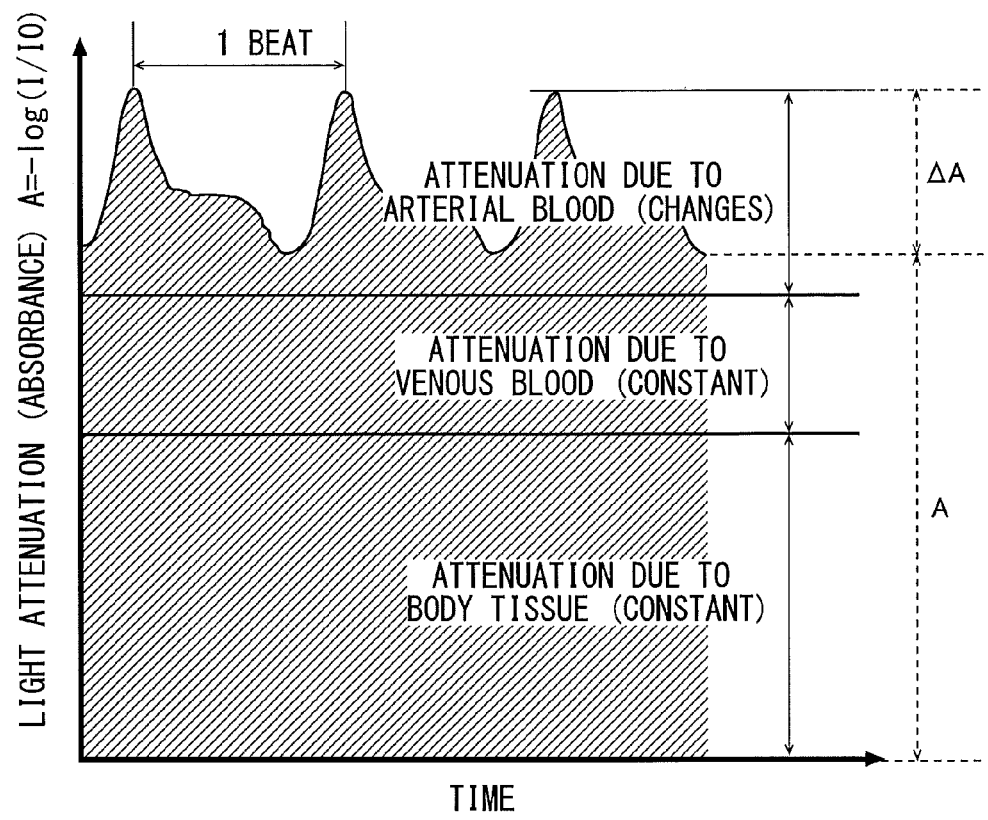
FIG. 30 is a waveform diagram showing the change over time in the attenuation of light (absorbance) in a living body.

FIG. 29 is a schematic diagram used to explain the principles of pulse wave measurements, and FIG. 30 is a waveform diagram showing the change over time in the attenuation of light (absorbance) in a body.

In pulse wave measurements using the plethysmographic method, for example, as shown in FIG. 29, a fingertip is pressed against a measurement window (a different site can be used as long as the blood vessel is moving), light from a light-emitting unit (an LED or the like) is emitted towards the window, and the intensity of the light passing through the body and escaping outside is detected by a light-receiving unit (a photodiode, a phototransistor, or the like). Here, as shown in FIG. 30, the attenuation of light (absorbance) by tissue and venous blood (deoxygenated hemoglobin Hb) is constant, but the attenuation of light (absorbance) by arterial blood (oxygenated hemoglobin HbO2) changes over time due to the pulse. Therefore, by measuring the change in absorbance in a peripheral artery using a "window into the body" in the visible spectrum or the near infrared spectrum (wavelength range in which light readily passes through the body such as the near infrared range (700-1200 nm)), a plethysmogram can be measured.

<Analysis Based on Pulse Waves>

Pulse waves under the sway of the heart and autonomic nerves do not always behave in a constant manner. Instead, changes (fluctuations) occur based on the condition of the measured person. Fluctuations occur based on the autonomic (sympathetic, parasympathetic) balance. Because autonomic promotion and suppression reflect the psychological state of a person, information on the psychological state of a measured person can be obtained from pulse wave fluctuations. Therefore, by analyzing changes (fluctuations) in pulse waves, various types of physical and psychological information can be obtained from the measured person. For example, the heart rate can indicate the level of physical activity or tension in the measured person. Changes in heart rate can indicate levels of fatigue, sleepiness, and stress in the measured person. By performing a differential analysis twice on a plethysmogram along a time axis, acceleration pulse waves can be obtained which can indicate the age of the blood vessels and the degree of arteriosclerosis in the measured person.

<Acceleration Plethysmogram>

Figure 31:
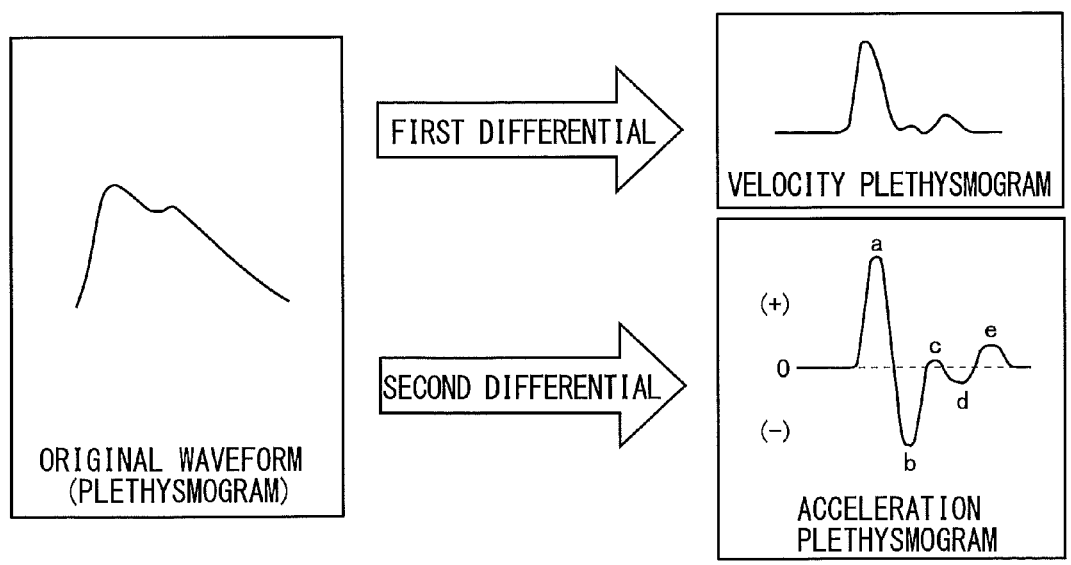
FIG. 31 is a diagram showing the differences in the original waveform (plethysmogram), velocity plethysmogram, and acceleration plethysmogram.

FIG. 31 is a diagram showing the differences in the original waveform (plethysmogram), velocity plethysmogram, and acceleration plethysmogram. The original waveform (plethysmogram) is differentiated once, and the resulting primary differential wave represents a velocity plethysmogram. When differentiated twice, the resulting secondary differential wave represents an acceleration plethysmogram. However, these are not directly related to the speed of blood flow or acceleration.

The peaks for the various extreme values in the acceleration plethysmogram have been named the initial systolic positive wave (wave a), the initial systolic negative wave (wave b), the mid-systolic rising wave (wave c), the late systolic negative wave (wave d), and the initial diastolic positive wave (e). These values are based on the height of each waveform peak from a baseline.

<Waveform Pattern of Acceleration Plethysmogram>

Figure 32:
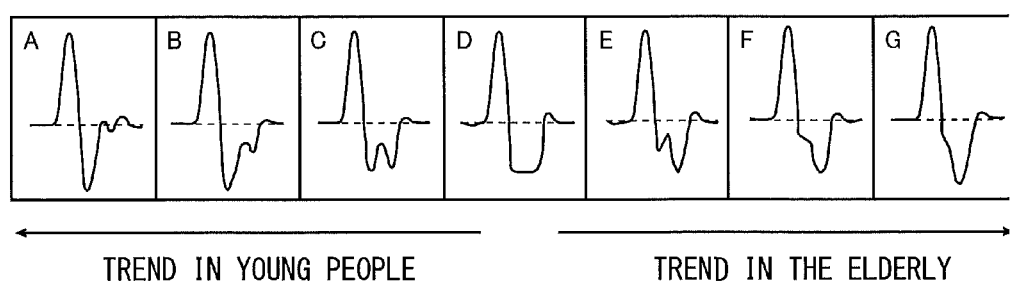
FIG. 32 is a diagram showing the waveform patterns for an acceleration plethysmogram based on vascular age.

FIG. 32 is a diagram showing the waveform patterns (Type A-Type G) for an acceleration plethysmogram based on vascular age. In Type A, wave b is sufficiently deep and wave d is shallow relative to wave a. In Type G, wave b is shallow and wave d is deep relative to wave a. As a person ages, wave b becomes shallower and wave d becomes deeper. Most people in their twenties are Type A or Type B. In their thirties, fewer people are Type A and more people are Type B or Type C. In their forties and fifties, more people are Type C and Type D. In their seventies, the majority of people are Type E through Type G. Thus, the age of blood vessels can be determined by analyzing the waveform pattern in an acceleration plethysmogram.

<First Application of Pulse Wave Information in Example 11>

Figure 33:
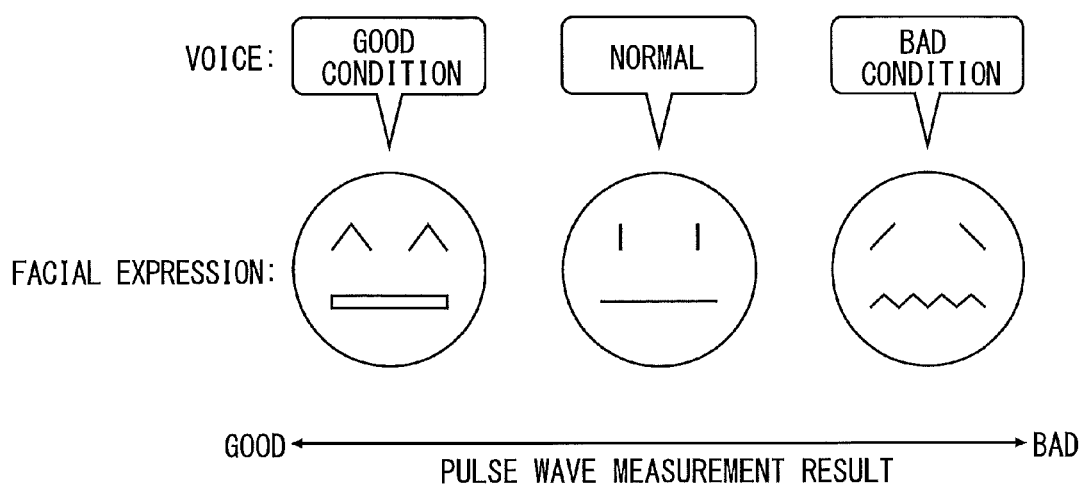
FIG. 33 is a diagram used to describe the first application for pulse wave information in Example 11.

FIG. 33 is a diagram used to explain the first application for pulse wave information in Example 11 (a configuration in which pulse wave information is reflected in the facial expressions and voice of a game character). In the game system of the first application, the main processing unit X11 sends instructions to the video processing unit X14 and the audio processing unit X15 to generate at least one of facial expressions and a voice so as to reflect pulse wave information.

For example, when the results of a pulse wave measurement are good (tension is low or the vascular age is lower than the person's actual age), the main processing unit X11 sends instructions to the video processing unit X14 and the audio processing unit X15 to generate a smiling face on a game character or a robust voice for the game character. Conversely, when the results of a pulse wave measurement are poor (tension is high or the vascular age is higher than the person's actual age), the main processing unit X11 sends instructions to the video processing unit X14 and the audio processing unit X15 to generate a downcast facial expression on a game character or a downcast voice for the game character. When the results of a pulse wave measurement are neither good nor bad, the degree of excitement of the player is synchronized with the facial expression (degree of excitement) of the game character. Needless to say, the method of reflecting pulse wave information in the game can have many different variations.

Parameters used to change the facial expression of the game character include the contours of the face, the shape of the parts constituting the face (eyes, eyebrows, nose, mouth, ears, hair, etc.), and complexion.

In the game system of the first application, the facial expression and voice of a game character can be changed based on pulse wave information obtained using the pulse wave sensor X50. The physical condition and degree of excitement of the player can thereby be reflected in the game.

<Second Application of Pulse Wave Information in Example 11>

Figure 34:
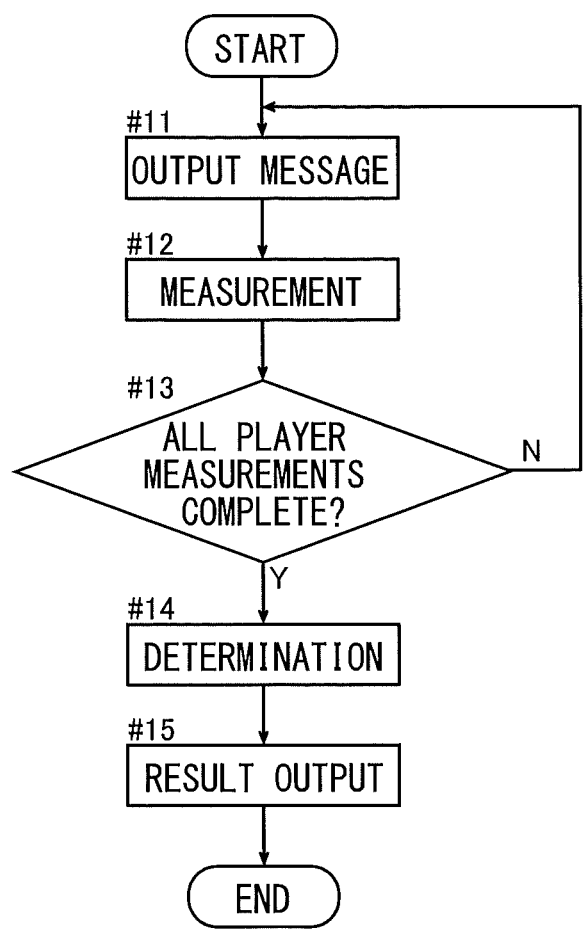
FIG. 34 is a diagram used to describe the second application for pulse wave information in Example 11.

FIG. 34 is a diagram used to explain the second application for pulse wave information in Example 11 (determining the winner among a plurality of players based on vascular age). In the game system of the second application, the main processing unit X11 calculates the vascular age of a plurality of players based on output from a pulse wave sensor X50, and the vascular ages and relative results are used as data in a game.

In Step #11, a message is outputted for each player to attach a pulse wave sensor X50. In Step #12, pulse wave measurements and vascular age determinations are performed on the players using a pulse wave sensor X50. The determination results are stored temporarily in the information storage unit X13. In Step #13, a check is made as to whether or not the pulse wave measurements and vascular age determinations have been performed for all players. When the answer in Step #13 is NO, the flow returns to Step #11 and the pulse wave measurements and vascular age determinations are repeated. When the answer in Step #13 is YES, the vascular age of the players is compared in Step #14 and the winner of the game is determined based on the results. An example of a possible method used to determine the winner of the game is that the player who has the youngest vascular age relative to actual age is determined to be the winner. In Step #15, the results from the determination of the winner are outputted to the game output unit X40, and the flow is ended.

In the game system of the second application, the winner among a plurality of players can be determined based on vascular age. A combat game can thereby be provided which anyone can feel free to enjoy because the result is unrelated to actual skill in the game.

FIG. 34 is a flowchart premised on the idea that a plurality of players will attach the same pulse wave sensor X50 one after another to perform a pulse wave measurement. However, the configuration of the present invention is not limited to this. A plurality of players can simultaneously or almost simultaneously use a plurality of pulse wave sensors X50 to perform pulse wave measurements. This configuration can reduce the amount of time required to play the game.

In this description, the vascular age of a plurality of players calculated based on output from a pulse wave sensor X50 was used to determine the winner of a game. However, the way vascular age is reflected in a game is not limited to this. The main processing unit X11 can calculate the vascular age of a single player based on the output from a pulse wave sensor X50 and use the vascular age as data in a game. For example, in a version of the first application described above, the appearance of the game character (child, teen, middle-aged person, elderly person, etc.) can be changed based on the vascular age of the player.

<Third Application of Pulse Wave Information in Example 11>

Figure 35:
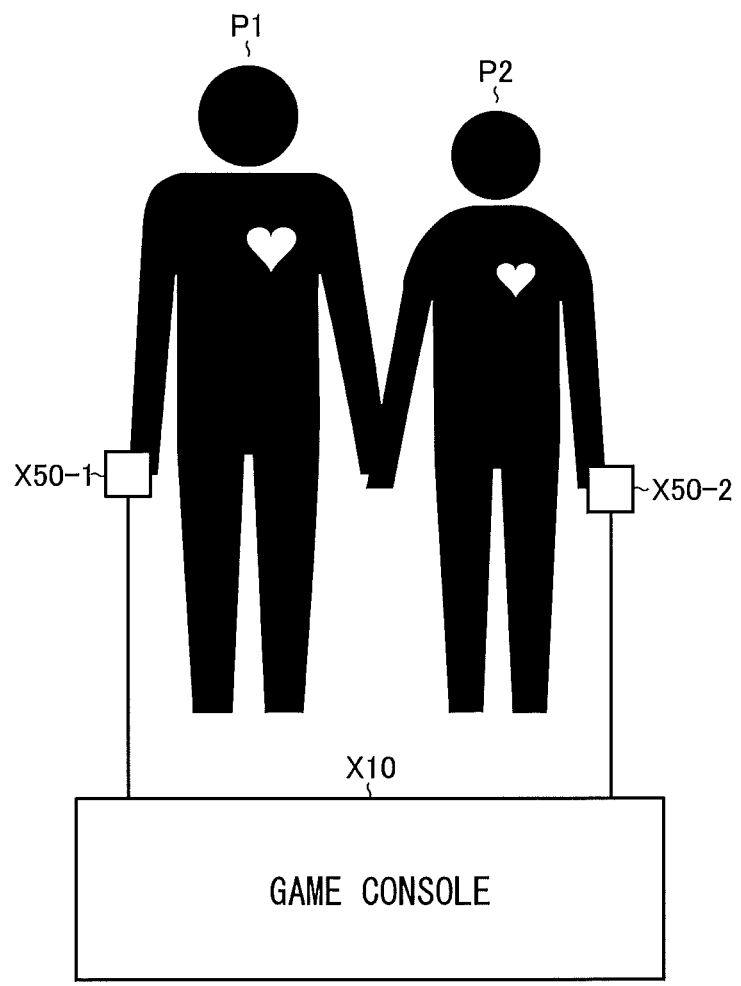
FIG. 35 is a diagram used to describe the third application for pulse wave information in Example 11.

FIG. 35 is a diagram used to explain the third application for pulse wave information in Example 11 (determining compatibility based on pulse wave information determined at the same time). In the game system of the third application, the main processing unit X11 simultaneously (or almost simultaneously) obtains pulse wave information from players P1 and P2 based on output from pulse wave sensors X50-1 and X50-2, and uses the pulse wave information as data in a game.

For example, a pulse wave measurement can be performed while player P1 and player P2 are holding hands to determine the compatibility of both players based on the individual pulse wave information. When, for example, player P1 and player P2 hold hands in this method of determining compatibility, and the pulse of one of the players rises, compatibility is 50% (unrequited love). When the pulses of both players rise simultaneously, the compatibility is 100% (mutual love). When there is no change in the pulse of either player, compatibility is 0%.

The game system in the third application can provide an unprecedented experience-based game.

In this description, compatibility was determined using pulse wave information from a plurality of players measured simultaneously. However, the reflection of pulse wave information from a plurality of players in a game is not limited to this. For example, a game can be constructed so that foes exchange threatening words to startle and provoke each other, and the one who raises the pulse of his foe the most is the winner.

<Fourth Application of Pulse Wave Information in Example 11>

Figure 36:
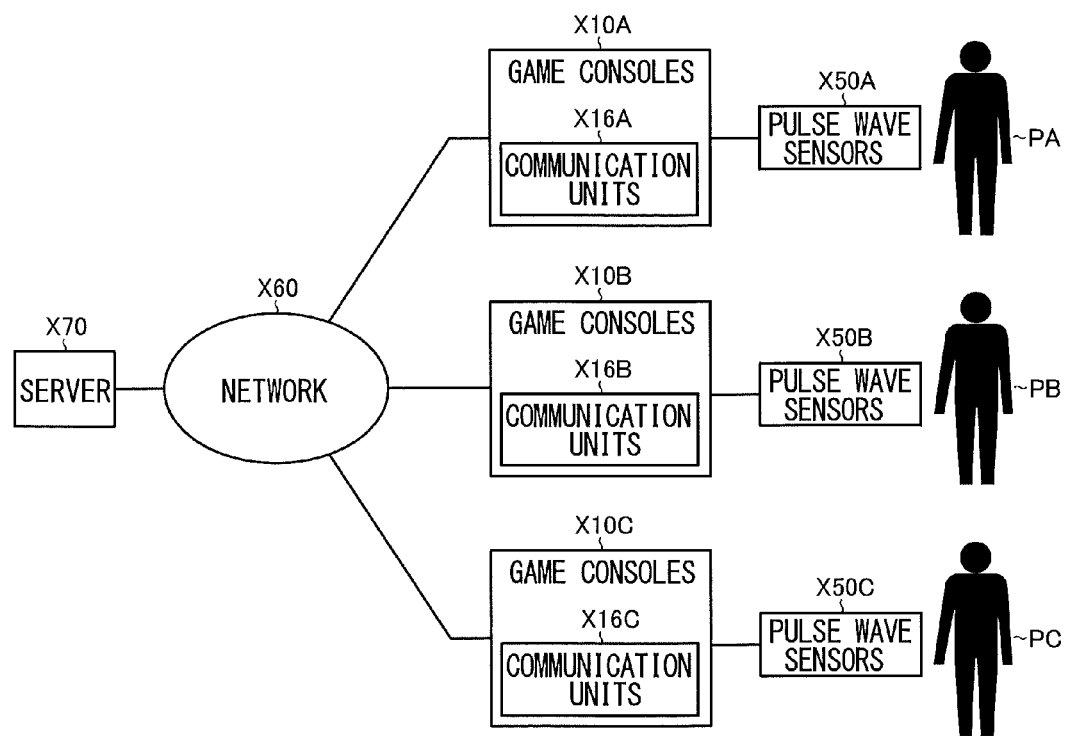
FIG. 36 is a diagram used to describe the fourth application for pulse wave information in Example 11.

FIG. 36 is a diagram used to explain the fourth application for pulse wave information in Example 11 (network for sharing pulse wave information). The game system in the fourth application has communication units (the communication units X16A to X16C built into game consoles X10A to X10C) for sending and receiving pulse wave information via a network X60 to and from another game system (game consoles X10A to X10C) or a server X70.

In a game system of the fourth application such as an online game, the pulse of the players PA-PC is used as an indicator to reflect the degree of excitement of friends and foes in a game. This can increase the sense of realism in a combat game and the sense of bonding among friends.

In the configuration explained in FIG. 36, the pulse wave information is shared via network communication (communication via network X60). However, the communication method is not limited to this. For example, ad-hoc communication can be conducted between game consoles X10A-X10C.

<Fifth Application of Pulse Wave Information in Example 11>

FIG. 37 is a diagram used to explain the fifth application for pulse wave information in Example 11 (ranking a plurality of players based on pulse wave information). The game system of the fifth application is a modified version of the fourth application explained above. Here, the main processing unit X11 sends instructions to the video processing unit X14 and the audio processing unit X15 to rank a plurality of players based on a plurality of pulse wave information obtained via communication units (see X16A-X16C in FIG. 36), and output the results of the ranking.

In the game system of the fifth application, a plurality of players can enjoy the rankings which compare one player to other players.

<Sixth Application of Pulse Wave Information in Example 11>

Figure 38:
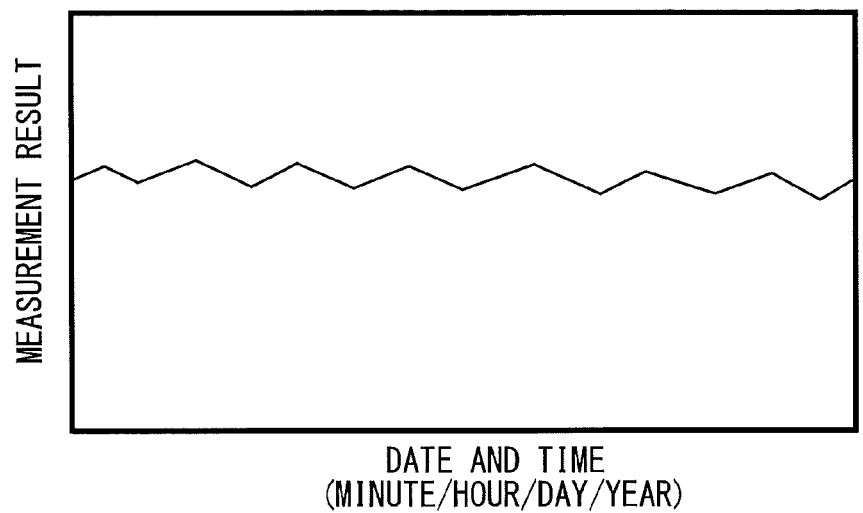
FIG. 38 is a diagram used to describe the sixth application for pulse wave information in Example 11.

FIG. 38 is a diagram used to explain the sixth application for pulse wave information in Example 11 (outputting a change in pulse wave information over time). In the game system of the sixth application, the pulse wave information is stamped the date and time, and stored in the information storage unit X13. Here, "date and time" includes minute, hour, day, month, and year units which can be changed at will by the actions of the player.

In the game system of the sixth application, the player can easily ascertain changes in pulse wave information over time (changes in physical condition, degree of excitement, rejuvenation of vascular age, and the like). When combined with a fitness game, changes in pulse during activities remain in the history. This can be used to provide valuable advice to players related to daily healthcare and improved physical performance.

<Seventh Application of Pulse Wave Information in Example 11>

FIG. 39 is a diagram used to explain the seventh application for pulse wave information in Example 11 (reflecting pulse wave information in the generation of game characters, changes in character attributes, and transformations in characters). In the game system of the seventh application, the main processing unit X11 sends instructions to the video processing unit X14 and the audio processing unit X15 so that pulse wave information is reflected in at least the generation of game characters, changes in character attributes, and transformations in characters.

For example, when the pulse is higher than a predetermined value, it is judged that the player is excited. Character X (e.g., a powerful boss character), which appears only when the player is excited, is generated in a case in which it is judged that the player is in an excited state. Character Y is given a first attribute (e.g., an aggressive character), and the external appearance of Character Z is given a first transformation (e.g., a transformation in which his or her hair bristles).

When the pulse is lower than a predetermined reference value, it is judged that the player is calm. In this situation, Character X described above does not appear. Character Y is given a second attribute (e.g., a defensive character), and the external appearance of Character Z is given a second transformation (e.g., a transformation in which his or her hair returns to normal).

In the game system of the seventh application, pulse wave information obtained using a pulse wave sensor X50 is used to generate game characters, to change character attributes, and to transform the characters. As a result, the physical condition and degree of excitement of a player can be reflected in a game.

<Eighth Application of Pulse Wave Information in Example 11>

Figure 40:
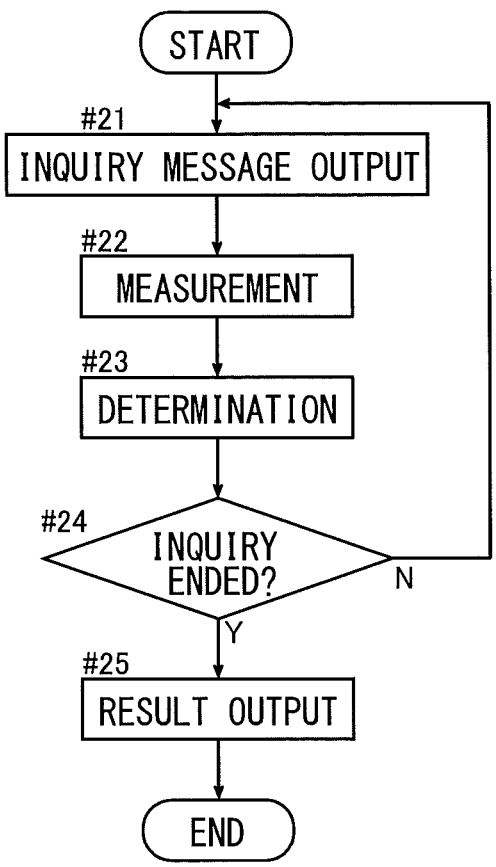
FIG. 40 is a diagram used to describe the eighth application for pulse wave information in Example 11.

FIG. 40 is a diagram used to explain the eighth application for pulse wave information in Example 11 (simple lie detector). In the game system of the eighth application, the main processing unit X11 determines whether or not the player's answer to a question is true based on pulse wave information obtained when the player answered the question. The results of this determination are then used as data in a game.

In Step #21, a predetermined question message is outputted to a player wearing the pulse wave sensor X50. The player gives a YES or NO response to the question message (e.g., "Have you ever done XXX?"). In Step #22, a pulse wave measurement is performed when the player wearing the pulse wave sensor X50 answers the question. In Step #23, a check is made as to whether or not the player's answer is true based on pulse wave information obtained in Step #22. For example, when the pulse does not change during questioning, it is determined that the player's answer is true. When the pulse changes dramatically (rises), it is determined that the player's answer is false. The results of this determination are stored temporarily in the information storage unit X13. In Step #24, a check is made as to whether or not all of the questions have been answered. When the determination is NO in Step #24, the flow returns to Step #21, and the output of question messages is repeated. When the determination is YES in Step #24, the determination results for each question in Step #25 are outputted to the game output unit X40 and the series flow is ended.

The game system in the eighth application can provide an unprecedented experience-based game.

<Ninth Application of Pulse Wave Information in Example 11>

Figure 41:
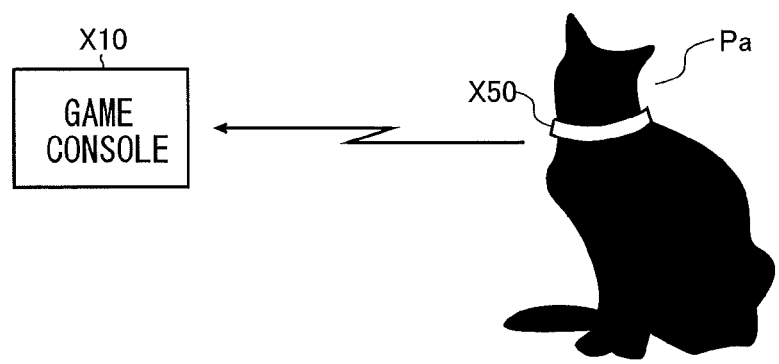
FIG. 41 is a diagram used to describe the ninth application for pulse wave information in Example 11.

FIG. 41 is a diagram used to explain the ninth application for pulse wave information in Example 11 (pet communication tool). In the game system of the ninth application, the pulse wave sensor X50 is attached not to a player but to a pet Pa. In particular, the pulse wave sensor X50 is preferably configured as a collar hooked up wirelessly with a game console X10 so as not to deprive the pet Pa of freedom of movement.

In the game system of the ninth application, the degree of relaxation or degree of excitement of the pet Pa can be reflected in the game based on pulse wave information obtained using the pulse wave sensor X50.

<Tenth Application of Pulse Wave Information in Example 11>

Figure 42:
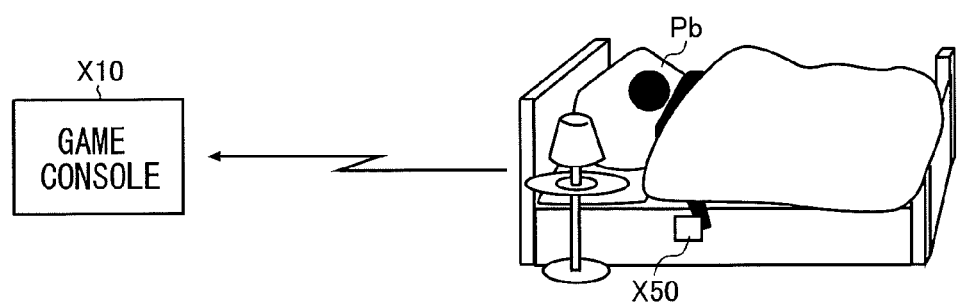
FIG. 42 is a diagram used to describe the tenth application for pulse wave information in Example 11.

FIG. 42 is a diagram used to explain the tenth application for pulse wave information in Example 11 (sleepiness monitor). In the game system of the tenth application, the pulse wave sensor X50 is attached to a sleeping player Pb rather than an active player. In particular, the pulse wave sensor X50 is preferably configured as a ring or bracelet hooked up wirelessly with the game console X10 so that the player Pb is not disturbed in his or her sleep and the pulse wave sensor X50 is prevented from falling off.

In the game system of the tenth application, the quality of sleep of the player (Pb) (restfulness) can be reflected in a game on the basis of pulse wave information during sleep.

<Modifications>

Various modifications can be made to the configuration of the seventh technical aspect other than the embodiments described above without departing from the spirit of the present invention. For example, when the smell sensor and taste sensor in Japanese Laid-open Patent Publication No. 2003-024622 are replaced by a pulse wave sensor, pulse wave information obtained using the pulse wave sensor can be used to increase or decrease player points; to set or change the difficulty of the game; to determine the behavioral patterns, feelings, and emotions of the game character; to develop the situation facing the character in the game in a favorable or unfavorable direction; to change the background scene or background music; and to determine the direction in which the story develops.

The seventh technical aspect can be used to provide a new type of game system with a greater sense of fun and excitement.

<Other Modifications>

The present invention has been explained with respect to the preferred embodiments, but the disclosed invention can be modified using many different methods. It should be obvious to those skilled in the art that the present invention can be embodied using different configurations than those described above. Therefore, the claims below are intended to include modifications in the technical scope of the present invention which do not depart from the spirit or technical field of the present invention.

<Summary of First through Sixth Technical Aspects Shown in Examples 1 through 10>

The following is a summary of the first through sixth technical aspects shown in Examples 1 through 10, which are among the various technical aspects disclosed in the present Specification.

<First Technical Aspect>

The first technical aspect disclosed herein relates to a biometric measurement device.

Useful biometric information for providing healthcare includes pulse waves, oxygen saturation, pulse rate, and body temperature, and several different types of biometric measurement devices have been proposed for this information. As for practical uses for this biometric information, the pulse rate can be measured during activity, and the pulse rate can be fed back to the person performing the activity to determine physical stamina.

Moreover, a biometric information measuring system has been proposed which includes a measurement device terminal, a mobile telephone, and a processing center (e.g., International Laid-open Patent Publication No. WO2002/062222). In this proposal, the measurement device terminal has a measurement unit for measuring biometric information, an adapter for obtaining a telephone number from a mobile telephone to identify a mobile telephone, and transceiving means for linking and outputting biometric information and telephone numbers. The mobile telephone also stores a telephone number to identify the user themselves. The processing center has storing means for storing a database linking the names and the like of users using mobile telephones to telephone numbers, and storing biometric information from the measurement device terminal for each user; and processing means for identifying the user of a mobile telephone based on the telephone number and the database.

However, many unexamined problems remain related to the practical use of measured biometric information.

In view of this situation, an object of the first technical aspect is to provide a practical biometric information measurement device.

In order to achieve this object, the first technical aspect provides a biometric measurement device having: a light-emitting unit for emitting measurement light into a body; a light-receiving unit for receiving the pulse measuring light emitted from the light-emitting unit and absorbed by arterial blood in the body; a storage unit for storing pulse wave information based on the light reception output of the light-receiving unit; a short-range wireless communication unit for transmitting the pulse wave information stored in the storage unit to a processing unit on the outside; and a power supply unit for supplying electric power to these various configurations.

In this configuration, the pulse wave information measurement output, which is based on the light reception output that is caused to pulsate by the absorption of arterial blood, can be put to practical use by an appropriate link with an external processing device via short-range wireless communication. In one example, the biometric measurement device is configured as a ring, and a finger is the measurement target. In another example, the device is configured in an earphone or in headphones used as an output device for music, and an ear is the measurement target. A preferred example of an external processing device is a mobile telephone. A biometric measurement device equipped with the first technical aspect makes use of a short-range communication function provided to the mobile telephone, functions as an accessory of the mobile telephone, and can use biometric information measurements as an application of the mobile telephone. In another preferred example, a biometric measurement device equipped with the first technical aspect can be favorably linked with a processing unit installed in, for example, a fitness center.

According to a specific aspect, the light-receiving unit is installed on the same side of the measurement target as the light-emitting unit so that pulsated measurement light emitted from the light-emitting unit, absorbed by arterial blood in the body, and reflected towards the outside of the body by body tissue is received. The relative position of the light-emitting unit and the light-receiving unit can thereby be made more precise, simple, and compact.

In another specific aspect, a short-range wireless communication unit receives instruction information from an external processing unit related to biometric measurements. Biometric measurements can thereby be performed centrally from the external processing unit. In a more specific aspect, the short-range wireless communication unit receives instruction information from the external processing unit related to the transmission of pulse wave information. Pulse wave signal communication management can thereby be performed centrally from the external processing unit, and interference from other functions in the external processing device can be prevented. In another specific aspect, the pulse wave information is retained by the storage unit when pulse wave information cannot be received by the external processing unit. Linking with the external processing device can thereby be flexibly performed.

In another specific aspect, the short-range wireless communication unit transmits information identifying the biometric measurement device to the external processing unit. A more flexible combination of biometric measurement devices and external processing units can thereby be realized. In another specific aspect, the short-range wireless communication unit transmits information identifying the target person for the biometric measurement to the external processing unit. Pulse wave information from a plurality of persons can thereby be processed and managed. By combining the identification of the biometric measurement device with the identification of the target person for the biometric measurement, pulse wave information from the same person can be continuously managed irrespective of which biometric measurement device is used when a plurality of biometric measurement devices is used.

In another specific aspect, the short-range wireless communication unit transmits information related to the time of a biometric measurement to an external processing unit. A pulse wave information history can thereby be managed at an external processing unit, and long-term changes in pulse wave information from the same person can be diagnosed. Favorable linking between biometric measurement devices and external processing units can thereby be established via short-range wireless communication.

In another specific aspect, the biometric measurement device is given a waterproof structure. Because a biometric measurement device with a waterproof structure can link with an external processing unit via short-range wireless communication, applications for the biometric measurement device can be expanded. For example, systems can be realized in which biometric information measurements are performed while swimming, and devices can be cleaned while still attached. In a more specific aspect, the power supply unit in the biometric measurement device has a storage cell, and a contactless electromagnetic induction unit is provided to charge this storage cell. A preferred configuration is thereby provided for water-resistant applications.

In another specific aspect, an acceleration sensor is provided in the biometric measurement device, and a short-range wireless communication unit transmits acceleration information related to a biometric measurement to an external processing unit. Information indicating whether or not the measurement was conducted in a resting state or active state can thereby be added to the measurement information, and a more accurate judgment can be made. In a more specific aspect, the acceleration information from the acceleration sensor can be used inside the biometric information measurement device to correct any measurement errors that may occur due to activity.

In another specific aspect, independent functioning is possible even when the external processing unit is not functioning. Here, the storage unit retains the measurement results. When the external processing unit is functioning, the measurements can be transmitted. Measurements can thereby be performed without being adversely affected by the status of the external processing unit.

In another specific aspect, a solar cell is provided in the biometric information measurement device. When the output from the solar cell is equal to or higher than a predetermined value, and the power supply from the power supply unit is insufficient, the power supply is automatically turned off and kept off. This increases the number of measurement opportunities.

In another specific aspect, whether or not the device is attached to the measurement target is detected based on the output from the light-receiving unit. It can thereby be confirmed whether or not the biometric information measurement device has been reliably attached to the body without having to add a special means. More specifically, output can be obtained from the light-receiving unit during the measurement in a low power consumption state so that electric power is not wasted in detecting whether or not the device has been attached.

As mentioned above, the first technical aspect allows for practical biometric information measurements to be performed using a biometric measurement device for performing short-range communication with an external processing unit.

The first technical aspect can be applied to a biometric information measurement device for pulse waves, oxygen saturation, pulse rate, and the like.

<Second Technical Aspect>

The second technical aspect disclosed herein relates to a mobile device.

Various additional functions have been proposed for mobile devices such as mobile telephones and portable music players. There have also been proposed a variety of devices for measuring biometric information that is useful for managing the health of a living being or for other purposes. Useful biometric information for providing healthcare includes pulse waves, oxygen saturation, pulse rate, and body temperature. As for practical uses for this biometric information, the pulse rate can be measured during activity, and the pulse rate can be fed back to the person performing the activity to determine physical stamina.

Moreover, a biometric information measuring system has been proposed which includes a measurement device terminal, a mobile telephone, and a processing center (e.g., International Laid-open Patent Publication No. WO2002/062222). In this proposal, the measurement device terminal has a measurement unit for measuring biometric information, an adapter for obtaining a telephone number from a mobile telephone to identify a mobile telephone, and transceiving means for linking and outputting biometric information and telephone numbers. The mobile telephone also stores a telephone number to identify the user themselves. The processing center has storing means for storing a database linking the names and the like of users using mobile telephones to telephone numbers, and storing biometric information from a measurement device terminal for each user; and processing means for identifying the user of a mobile telephone based on the telephone number and the database.

However, many unexamined problems remain related to the practical use of measured biometric information.

In view of this situation, an object of the second technical aspect is to increase the practical effects of biometric information measurements.

In order to achieve this object, the second technical aspect provides a mobile device having: an input unit for inputting pulse wave information from a sensor block having a light-emitting unit for emitting measurement light into a body, and a light-receiving unit for receiving the pulse measuring light emitted from the light-emitting unit and absorbed by arterial blood in the body; an output unit for outputting instruction signals to the sensor block; and a display unit for displaying the status of the sensor block. This allows biometric information to be measured as a function of a mobile device.

According to a specific aspect, the output unit indicates a pulse wave measurement performed using the light-emitting unit and the light-receiving unit in the sensor block. According to another specific aspect, the output unit indicates the output of the pulse wave information measured by the sensor block. The entire system, including the mobile device and the sensor block, can thereby be controlled centrally from the mobile device.

According to another specific aspect, the output unit outputs to the sensor block information on whether or not pulse wave information can be inputted. This can be outputted to the sensor block when pulse wave information can be inputted by the mobile device. The functions of the entire system, including the mobile device and the sensor block, can thereby be harmonized. Particularly when this is set to input pulse wave information from the sensor block in real time, the functions of the mobile device do not have to be dominated by the pulse wave measurement function, and other functions of the mobile device can be used at any time. In a more specific aspect, the output unit issues instructions to the sensor block to put the output of pulse wave information on hold when pulse wave information cannot be inputted.

According to another specific aspect, the display unit displays whether or not the sensor block can measure pulse waves. This allows information from the entire system including a mobile device and a sensor block, to be ascertained centrally from the mobile device. In a more specific aspect, the display unit displays the power level of the sensor block. In another more specific aspect, the display unit displays whether or not the sensor block is attached to the measurement subject. The appropriate measurements can thereby be performed.

In another specific aspect, a control unit is provided in a mobile device for analyzing pulse wave signals inputted from an input unit. The functions of the sensor block can thereby be dedicated to sensing functions, and various types of pulse wave signals can be put to good use by the mobile device.

In another specific aspect, a control unit is provided in a mobile device for recording pulse wave signals inputted from an input unit. The functions of the sensor block can thereby be dedicated to sensing functions, a pulse wave signal history over a long period of time can be retained by the mobile device, and an analysis of changes can contribute to the provision of healthcare.

In another specific aspect, a control unit is provided in a mobile device for calculating the oxygen saturation from pulse wave signals inputted from an input unit. Software in the mobile device can thereby be combined with the sensor block to perform a variety of functions without having to change the hardware configuration of the mobile device.

A preferred example of a mobile device is a mobile telephone. Another preferred example of a mobile device is a portable music terminal. By linking a mobile device with a sensor block according to the technical aspects described above, biometric information measurements can be performed more effectively.

In another technical aspect, a mobile device system is provided having: a light-emitting unit for emitting measurement light into a body; a light-receiving unit for receiving the pulse measuring light emitted from the light-emitting unit and absorbed by arterial blood in the body; a music player unit; and a control unit for linking pulse wave information based on the output from the light-receiving unit to the playing of music by the music player unit. This increases the usefulness of adding a pulse wave information acquiring function to a portable music terminal. In this configuration, the light-emitting unit and the light-receiving unit form a sensor block that is separate from the music player unit.

In a specific aspect, the control unit automatically plays music in the music player unit when pulse waves are being measured by the light-emitting unit and the light-receiving unit. In another specific aspect, the control unit automatically determines the music to be played by the music player unit linked to pulse wave measurements by the light-emitting unit and the light-receiving unit. The obtaining of pulse wave information can thereby be linked to the playing of music without inconveniencing the user.

In another specific aspect, the control unit analyzes the correlation between the pulse wave information based on output from the light-emitting unit, and the playing of music by the music player unit. Healthcare can thereby be provided which takes into account the effect of music on the mind and body. In a more specific aspect, the control unit controls the playing of music by the music player unit based on the analyzed correlation. Background music can thereby be provided in which pulse wave information measurement results are fed back to the playing of music in order to create a more pleasant sound space or to improve the effects of training.

As mentioned above, the second technical aspect allows for practical biometric information measurements to be performed.

The second technical aspect can be applied to mobile devices such as mobile telephones and portable music terminals.

<Third Technical Aspect>

The third technical aspect disclosed herein relates to a biometric information measuring system.

Examples of useful biometric information for providing healthcare include pulse waves, oxygen saturation, pulse rate, and body temperature. Several different types of biometric measurement devices have been proposed for this information. Proposals have been made regarding practical uses for this biometric information. According to these proposals, the pulse rate is measured during activity, and the pulse rate is fed back to the person performing the activity to determine physical stamina.

Moreover, a biometric information measuring system has been proposed which includes a measurement device terminal, a mobile telephone, and a processing center (e.g., International Laid-open Patent Publication No. WO2002/062222). In this proposal, the measurement device terminal has a measurement unit for measuring biometric information, an adapter for obtaining a telephone number from a mobile telephone to identify a mobile telephone, and a transceiving means for linking and outputting biometric information and telephone numbers. The mobile telephone also stores a telephone number to identify the user themselves. The processing center has storing means for storing a database linking the names and the like of users using mobile telephones to telephone numbers, and storing biometric information from a measurement device terminal for each user; and processing means for identifying the user of a mobile telephone based on the telephone number and the database.

However, many unexamined problems remain related to the acquisition and practical use of measured biometric information.

In view of this situation, an object of the third technical aspect is to obtain biometric information and to provide a practical biometric information measuring system.

In order to achieve this object, the third technical aspect provides a biometric information measuring system having a plurality of biometric measurement blocks and a processing block for receiving the measurement information from them.

The plurality of biometric measurement blocks each has a measurement unit for measuring a body and outputting measurement information, a storage unit for storing the measurement information outputted from the measurement unit and measurement unit identification information for identifying the measurement unit, and a transmitting unit for transmitting the measurement information and measurement unit identification information to an outside unit. The processing block includes a receiving unit for receiving the measurement information and the measurement unit identification information from the plurality of biometric measurement blocks transmitted from communication units, and a processing unit for processing measurement information as information from an identified body based on a link between the measurement unit identification information and information identifying the body irrespective of which measurement information is from which biometric measurement block. A measurement can thereby be performed even when the combinations of a plurality of biometric measurement blocks and a plurality of bodies are not fixed, and the plurality of biometric measurement blocks can be used more flexibly.

According to a specific aspect, the plurality of biometric measurement blocks each has a body identification input unit for identifying bodies, and the blocks are configured so that the storage unit stores body identification information along with the measurement information and the measurement unit identification information, and the transmitting unit transmits the body identification information along with the measurement information and the measurement unit identification information to an outside unit. The processing block uses the receiving unit to receive the body identification information along with the measurement information and the measurement unit identification information, and uses the processing unit to process the measurement information as information of an identified body based on the body identification information received along with the measurement unit identification information irrespective of which measurement information comes from which biometric measurement block.

According to another specific aspect, the processing block has an input unit for inputting link identification information indicating the link between a body wearing a biometric measurement block and measurement unit identification information, and a processing unit for processing the measurement information as information of an identified body based on the measurement unit identification information and the link identification information irrespective of which measurement information comes from which biometric measurement block.

In another specific aspect, the processing block has a transmitting unit for transmitting unique combination information indicating the combination of identified measurement units and identified bodies to identified biometric measurement blocks based on measurement unit identification information. The various biometric measurement blocks can thereby ascertain unique information depending on the individual combination of biometric measurement blocks and a plurality of bodies, and a plurality of biometric measurement blocks can be used more flexibly. According to a more specific aspect, a biometric measurement block performs measurements based on the unique combination information transmitted from a processing block, whereby it is possible to eliminate measurement errors dependent on the individual combination of biometric measurement blocks and a plurality of bodies.

According to another technical aspect, a biometric measurement block has a power supply unit including a storage cell for supplying electric power to each component inside the block, and a processing block has a charging unit for charging the storage cell. The processing block can thereby easily manage the charging process. For example, a constantly charged biometric measurement block can be flexibly provided based on a free combination with a living body. In a more specific aspect, the charging unit has a contactless electromagnetic induction unit. In a more specific aspect, the biometric measurement block has a waterproof structure. Accordingly, a constantly charged biometric measurement block can be flexibly provided based on a free combination with a living body in a state of being constantly kept clean by, e.g., to washing or the like.

According to the third technical aspect, a biometric information measuring system is provided which is related to another feature having a plurality of biometric measurement blocks and a processing block for receiving measurement information from these. In other words, a plurality of biometric measurement blocks each has a measurement unit for measuring a body and outputting measurement information, a storage unit for storing the measurement information outputted from the measurement unit and measurement unit identification information for identifying the measurement unit, and a transmitting unit for transmitting the measurement information and measurement unit identification information to an outside unit. The processing block includes a receiving unit for receiving the measurement information and the measurement unit identification information from the plurality of biometric measurement blocks transmitted via communication units, and an analysis unit for totaling the measurement information by biometric measurement block based on the measurement information and measurement unit identification information from the plurality of biometric measurement blocks transmitted from communication units irrespective of which measurement information is from which body. The status of individual processing blocks can thereby be ascertained, e.g., by comparing the average measurement information among biometric measurement blocks and performing a differential analysis on the overall average.

According to the third technical aspect, a biometric measurement system is provided which is related to another feature which as a plurality of biometric measurement blocks and a processing block for receiving measurement information from them. The plurality of biometric measurement blocks each has a measurement unit for measuring a body and outputting measurement information, a storage unit for storing the measurement information outputted from the measurement unit and measurement unit identification information for identifying the measurement unit, and a transmitting unit for transmitting the measurement information and measurement unit identification information to an outside unit. The processing block includes a receiving unit for receiving the measurement information and the measurement unit identification information from the plurality of biometric measurement blocks transmitted from communication units, a designation unit for designating a single biometric measurement block among the plurality of biometric measurement blocks for reception of information by the receiving unit, and a processing unit for processing the received measurement information. Biometric measurements can thereby be performed more flexibly using a plurality of biometric measurement blocks, and measurement information obtained from the processing block can be ascertained more readily.

According to a specific aspect, the storage unit in a plurality of biometric measurement blocks retains measurement information when it has not been designated by the processing block. Designation of biometric measurement blocks by the processing block can thereby be performed more flexibly.

According to another specific aspect, the transmitting unit and the receiving unit are short-range wireless communication units. According to a more specific aspect, a designation unit designates a biometric measurement block which has newly entered the communication range of the short-range communication units as the one biometric measurement block for reception of information by the receiving unit. Designation priority can thereby be performed based on the opportunity for communication, and biometric measurement blocks can be used more flexibly. According to another more specific aspect, the designation unit designates the one biometric measurement block for reception by the receiving unit among the biometric measurement blocks within communication range of the short-range communication units. Biometric measurement blocks can thereby be designated more flexibly and more rationally.

According to another specific aspect, the designation unit designates the biometric measurement block from which information has been received least frequently as the one biometric measurement block for receiving information obtained by the receiving unit. Unbiased measurement information collection from biometric measurement blocks can thereby be ensured, and biometric measurement blocks can be used more flexibly.

According to a specific aspect, the measurement unit has a light-emitting unit for emitting measurement light into a body, and a light-receiving unit for receiving the pulse measuring light emitted from the light-emitting unit and absorbed by arterial blood in the body. According to another specific aspect, the light-receiving unit is installed on the same side of the measurement target as the light-emitting unit so that pulsated measurement light emitted from the light-emitting unit, absorbed by arterial blood in the body, and reflected towards the outside of the body by body tissue is received. According to another specific aspect, the processing unit calculates oxygen saturation based on measurement information related to pulsated measurement light absorbed by arterial blood in the body and received by the receiving unit. These preferred examples can take advantage of the various features described above.

As mentioned above, the third technical aspect obtains biometric information and provides a practical biometric information measuring system.

The third technical aspect can be used as a biometric information measuring system in a location where many people perform a variety of physical activities such as, e.g., a fitness center or sports gym.

<Fourth Technical Aspect>

The fourth technical aspect disclosed herein relates to a measurement device and, more specifically, to a biometric information measuring system.

A variety of measurement systems have been proposed for used on a variety of measurement subjects. Examples of useful biometric information for providing healthcare includes pulse waves, oxygen saturation, pulse rate, and body temperature; and several different types of biometric measurement devices have been proposed for this information. As for practical uses for this biometric information, proposals have been made in regard to measuring the pulse rate during activity, and feeding back the pulse rate to the person performing the activity to determine physical stamina.

Moreover, a biometric information measuring system has been proposed which includes a measurement device terminal, a mobile telephone, and a processing center (e.g., International Laid-open Patent Publication No. WO2002/062222). In this proposal, the measurement device terminal has a measurement unit for measuring biometric information, an adapter for obtaining a telephone number from a mobile telephone to identify a mobile telephone, and transceiving means for linking and outputting biometric information and telephone numbers. The mobile telephone also stores a telephone number to identify the user themselves. The processing center has storing means for storing a database linking the names and the like of users using mobile telephones to telephone numbers, and storing biometric information from the measurement device terminal for each user; and processing means for identifying the user of a mobile telephone based on the telephone number and the database.

However, many unexamined problems remain related to the acquisition of measured information.

In view of this situation, an object of the fourth technical aspect is to provide an information measurement system able to obtain the preferred information.

In order to achieve this object, the fourth technical aspect is a biometric information measuring system having a plurality of biometric measurement blocks, a plurality of reception blocks for receiving measurement information from one of the plurality of biometric measurement blocks, and a processing block for transmitting measurement information via the plurality of reception blocks. Each of the plurality of biometric measurement blocks has a measurement unit for measuring a body and outputting measurement information, a storage unit for storing measurement-unit-specifying information for specifying the measurement unit, and a transmitting unit for transmitting the measurement information and measurement-unit-specifying information to an outside unit. Each of the plurality of reception blocks has a receiving unit for receiving measurement information and measurement-unit-specifying information from one of the plurality of biometric measurement blocks transmitted from the transmitting unit, and a transfer unit for transferring received information. The processing block includes a processing unit for processing the measurement information and the measurement-unit-specifying information from the plurality of receiving units transferred by the transfer unit. Measurement information from the plurality of biometric measurement blocks can thereby be ascertained and processed irrespective of which biometric measurement block the measurement information comes from.

According to a specific aspect, the plurality of reception blocks each includes a storage unit for storing reception block identification information for identifying the reception block. Measurement information can thereby be linked to the attributes of a reception block. According to a more specific aspect, the reception blocks include a training function unit. For example, at a fitness center, measurement information for members can thereby be linked to the training performed by the members. In another specific aspect, the reception blocks include pool lane ropes. Measurement information can thereby be received from bodies wearing biometric measurement blocks while swimming in a pool.

In another specific aspect, the processing block has an input unit for inputting link identification information indicating the link between a body wearing a biometric measurement block and measurement unit identification information, and a processing unit for processing the measurement information as information of an identified body based on the link identification information. Measurement unit identification information can thereby be used to determine which measurement information belongs to which body.

According to another specific aspect, the storage unit in the biometric measurement block is an IC tag. According to another specific aspect, the biometric measurement block has a storage unit for storing measurement information outputted from the measurement unit. According to another specific aspect, the biometric measurement block is a ring. By combining the various features in an appropriate manner, a preferred and practical biometric measurement block can be provided for a biometric information measuring system having the fourth technical aspect.

According to another specific aspect, the biometric measurement block has a power supply unit for supplying electric power to the measurement unit and the transmitting unit. According to another specific aspect, the biometric measurement block has a contactless charging unit for charging the power supply unit. According to another specific aspect, the biometric measurement block has a waterproof structure. By combining the various features in the appropriate manner, a preferred biometric measurement block which solves power supply problems can be provided for a biometric information measuring system having the fourth technical aspect. By combining a waterproof structure with contactless charging, washed and charged biometric measurement blocks can be distributed, for example, to members joining a fitness center.

According to another specific aspect, the processing block has a designation unit for designating the reception block to receive transfers of measurement information. Information can thereby be obtained from a plurality of biometric measurement blocks without confusion. According to another specific aspect, the designation unit selects and designates a reception block for receiving measurement information from a biometric measurement block. Rational information acquisition can thereby be performed.

According to another specific aspect, the processing block receives transfers of measurement information from the reception block when the reception block receives measurement unit identification information from a biometric measurement block. Measurement information can thereby be obtained from a designated measurement block properly and rationally.

According to another technical aspect, a biometric measurement system is provided having a biometric measurement block, a reception block for receiving measurement information from the biometric measurement block, and a processing block for transferring measurement information via the reception block. The biometric measurement block has a measurement unit for measuring a body and outputting measurement information, a storage unit for storing the measurement information outputted from the measurement unit and measurement unit identification information for identifying the measurement unit, and a transmitting unit for transmitting the measurement information and measurement unit identification information to an outside unit. The reception block includes a receiving unit for receiving measurement information and measurement unit identification information the biometric measurement block transmitted from a transmitting unit, and a transfer unit for transferring received information. The processing block includes a control unit for receiving a transfer of measurement information from the transfer unit of the reception block when the reception block has received measurement unit identification information from a biometric measurement block, and a processing unit for processing the transferred measurement information and measurement unit identification information. Information can thereby be obtained rationally. A preferred example of a storage unit for the biometric measurement block is an IC tag.

According to another technical aspect, there is proposed a biometric information measuring system having a biometric measurement block, and a processing block for receiving and processing measurement information from the biometric measurement block. The measurement block includes a measurement unit for outputting measurement information, a transmitting unit for transmitting the measurement information outputted by the measurement unit to an outside unit, and an IC tag. The processing block has an IC reader for reading information on the IC tag, a receiving unit for receiving measurement information from a measurement block transmitted by a transmitting unit when the IC reader has read information from the IC tag, and a processing unit for processing the received measurement information. The processing block can thereby receive measurement information from a measurement block which is linked to information read from an IC tag. A preferred example of a measurement unit is a biometric measurement unit.

According to another technical aspect, there is proposed a biometric information measuring system which has a biometric measurement block, and a processing block for receiving and processing measurement information from the biometric measurement block. The measurement block includes a first measurement unit for outputting first measurement information, and a transmitting unit for transmitting the first measurement information outputted by the first measurement unit to an outside unit. The processing block includes a second measurement unit for outputting second measurement information, a receiving unit for receiving the first measurement information from the measurement block transmitted by the transmitting unit, and a processing unit for processing the received first measurement information and the second measurement information outputted by the second measurement unit. The processing unit can thereby perform processing using first measurement information and second measurement information. A preferred example of the first measurement unit is a pulse wave measurement unit, and a preferred example of the second measurement unit is a pulse rate measurement unit. In a practical example, the measurement block is preferably a ring, and the processing block is preferably a wristwatch.

According to another technical aspect, a biometric measurement system is provided having a ring-shaped measurement block including a measurement unit for outputting pulse wave information and a short-range wireless transmitting unit for transmitting the pulse wave information outputted by the measurement unit to an outside unit, and a wristwatch-shaped processing block including a short-range wireless receiving unit for receiving the pulse wave information from the ring-shaped measurement block transmitted by the short-range wireless transmitting unit, and a processing unit for processing the received pulse wave information. Because a ring-shaped measurement block wearable on a finger of the person whose pulse waves are to be measured is connected to a wristwatch-shaped processing block via short-range wireless communication units, a wearable biometric measurement system can be provided which combines familiar items such as a ring and wristwatch which cause no discomfort and reduce the fear of falling.

As mentioned above, the fourth technical aspect is able to provide an information measurement system able to obtain the preferred information.

The fourth technical aspect can be used as a biometric information measuring system in a location where many people perform a variety of physical activities such as a fitness center or sports gym.

<Fifth Technical Aspect>

The fifth technical aspect disclosed herein relates to a monitoring sensor.

Various monitoring systems have been studied in recent years for elderly persons living alone, given the advent of an aging society. For example, monitoring these persons by detecting pulse abnormalities has been proposed (e.g., International Laid-open Patent Publication No. WO2003/096892).

In addition, there has been proposed an activity monitoring system provided with transmitting means for transmitting, via email, signals outputted by daily activity information detecting means (e.g., Japanese Laid-open Patent Publication No. 2002-251686).

However, many unexamined problems remain related to the execution of smooth monitoring during daily activities.

In view of this situation, an object of the fifth technical aspect is to provide a practical monitoring system able to perform smooth monitoring.

In order to achieve this object, the fifth technical aspect provides a wearable monitoring sensor having: a biometric information detection unit for detecting biological response information; a storage unit for storing the biological response information detected by the biometric information detection unit; a wireless communication unit for transmitting the biological response information stored in the storage unit to an outside unit; a power supply battery for supplying electric power to the biometric information detection unit and the wireless communication unit; and a trigger unit for triggering information detection by the biometric sensor. By providing a wearable monitoring sensor able to perform monitoring via wireless communication and triggering the monitoring when necessary, problems such as unnecessary consumption of battery power and the inability to perform monitoring at critical times can be avoided. Because the state of the monitored person is monitored directly by a biometric information detection unit, the monitoring can be performed more accurately than by indirectly estimating the state of the monitored person. Also, a separate monitoring sensor does not have to be arranged in the living environment.

According to a specific aspect, the trigger unit is an air pressure detection unit. This is triggered by a change in air pressure when the measured person opens and closes doors to enter another room or by a change in air pressure when the measured person ascends or descends stairs. According to another specific aspect, the trigger unit is a clock unit which is triggered every time a predetermined period of time elapses. This allows monitoring to be performed every time a predetermined period of time elapses.

According to another specific aspect, the trigger unit is triggered by a trigger signal received by a wireless communication unit. A trigger signal can thereby be received and the device triggered when the measured person uses a domestic installation such as a bed, bathtub, toilet, or kitchen. Here, the trigger signal generated by the actions of the monitored person is not an indirect monitoring signal. Instead, the state of the monitored person is directly confirmed by the biometric information detection unit in response to the trigger, and targeted monitoring can be performed. According to another specific aspect, the trigger unit is triggered by an information request signal received by a wireless communication unit. Biometric information from the monitored person can thereby be detected, and the results returned in response to a request from a monitoring person at a remote location.

According to another specific aspect, the wireless communication unit transmits the power level of the power supply battery to an outside unit in response to a request signal. A monitoring person at a remote location can thereby confirm the power level of the power supply battery used for wearable monitoring. According to another specific aspect, the wireless communication unit transmits the attachment status of the monitoring sensor to an outside unit in response to a request signal. A monitoring person at a remote location can thereby confirm whether or not the monitoring sensor indispensible for wearable monitoring is attached properly. According to another specific aspect, the wireless communication unit does not transmit the attachment status of the monitoring sensor to an outside unit in response to a request signal when the monitoring sensor is being charged. It is thereby possible to avoid confusion arising if what is transmitted to the monitoring person as an abnormal state is that the monitoring sensor is in a state of non-attachment although the state of non-attachment is due to a normal circumstance of the monitoring sensor being charged.

According to another technical aspect, a wearable monitoring sensor is provided having: a biometric information detection unit for detecting biological response information; a storage unit for storing the biological response information detected by the biometric information detection unit; a power supply battery for supplying electric power to the biometric information detection unit and a wireless communication unit; and a wireless communication unit for transmitting the biological response information stored in the storage unit and the power level of the power supply battery to an outside unit. For example, a monitoring person at a remote location can thereby confirm a problem with insufficient power when biological response information has not been obtained. The monitoring person can then contact the monitored person through the appropriate means to restore and maintain the monitoring system.

According to a specific aspect, the wireless communication unit does not transmit biological response information to an outside unit when the power level of the power supply battery is insufficient. Confusion can thereby be prevented regarding the transmission of inappropriate biological response information during a low power state, and the transmission of biological response information can be performed more reliably. According to another specific aspect, the wireless communication unit does not perform a detection with the biometric information detection unit when the power level of the power supply battery is insufficient. It is thereby possible to prevent detection of inappropriate biological response information during a low power state, and the transmission of biological response information can be performed more reliably.

According to another technical aspect, a wearable monitoring sensor is provided having:
a biometric information detection unit for detecting biological response information; a storage unit for storing the biological response information detected by the biometric information detection unit; a power supply battery for supplying electric power to the biometric information detection unit and a wireless communication unit; a charging detection unit for detecting whether or not the power supply battery is being charged; and a wireless communication unit for transmitting biological response information stored in the storage unit and the detection results from the charging detection unit to an outside unit. For example, a monitoring person at a remote location can thereby obtain information on power levels needed to keep the monitoring system in operation.

According to a specific aspect, the wireless communication unit transmits whether not the monitoring sensor is attached to an outside unit, but does not transmit to the outside unit that the monitoring sensor is unattached when the charging detection unit has detected that the power supply battery is being charged. It is thereby possible to avoid confusion arising if what is transmitted to the monitoring person as an abnormal state is that the monitoring sensor is in a state of non-attachment although the state of non-attachment is due to a normal circumstance of the monitoring sensor being charged.

According to another technical aspect, a wearable monitoring sensor is provided having: a biometric information detection unit for detection biological response information; a storage unit for storing the biological response information detected by the biometric information detection unit; a power supply battery for supplying electric power to the biometric information detection unit and the wireless communication unit; an attachment detection unit for detecting whether or not the monitoring sensor is attached; and a wireless communication unit for transmitting the biological response information stored in the storage unit and the attachment status of the monitoring sensor to an outside unit. For example, a monitoring person at a remote location can thereby confirm whether or not the monitoring sensor indispensible for wearable monitoring is attached properly. According to a specific aspect, the wireless communication unit does not transmit biological response information to an outside unit when the monitoring sensor is not attached. This prevents wasteful consumption of the power supply.

According to another technical aspect, a wearable monitoring sensor is provided having: a biometric information detection unit for detecting biological response information; a storage unit for storing the biological response information detected by the biometric information detection unit; a display unit; and a wireless communication unit for transmitting the biological response information stored in the storage unit to an outside unit, and for receiving biological response information for another person from an outside unit for display on the display unit. One's own biological response information and another person's biological response information can thereby be shared. A sense of connection can thereby be fostered between people living alone, wearing a monitoring sensor can function as a membership card among those monitoring each other, and those being monitored can be encouraged to always wear their monitoring sensor.

According to another technical aspect, a wearable monitoring sensor is provided having: a biometric information detection unit for detecting biological response information; a storage unit for storing the biological response information detected by the biometric information detection unit; a power supply battery for supplying electric power to the biometric information detection unit and a wireless communication unit; a full charge detection unit for detecting whether or not the power supply battery is fully charged; and a wireless communication unit for transmitting the biological response information stored in the storage unit and the detection results from the full charge detection unit. For example, when a plurality of monitoring sensors is alternately charged and used, a monitoring sensor can thereby be promptly replaced by a fully charged monitoring sensor in order to maintain the monitoring system. At this time, full charge information from the monitoring sensor that is being charged can be received and displayed on the monitoring sensor currently being used. This can promote even faster replacement by a fully charged monitoring sensor.

As described above, a monitoring sensor can be provided according to the fifth technical aspect which is suitable for used in a biometric information measurement device.

The fifth technical aspect provides a wearable monitoring sensor able to be used by a monitored person who lives alone.

<Sixth Technical Aspect>

The sixth technical aspect disclosed herein relates to a monitoring system.

Various monitoring systems have been studied in recent years for elderly persons living alone, given the advent of an aging society. For example, monitoring these persons by detecting pulse abnormalities has been proposed (e.g., International Laid-open Patent Publication No. WO2003/096892).

In addition, there has been proposed an activity monitoring system provided with transmitting means for transmitting, via email, signals outputted by daily activity information detecting means (e.g., Japanese Laid-open Patent Publication No. 2002-251686).

However, many unexamined problems remain related to the execution of smooth monitoring during daily activities.

In view of this situation, an object of the sixth technical aspect is to provide a practical monitoring system able to perform smooth monitoring.

In order to achieve this object, the sixth technical aspect provides a monitoring system having a plurality of wearable monitoring sensors, and a common charger for charging the plurality of monitoring sensors. Each of the plurality of wearable monitoring sensors has: a biometric information detection unit for detecting biological response information; a storage unit for storing the biological response information detected by the biometric information detection unit; a wireless communication unit for communicating with an outside unit; and a power supply battery for supplying electric power to the biometric information detection unit and the wireless communication unit. A monitoring system can be constructed based on battery-powered wearable monitoring sensors that do not obstruct daily activities. At least one monitoring sensor can be charged by the common charger while another monitoring sensor is being used, and uninterrupted monitoring can be performed by alternating use of these sensors.

According to a specific aspect, one of the plurality of monitoring sensors has a display unit for displaying the charge status of another monitoring sensor received via the wireless communication unit. This allows the status of the monitoring sensor being charged to be ascertained via the monitoring sensor being used, and encourages the uninterrupted exchange and use of the monitoring sensors.

According to another specific aspect, the plurality of monitoring sensors has different functions. According to another specific aspect, for example, one of the plurality of monitoring sensors is for night-time use and is used to detect the health status of the wearer while sleeping, and another monitoring sensor is for day-time use and is used to detect the presence or absence of biological reactions. According to another specific aspect, one of the plurality of monitoring sensors is for night-time use and is used to continuously detect biometric information in the wearer, and another monitoring sensor is for day-time use and is used to intermittently detect biometric information. By using a plurality of monitoring sensors having different functions based on the rhythm of daily activity, optimum monitoring can be realized, and the natural exchange and use of monitoring sensors can be facilitated.

According to another technical aspect, a monitoring system is provided having a wearable monitoring sensor, and a charger for charging the monitoring sensor and for outputting information related to receiving a charge. This wearable monitoring sensor has a biometric information detection unit for detecting biological response information, a storage unit for storing the biological response information detected by the biometric information detection unit, a wireless communication unit for transmitting the biological response information stored in the storage unit to the monitoring party, and a power supply battery for supplying electric power to the biometric information detection unit and the wireless communication unit. Information related to the charge needed by the wearable monitoring sensor can thereby be obtained directly from the charger.

According to a specific aspect, the charger outputs information indicating whether or not one of the monitoring sensors is being charged. It can thereby be determined whether or not an unused monitoring sensor has been charged for its next use. This facilitates the exchange and use of monitoring sensors. According to another specific aspect, the charger outputs information indicating whether or not a monitoring sensor has been completely charged. This facilitates the exchange and use of monitoring sensors without any power shortage occurring.

According to another technical aspect, a monitoring system is provided having a plurality of wearable monitoring sensors, a wireless communication unit for communicating with the plurality of monitoring sensors, and a monitoring management unit equipped with a control unit for ascertaining the status of the plurality of monitoring sensors via communication with the wireless communication unit. Each of the plurality of wearable monitoring sensors has a biometric information detection unit for detecting biological response information, a storage unit for storing the biological response information detected by the biometric information detection unit, a wireless communication unit for communicating with an outside unit, and a power supply battery for supplying electric power to the biometric information detection unit and the wireless communication unit. A system including a plurality of monitoring sensors can thereby be managed without disruptions.

According to a specific aspect, a monitoring management unit ascertains the status related to the charging of one monitoring sensor when another monitoring sensor is being used. It is thereby possible to ascertain how a plurality of monitoring sensors are exchanged when they are being charged, even when monitoring is performed remotely. Also, information from the monitoring sensor being used and the monitoring sensor being charged can be ascertained and managed without disruption.

According to another technical aspect, a monitoring system is provided having a wearable monitoring sensor and a monitoring management unit. This wearable monitoring sensor has a biometric information detection unit for detecting biological response information, a storage unit for storing the biological response information detected by the biometric information detection unit, a wireless communication unit for transmitting the biological response information stored in the storage unit to the monitoring party, and a power supply battery for supplying electric power to the biometric information detection unit and the wireless communication unit. The monitoring management unit in the present invention has a receiving unit for receiving biological response information from the monitoring sensor, a telephone function unit, and a control unit for determining the transmission destination for the biological response information received by the receiving unit based on the biological response information from the monitoring sensor. A monitoring system having a plurality of biological reaction transmission destinations can thereby be managed appropriately.

According to a specific aspect, the control unit determines another wearable monitoring sensor by transmission destination when the biological response information is normal. For example, it thereby is possible to foster a sense of connection between people living alone by allowing them to monitor each other's daily activity without generating excessive tension. According to another specific aspect, a specific monitoring management base is selected by the control unit based on the transmission destination when biological response information is abnormal. For example, extraordinarily abnormal signals can thereby be transmitted in a timely manner to the monitoring management base responsible for monitoring by agreement, and the transmission of normal signals to the monitoring management base responsible for collecting information can be prevented.

According to another technical aspect, a monitoring system can be provided having a wearable monitoring sensor and a mobile telephone. This wearable monitoring sensor has a biometric information detection unit for detecting biological response information, a storage unit for storing the biological response information detected by the biometric information detection unit, a wireless communication unit for transmitting the biological response information stored in the storage unit to the monitoring party, and a power supply battery for supplying electric power to the biometric information detection unit and the wireless communication unit. The mobile telephone has a receiving unit for receiving biological response information from the monitoring sensor, a telephone function unit, and a control unit for controlling, based on the biological response information from the monitoring sensor, whether to give priority to the transfer of the biological response information received by the receiving unit or a telephone call using the telephone function unit. A monitoring system can thereby be realized which is able to respond to emergency situations without compromising the original function of the mobile telephone.

According to a specific aspect, the control unit gives priority to telephone calls using the telephone function when the biological response information is normal. The original function of a mobile telephone is thereby not compromised by the monitoring function in everyday life. According to another specific aspect, the control unit gives priority to the transmission of biological response information received by the receiving unit when the biological response information is abnormal. The system can thereby respond in a timely manner to extraordinarily abnormal signals.

As described above, a monitoring system can be provided in the sixth technical aspect which is suitable for the inclusion of wearable monitoring sensors.

The sixth technical aspect can be used in a monitoring system including a wearable monitoring sensor.

<Summary of the Seventh Technical Aspect Shown in Example 11>

The various technical aspects disclosed herein are summarized by the seventh technical aspect shown in Example 11.

The seventh technical aspect relates to various applications in which a pulse sensor is used in a game system (including a program realized by the game system and an information storage medium for storing this program).

Games have been developed using various input interfaces. For example, a game system has been disclosed and proposed in Japanese Laid-open Patent Publication No. 2003-024622 in which tastes and smells detected from the outside are used as game elements.

However, in game systems of the prior art, it is impossible to have the game reflect, e.g., the physical condition and degree of excitement of the player.

In view of this problem discovered by the present inventors, an object of the seventh technical aspect is to provide a game system, a program for controlling the game system, and an information storage medium for storing the program which allows, e.g., the physical condition and degree of excitement of the player to be reflected in the game.

In order to realize this object, a game system equipped with the seventh technical aspect has a pulse wave sensor for measuring the pulse waves from a body, and is configured so as to use the pulse wave information obtained using the pulse wave sensor as data in the game (first configuration).

A game system with the first configuration can also have a main processing unit for overall control of the operations of the entire game system, a video processing unit for generating video data, and an audio processing unit for generating audio data. In this configuration (the second configuration), the main processing unit issues instructions to the video processing unit and the audio processing unit to generate at least one of video data and audio data so as to reflect the pulse wave information.

In a game system with the second configuration, the main processing unit can be configured to send instructions to the video processing unit and the audio processing unit so that at least the facial expression or voice of the game character reflects pulse wave information (third configuration).

In a game system with the second or third configuration, the main processing unit can be configured to calculate the vascular age of the player based on the output of the pulse wave sensor and to use the vascular age as data in the game (fourth configuration).

In a game system with the fourth configuration, the main processing unit can be configured to calculate the vascular ages of a plurality of players based on the output of the pulse wave sensor and to use the vascular ages and comparative results as data in the game (fifth configuration).

In a game system with any one of the second through fifth configurations, the main processing unit can be configured to simultaneously or nearly simultaneously obtain pulse wave information from a plurality of players based on the output from a plurality of pulse wave sensors and to use the pulse wave information as data in the game (sixth configuration).

In a game system with any one of the second through sixth configurations, a communication unit can be provided for sending and receiving pulse wave information to and from another game system or server (seventh configuration).

In a game system with the seventh configuration, the main processing unit can be configured to link a plurality of players based on a plurality of pulse wave information sets obtained via the communication unit, and to send instructions to the video processing unit and the audio processing unit so as to output the results of the link (eighth configuration).

In a game system with any one of the second through eighth configurations, an information storage unit can be provided to stamp pulse wave information with the date and time and to hold the pulse wave information (ninth configuration).

In a game system with any one of the second through ninth configurations, the main processing unit can be configured to send instructions to the video processing unit and the audio processing unit so as perform at least one of generating a game character, changing an attribute, and transforming the character to reflect the pulse wave information (tenth configuration).

In a game system with any one of the second through tenth configurations, the main processing unit can be configured to determine whether or not the response of a player is true based on pulse wave information obtained when the player responded to a question, and to use the results of the determination as data in the game (eleventh configuration).

In a game system with any one of the second through eleventh configurations, the pulse wave sensor can be configured so as to be attached to a pet (twelfth configuration).

In a game system with any one of the second through eleventh configurations, the pulse wave sensor can be configured so as to be attached to a player while sleeping (thirteenth configuration).

The program in the seventh technical aspect is a program for controlling a game system having a pulse wave sensor for measuring the pulse waves in a body, a main processing unit for overall control of the operations of the entire game system, a video processing unit for generating video data, and an audio processing unit for generating audio data. In this configuration (fourteenth configuration), the program is retrieved and executed so that the main processing unit functions as means for issuing instructions to the video processing unit and the audio processing unit to generate at least one of video data and audio data so as to reflect the pulse wave information.

The information storage medium in the seventh technical aspect is an information storage medium that can be read by the game system, and is configured to store a program with the fourteenth configuration (fifteenth configuration).

In the seventh technical aspect, for example, a game system, a program for controlling the game system, and an information storage medium for storing the program can be provided which allows the physical condition and degree of excitement of the player to be reflected in the game.

LIST OF REFERENCE NUMERALS

<First Technical Aspect>
18: Light-Emitting Unit
20: Light-Receiving Unit
24: Storage unit
4, 104, 204, 504, 604: External Processing Units
28: Short-Range Communication Unit
30: Power Supply Unit
208: Waterproof Structure
32: Storage Cell
208: Contactless Electromagnetic Induction Unit
25: Acceleration Sensor
40: Solar Cell
<Second Technical Aspect>
18: Light-Emitting Unit
20: Light-Receiving Unit
102, 202, 302, 402, 502: Sensor Blocks
44, 318: Input Units
44, 318: Output Units
50: Display Unit
42: Control Unit
104: Mobile telephone
304, 504: Portable Music Terminal
310: Music Playback Unit
104, 204, 304, 504: Mobile Device
<Third Technical Aspect>
18, 20: Measurement unit
2, 602: Biometric Measurement Block
24: Storage unit
28: Transmitting Unit
44, 606, 614: Receiving Units
42: Processing Unit
4, 604: Processing Blocks
42: Analyzing Unit
42: Designating Unit
<Fourth Technical Aspect>
18, 20: Measurement units
802: Biometric Block
827: Storage unit for Measurement unit-Specific Information
827, 828: Transmitting Units 811, 806: Receiving Units
831, 833, 835: Transfer Units
808: Receiving Block
42: Processing Unit
804: Processing Block
809: Storage unit for Receiving Block-Specific Information
809: Training Function Unit
608: Lane rope
56, 50: Input Units
24: Storage unit for Measurement Information
802: Ring
30: Power Supply Unit
208: Contactless Charging Unit
42: Designating Unit
827: IC Tag
811: IC Tag Reader
18, 20: First Measurement Unit
20: Transmitting Unit
202: Measurement Block
220: Second Measurement Unit
44: Receiving Unit
204: Processing Block
202: Ring-Shaped Measurement Block
204: Wristwatch-Type Processing Block
 <Fifth Technical Aspect>
18, 20: Biometric Information Detection Units
24: Storage unit
28: Wireless Communication Unit
32: Power Supply Battery
907, 26, 28, 922: Trigger Units
908: Charging Detection Unit
8, 20: Installation Detection Units
39: Display Unit
910: Charging Completion Detection Unit
 <Sixth Technical Aspect>
18, 20: Biometric Information Detection Units
24: Storage unit
28: Wireless Communication Unit
32: Power Supply Battery
39: Display Unit
949: Daytime Monitoring Sensor
951: Nighttime Monitoring Sensor
42, 942: Control Units
904: Monitoring Management Unit
104, 933: Mobile telephones
 <Seventh Technical Aspect>
X10: Game Console
X10A, X10B, X10C: Game Consoles
X11: Main Processing Unit
X12: Secondary Processing Unit
X13: Information Storage unit
X14: Video Processing Unit
X15: Audio Processing Unit
X16A, X16B, X16C: Communication Units
X20: Controller
X30: Information Storage Medium
X31: Game Program
X40: Game Output Unit
X50: Pulse Wave Sensor
X50-1, X50-2: Pulse Wave Sensors
X50A, X50B, X50C: Pulse Wave Sensors
X60: Network
X70: Server
P1, P2: Players
PA, PB, PC: Players
Pa: Pet
Pb: Player

What is claimed is:

1. A wireless plethysmogram sensor unit capable of obtaining a plethysmogram from a living tissue of a measuring object and of transmitting the obtained plethysmogram to a processing unit outside the wireless plethysmogram sensor unit, the processing unit being capable of receiving plethysmogram of a plurality of measuring objects obtained by a plurality of wireless plethsymogram sensor units, respectively, comprising:
 a light source provided inside the wireless plethysmogram sensor unit and arranged to emit measuring light into the living tissue;
 a light receiving element provided inside the wireless plethysmogram sensor unit and arranged to receive light emerging from the living tissue which is the measuring light in origin and accompanied by pulsation caused by absorption by arteries in the living tissue;
 a memory provided inside the wireless plethysmogram sensor unit and arranged to store a plethysmogram obtained in accordance with the light received by the light receiving element;
 a short range wireless communicator provided inside the wireless plethysmogram sensor unit and arranged to transmit the plethysmogram stored in the memory to the processing unit;
 a power source provided inside the wireless plethysmogram sensor unit to power elements provided inside the wireless plethysmogram sensor unit; and
 a controller provided inside the wireless plethysmogram sensor unit and arranged to control the elements provided inside the wireless plethysmogram sensor unit,
 wherein the short range wireless communicator is arranged to transmit information for identifying the plethysmogram sensor to the processing unit, and
 wherein the short range wireless communicator is arranged to transmit information for identifying the measuring object to the processing unit, the information for identifying the plethysmogram sensor unit and the information for identifying the measuring object allowing the processing unit to distinguish a specific combination of the wireless plethysmogram sensor unit and the measuring object from other combinations among the plurality of wireless plerhismogram sensor units and the plurality of the measuring objects.

2. The wireless plethysmogram sensor unit according to claim 1 wherein the power source includes a rechargeable battery and a charging arrangement capable of receiving electric power from the outside.

3. The wireless plethysmogram sensor unit according to claim 2 wherein the short range wireless communicator is arranged to inform the processing unit of whether or not the charging arrangement is in a condition for receiving electric power from the outside.

4. The wireless plethysmogram sensor unit according to claim 3 wherein the short range wireless communicator is arranged to inform the processing unit of whether or not the charging has been completed with the charging arrangement in a condition for receiving electric power from the outside.

5. The wireless plethysmogram sensor unit according to claim 1 wherein the short range wireless communicator is arranged to receive an instruction from the processing unit related to one of the measurement and the transmission of a plethysmogram.

6. The wireless plethysmogram sensor unit according to claim 1 wherein the short range wireless communicator is arranged to inform the processing unit of whether or not the wireless plethysmogram sensor unit is attached to the measuring object.

7. A wireless plethysmogram sensor unit capable of obtaining a plethysmogram from a living tissue of a measuring object and of transmitting the obtained plethysmogram to a processing unit outside the wireless plethysmogram sensor unit, comprising:
- a light source provided inside the wireless plethysmogram sensor unit and arranged to emit measuring light into the living tissue;
- a light receiving element provided inside the wireless plethysmogram sensor unit and arranged to receive light emerging from the living tissue which is the measuring light in origin and accompanied by pulsation caused by absorption by arteries in the living tissue;
- a memory provided inside the wireless plethysmogram sensor unit and arranged to store a plethysmogram obtained in accordance with the light received by the light receiving element;
- a short range wireless communicator provided inside the wireless plethysmogram sensor unit and arranged to transmit the plethysmogram stored in the memory to the processing unit;
- a power source provided inside the wireless plethysmogram sensor unit to power elements provided inside the wireless plethysmogram sensor unit;
- a controller provided inside the wireless plethysmogram sensor unit and arranged to control the elements provided inside the wireless plethysmogram sensor unit; and
- an environmental change sensor provided inside the wireless plethysmogram sensor unit, wherein the controller is arranged to autonomously control the light source and the light receiving element so as to trigger a measurement in automatic response to the environmental change sensor.

8. The wireless plethysmogram sensor unit according to claim 7 further comprising a timer provided inside the wireless plethysmogram sensor unit, wherein the controller is arranged to autonomously control the light source and the light receiving element so as to start a measurement in response to the timer.

9. The wireless plethysmogram sensor unit according to claim 7 wherein the short range wireless communicator is arranged to inform the processing unit of the condition of the power source.

10. A wireless plethysmogram sensor unit capable of obtaining a plethysmogram from a living tissue of a measuring object and of transmitting the obtained plethysmogram to a processing unit outside the wireless plethysmogram sensor unit, comprising:
- a light source provided inside the wireless plethysmogram sensor unit and arranged to emit measuring light into the living tissue;
- a light receiving element provided inside the wireless plethysmogram sensor unit and arranged to receive light emerging from the living tissue which is the measuring light in origin and accompanied by pulsation caused by absorption by arteries in the living tissue;
- a memory provided inside the wireless plethysmogram sensor unit and arranged to store a plethysmogram obtained in accordance with the light received by the light receiving element;
- a short range wireless communicator provided inside the wireless plethysmogram sensor unit and arranged to transmit the plethysmogram stored in the memory to the processing unit;
- a power source provided inside the wireless plethysmogram sensor unit to power elements provided inside the wireless plethysmogram sensor unit;
- a controller provided inside the wireless plethysmogram sensor unit and arranged to control the elements provided inside the wireless plethysmogram sensor unit; and
- a display for monitoring information relating to a plethsmotram obtained in accordance with the light received by the light receiving element,
- wherein the short range wireless communicator is arranged to receive information relating to a plethysmogram obtained by another individual wireless plethysmogram sensor unit to monitor the received information on the display, the monitored information on the display being unique to the individual plethysmogram sensor unit.

11. The wireless plethysmogram sensor unit according to claim 10, wherein the plethysmogram is of a human being and utilized for any one of monitoring a training approach in a gym, confirming safety for a solitary life, and conditioning the progress of an amusement device, to which a human being relates.

12. A processing unit capable of receiving plethysmogram from a plurality of wireless plethysmogram sensor units, respectively, including the wireless plethysmogram sensor unit according to claim 10 comprising a short range wireless communicator arranged to receive a plethysmogram from one of the wireless plethysmogram sensor units.

* * * * *